US008592584B2

(12) United States Patent
Hergenrother et al.

(10) Patent No.: US 8,592,584 B2
(45) Date of Patent: Nov. 26, 2013

(54) COMPOSITIONS AND METHODS INCLUDING CELL DEATH INDUCERS AND PROCASPASE ACTIVATION

(75) Inventors: Paul J. Hergenrother, Champaign, IL (US); Karson S. Putt, Champaign, IL (US); Quinn P. Peterson, Savoy, IL (US); Valerie Fako, Naperville, IL (US)

(73) Assignee: The Board of Trustees of the of The University of Illinois, Urbana, IL (US)

( * ) Notice: Subject to any disclaimer, the term of this patent is extended or adjusted under 35 U.S.C. 154(b) by 0 days.

(21) Appl. No.: 13/087,595

(22) Filed: Apr. 15, 2011

(65) Prior Publication Data

US 2011/0257398 A1 Oct. 20, 2011

Related U.S. Application Data

(63) Continuation of application No. 12/597,287, filed as application No. PCT/US2008/061510 on Apr. 25, 2008, now abandoned, said application No. 12/597,287 is a continuation-in-part of application No. 11/420,425, filed on May 25, 2006, now abandoned.

(60) Provisional application No. 60/914,592, filed on Apr. 27, 2007, provisional application No. 60/684,807, filed on May 26, 2005, provisional application No. 60/743,878, filed on Mar. 28, 2006.

(51) Int. Cl.
*A61K 31/495* (2006.01)
*C07D 211/62* (2006.01)
*C07D 295/13* (2006.01)
*C07D 295/15* (2006.01)
*C07D 403/12* (2006.01)
*C07D 211/34* (2006.01)
*C07D 401/06* (2006.01)
*C07D 241/04* (2006.01)

(52) U.S. Cl.
USPC ............ 544/357; 544/360; 544/400; 546/245

(58) Field of Classification Search
None
See application file for complete search history.

(56) References Cited

U.S. PATENT DOCUMENTS

| | | | |
|---|---|---|---|
| 3,702,879 A | 11/1972 | Hellmut et al. |
| 3,847,866 A | 11/1974 | Iliopulos et al. |
| 3,879,498 A | 4/1975 | Iliopulos et al. |
| 4,463,159 A | 7/1984 | Besecke et al. |
| 5,569,673 A | 10/1996 | Morre et al. |
| 6,303,329 B1 | 10/2001 | Heinrikson et al. |
| 6,403,765 B1 | 6/2002 | Alnemri |
| 6,444,638 B2 | 9/2002 | Schwartz et al. |
| 6,489,476 B1 | 12/2002 | Dang et al. |
| 6,534,267 B1 | 3/2003 | Wang et al. |
| 6,548,536 B2 | 4/2003 | Hara et al. |
| 6,558,900 B2 | 5/2003 | Wang et al. |
| 6,605,589 B1 | 8/2003 | Uckun et al. |
| 6,608,026 B1 | 8/2003 | Wang et al. |
| 6,627,623 B2 | 9/2003 | Ho et al. |
| 6,762,045 B2 | 7/2004 | Krebs et al. |
| 6,878,743 B2 | 4/2005 | Choong et al. |
| 7,041,784 B2 | 5/2006 | Wang et al. |
| 7,053,071 B2 | 5/2006 | Dawson et al. |
| 7,632,972 B2 | 12/2009 | Hergenrother et al. |
| 2003/0032045 A1 | 2/2003 | Wang et al. |
| 2003/0148966 A1 | 8/2003 | Jayaram et al. |
| 2003/0198949 A1 | 10/2003 | Goldmakher et al. |
| 2004/0077542 A1 | 4/2004 | Wang et al. |
| 2004/0180828 A1 | 9/2004 | Shi |
| 2005/0197511 A1 | 9/2005 | Hergenrother et al. |
| 2007/0049602 A1 | 3/2007 | Hergenrother et al. |
| 2011/0257398 A1 | 10/2011 | Hergenrother et al. |
| 2012/0040995 A1 | 2/2012 | Hergenrother et al. |

FOREIGN PATENT DOCUMENTS

| | | |
|---|---|---|
| WO | WO 02/083114 | 10/2002 |
| WO | WO 2005/044191 | 5/2005 |
| WO | WO 2005/090370 | 9/2005 |
| WO | WO 2006/128173 | 11/2006 |
| WO | WO 2007/008529 | 1/2007 |
| WO | WO 2008/134474 | 11/2008 |
| WO | WO 2010/091382 | 8/2010 |

OTHER PUBLICATIONS

Putt et al., Nature Chemical Biology, 2006, vol. 2, 543-550.*
T. Bunyapaiboonsri et al., "Generation of Bis-Cationic Heterocyclic Inhibitors of Bacillus subtilis HPr Kinase/Phosphatase from a Ditopic Dynamic Combinatorial Library," J. Med. Chem. 46:5803-5811, 2003.
A. Ling et al., "Identification of Alkylidene Hydrazides as Glucagon Receptor Antagonists," J. Med. Chem. 44:3141-3149, 2001.
Q. Peterson et al., "Procaspase-3 Activation as an Anti-Cancer Strategy: Structure-Activity Relationship of Procaspase-Activating Compound 1 (PAC-1) and its Cellular Co-Localization with Caspase-3," J. Med. Chem. 52:5721-5731, 2009.
A. Silva et al., "Synthesis and Vasodilatory Activity of New N-acylhydrazone Derivatives, Designed as LASSBio-295 Analogues," Bioorganic & Medicinal Chemistry 13:3431-3437, 2005.
M. Tiecco et al., "Factors Controlling the Selenium-Induced Cyclizations of Alkenyl Hydrazines to Pyridazine or Pyrrolidinamine Derivatives," Tetrahedron 53(30):10591-10602, 1997.
Adjei et al. (2003) "Novel Anticancer Agents in Clinical Development," *Cancer Biol. Ther.* S1:S5-S15.
Adler et al. (1997) "Protection by the Heavy Metal Chelator N,N,N',N'-Tetrakis (2-Pyridylmethyl)ethylenediamine (TPEN) Against the Lethal Action of Botulinum Neurotoxin A and B," *Toxicon* 35(7):1089-1100.

(Continued)

*Primary Examiner* — Sun Jae Loewe
(74) *Attorney, Agent, or Firm* — Lathrop & Gage LLP

(57) ABSTRACT

Compositions and methods are disclosed in embodiments relating to induction of cell death such as in cancer cells. Compounds and related methods for synthesis and use thereof, including the use of compounds in therapy for the treatment of cancer and selective induction of apoptosis in cells are disclosed. Compounds are disclosed in connection with modification of procaspases such as procaspase-3. In embodiments, compositions are capable of activation of procaspase-3.

1 Claim, 21 Drawing Sheets

(56) References Cited

OTHER PUBLICATIONS

Aiuchi et al. (1998) "Zinc Ions Prevent Processing of Caspase-3 During Apoptosis Induced by Geranylgeraniol in HL-60 Cells," *J. Biochem.* 124:300-303.

Alley et al. (Feb. 1, 1988) "Feasibility of Drug Screening with Panels of Human Tumor Cell Lines Using a Microculture Tetrazolium Assay," *Cancer Res.* 48:589-601.

Anderson et al. (1996) "A Phase I Study of a 24 Hour Infusion of Gemcitabine in Previously Untreated Patients with Inoperable Non-Small-Cell Lung Cancer," *Br J Cancer* 74:460-462.

Becattini et al. (2004) "Rational Design and Real Time, In-Cell Detection of the Proapoptotic Activity of a Novel Compound Targeting Bcl-XL," *Chem. Biol.* 11:389-395.

Beyersmann et al. (2001) "Functions of Zinc in Signaling, Proliferation and Differentiation of Mammalian Cells," *BioMetals* 14:331-341.

Bhattacharya et al. (1981) "The Michaelis-Arbuzov Rearrangement," *Chem. Rev.* 81:415-430.

Blake et al. (Jun. 1997) "Estrogen Can Protect Splenocytes from the Toxic Effects of the Environmental Pollutant 4-*tert*-Octylphenol," *Endocrine* 6:243-249.

Blatt et al. (2001) "Signaling Pathways and Effector Mechanisms Pre-Programmed Cell Death," *Bioorg. Med. Chem. Lett.* 9:1371-1384.

Boatright et al. (2003) "Mechanisms of Caspase Activation," *Curr. Opin. Cell. Biol.* 15:725-731.

Boisselle et al. (1962) "Acetylene-Allene Rearrangements. Reactions of Trivalent Phosphorous Chlorides with Alpa-Acetylenic Alcohols and Glycols," *J. Org. Chem.* 27(5):1828-1833.

Bose et al. (2003) "An Uncleavable Procaspase-3 Mutant has a Lower Catalytic Efficiency but an Active Site Similar to that of Mature Caspase-3," *Biochemistry* 42:12298-12310.

Boyd et al. (1995) "Some Practical Considerations and Applications of the National Cancer Institute in Vitro Anticancer Drug Discovery Screen," *Drug Dev. Res.* 34:91-109.

Breen et al. (2008) "Evolutionarily Conserved Cytogenetic Changes in Hematological Malignancies of Dogs and Humans—Man and his Best Friend Share More than Companionship," *Chromosome Res.* 16:145-154.

Buckley et al. (Feb. 11, 1999) "RGD Peptides Induce Apoptosis by Direct Caspase-3 Activation," *Nature* 397:534-539.

Bundgaard, H. (1985) "Design of Prodrugs," *Methods Enzymol.* 42:309-396.

Bundgaard, (1988) "Glycolamide Esters as Biolabile Prodrugs of Carboxylic Acid Agents: Synthesis, Stability, Bioconversion, and Physicochemical Properties," *J. Pharm. Sci.* 77(4):285-298.

Bundgaard, H. (1991) "Design and Application of Prodrugs," In; *A Textbook of Drug Design and Development*, Krosgaard et al. eds., Ch. 5, pp. 113-191.

Bundgaard, H. (1992) "(C) Means to Enhance Penetration: (1) Prodrugs as a Means to Improve the Delivery of Peptide Drugs," *Adv. Drug Deliv. Rev.* 8:1-38.

Cannon-Albright et al. (Nov. 13, 1992) "Assignment of a Locus for Familial Melanoma, MLM, to Chromosome 9p13-p22," *Science* 258:1148-1152.

Chai et al. (1999) "Regulation of Caspase Activation and Apoptosis by Cellular Zinc Fluxes and Zinc Depreciation: A Review," *Immunol. Cell Biol.* 77:272-278.

Charkoudian et al. (2006) "A Pro-Chelator Triggered by Hydrogen Peroxide Inhibits Iron-promoted Hydroxyl Radical Formation," *J. Am. Chem. Soc.* 128:12424-12425.

Chemical Abstracts Service Accession No. 488086-61-9, Abstract, Feb. 10, 2003.

Chemical Abstracts Service Accession No. 315198-34-6, Abstract, Jan. 19, 2001.

Chimienti et al. (2001) "Role of Cellular Zinc in Programmed Cell Death: Temporal Relationship Between Zinc Depletion, Activaition of Caspases, and Cleavage of Sp Family Transcription Factors," *Biochem. Pharmacol.* 62:51-62.

Chun et al. (2000) "Evaluation of a High-Dose Chemotherapy Protocol with no Maintenance Therapy for Dogs with Lymphoma," *J. Vet. Intern. Med.* 14:120-124.

Ciardiello et al. (2000) "Antitumor Effect and Potentiation of Cytotoxic Drugs Activity in Human Cancer Cells by ZD-1839 (Iressa), an Epidermal Growth Factor Receptor-selective Tyrosine Kinase Inhibitor," *Clinical Cancer Research* 6:2053-2063.

Clark, D.E. (2003) "Silico Prediction of Blood-Brain Barrier Permeation," *Drug Discov Today* 8(20):927-933.

Cossarizza et al. (2001) "Analysis of Mitochondria During Cell Death," *Methods Cell Biol.* 63:467-486.

Dauzonne et al. (1997) "Synthesis and in Vitro Cytotoxicity of a Series of 3-Aminoflavones," *Eur. J. Med. Chem.* 32(1):71-82.

De Graaff et al. (1999) "In Vitro Antagonistic Cytotoxic Interactions Between Platinum Drugs and Taxanes on Bone Marrow Progenitor Cell CFU-GM," *Anticancer Drugs* 10:213-218.

Degterev et al. (2001) "Identification of Small-Molecule Inhibitors of Interaction Between the BH3 Domain and Bcl-XL," *Nature Cell Biol.* 3:173-182.

Denault et al. (2003) "Human Caspase-7 Activity and Regulation by its N-Terminal Peptide," *J. Biol. Chem.* 278:34042-34050.

Denicourt et al. (2004) "Targeting Apoptotic Pathways in Cancer Cells," *Science* 305:1411-1413.

Dominguez et al. (2003) "Zinc Chelation During Non-Lesioning Overexcitation Results in Neuronal Death in the Mouse Hippocampus," *Neuroscience* 116:791-806.

Dominguez et al. (2006) "Neural Overexcitation and Implication of NMDA and AMPA Receptors in a Mouse Model of Temporal Lobe Epilepsy Implying Zinc Chelation," *Epilepsia* 47(5):887-899.

Dothager et al. (Jun. 22, 2005) "Synthesis and Identification of Small Molecules that Potently Induce Apoptosis in Melanoma Cells Through G1 Cell Cycle Arrest," *J. Am. Chem. Soc.* 127(24):8686-8696.

Druker et al. (1996) "Effects of a Selective Inhibitor of the Abl Tyrosine Kinase on the Growth of Bcr-Abl Positive Cells," *Nat Med* 2(5):561-566.

Earnshaw et al. (1999) "Mammalian Caspases: Structure, Activation, Substrates, and Functions During Apoptosis," *Ann. Rev. Biochem.* 68:383-424.

Edelmann et al. (Mar. 12, 2011) "*Homo sapiens* Caspase 7, Apoptosis-Related Cystene Peptidase," NCBI Accession No. NM_001227.

European Supplementary Search Report, Application No. EP 06771588, Jul. 19, 2010, 2 pages.

European Supplementary Search Report, Application No. EP 10739254, Jul. 25, 2012, 3 pages.

Fesik, S.W. (Nov. 2005) "Promoting Apoptosis as a Strategy for Cancer Drug Discovery," *Nat Rev Cancer* 5:876-885.

Fingl et al. (1975) "General Principles," In; *The Pharmacological Basis of Therapeutics*, Ch. 1, pp. 1-46.

Fink et al. (2001) "Elevated Procaspase Levels in Human Melanoma," *Melanoma Res.* 11:385-393.

Fountain et al. (Nov. 1, 1992) "Homozygous Deletions Within Human Chromosome Band 9p21 in Melanoma," *Proc. Nat. Acad. Sci. USA* 89:10557-10561.

Frederickson et al. (Jun. 2005) "The Neurobiology of Zinc in Health and Disease," *Nat. Rev. Neurosci.* 6:449-462.

Fujita et al. (1998) "Acceleration of Apoptotic Cell Death After the Cleavage of Bcl-XL Protein by Caspase-3-Like Proteases," *Oncogene* 17:1295-1304.

Gallagher et al. (Sep. 1979) "Characterization of the Continuous, Differentiating Myeloid Cell Line (HL-6-) from a Patient with Acute Promyelocytic Leukemia," *Blood* 54:713-733.

Garrett et al. (2002) "Evaluation of a 6-Month Chemotherapy Protocol with no Maintenance Therapy for Dogs with Lymphoma," *J. Vet. Intern Med.* 16:704-709.

Goode et al. (Aug. 4, 2005) "Using Peptidic Inhibitors to Systematically Probe the S1' Site of Caspase-3 and Caspase-7," *Org. Lett.* 7(16):3529-3532.

Greyer et al. (Dec. 1992) "The National Cancer Institute: Cancer Drug Discovery and Development Program," *Seminars Oncology* 19(6):622-638.

(56) References Cited

OTHER PUBLICATIONS

Grossman et al. (1999) "Expression and Targeting of the Apoptosis Inhibitor, Survivin, in Human Melanoma," *J. Invest. Dermatol.* 113:1076-1081.

Hanahan et al. (Jan. 7, 2000) "The Hallmarks of Cancer," *Cell* 100:57-70.

Hartmann et al. (Mar. 14, 2000) "Caspase-3: A Vulnerable Factor and Final Effector in Apoptotic Death of Dopaminergic Neurons in Parkinson's Disease," *Proc. Nat. Acad. Sci. USA* 97:2875-2880.

Haskell, C.M. (1980) *Cancer Treatment*, 1st Ed., W.B. Saunders Company, pp. 62-87.

Haskell, C.M. (1991) *Cancer Treatment*, 3rd Ed., W.B. Saunders Company, pp. 62-87.

Haskell, C.M. (2001) *Cancer Treatment*, 5th Ed., W.B. Saunders Company, pp. 78-87.

Hatt, H.H. (1933) "The Constitutions of Some Phosphorus Derivatives of Triphenylmethane," *J. Chem. Soc.* :776-786.

Helmbach et al. (2001) "Drug-Resistance in Human Melanoma," *Int. J Cancer* 93:617-622.

Hergenrother, P.J. (2006) "Obtaining and Screening Compound Collections: A User's Guide and a Call to Chemists," *Curr. Opin. Chem. Biol.* 10(3):213-218.

Hsu et al. (Feb. 2009) "The Design, Synthesis and Evaluation of Procaspase Activating Compounds as Potential Personalized Anti-Cancer Drugs," Poster, Presented at the "Chemistry in Cancer Research: A Vital Partnership in Cancer Drug Discovery and Development," Conference, Feb. 8-11, 2009, New Orleans, LA. http://www.scs.uiuc.edu/~phgroup/comcollections.html, 2013.

Huang et al. (2007) "Highly Sensitive Fluorescent Probes for Zinc Ion Based on Triazolyl-Containing Tetradentate Coordination Motifs," *Org. Lett.* 9(24):4999-5002.

Huang et al. (Oct. 2002) "The Chemical Biology of Apoptosis: Exploring Protein-Protein Interactions and the Life and Death of Cells with Small Molecules," *Chem. Biol.* 9:1059-1072.

Huesca et al. (2009) "A Novel Small Molecule with Potent Anticencer Activity Inhibits Cell Growth by Modulating Intracellular Labile Zinc Homeostasis," *Mol. Cancer Therapeutics* 8:2586-2596.

Hwang et al. (2003) "N-Phenethyl-2-Phenylacetamide Isolated from *Xenorhabdus nematophilus* Induces Apoptosis Through Caspase Activation and Calpain-Mediated Bax Cleavage in U937 Cells," *Int. J. Oncol.* 22:151-157.

Igney et al. (Apr. 2002) "Death and Anti-Death: Tumor Resistance to Apoptosis," *Nature Rev. Cancer* 2:277-288.

International Search Report, International Application No. PCT/US2008/061510, Mailed Nov. 19, 2008, 3 pages.

International Search Report, International Application No. PCT/US06/20910, Mailed Apr. 3, 2007, 1 page.

International Search Report, International Application No. PCT/US04/35746, Mailed Jul. 22, 2005, 1 page.

International Search Report, International Application No. PCT/US2010/023543, Mailed Apr. 12, 2010, 3 pages.

Izban et al. (1999) "Characterization of the Interleukin-1 Beta-Converting Enzyme/Ced-3-Family Protease, Caspase-3/CPP32, in Hodgkin's Disease," *Am. J. Pathol.* 154:1439-1447.

Jemal et al. (2002) "Cancer Statistics," *CA Cancer J. Clin.* 52:23-47.

Jeong et al. (2000) "Aromatase Inhibitors from Isodon Excisus Var. Coreanuus," *Arch. Pharm. Res.* 23(3):243-245.

Jiang et al. (2003) "Distinctive Roles of PHAP Proteins and Prothymosin-Alpha in a Death Regulatory Pathway," *Science* 299:223-226.

Johnstone et al. (Jan. 25, 2002) "Apoptosis: A Link Between Cancer Genetics and Chemotherapy," *Cell* 108:153-164.

Karakas et al. (2009) "Structure of the Zinc-Bound Amino-Terminal Domain of the NMDA Receptor NR2B Subunit," *EMBO J.* 28:3910-3920.

Kers et al. (Sep. 15, 1997) "Aryl H-Phosphonates. 7. Studies on the Formation of Phosphorus-Carbon Bond in the Reaction of Triryl and Benzyl Halides with Dialkyl and Diphenyl H-Phosphonates," *Terahedron* 53(37):12691-12698.

Khan et al. (2003) "Three Tyrosine Inhibitors and Antioxidant Compounds from *Salsola foetida*," *Helvetics Chimica Acta* 86:457-464.

Khanna et al. (1990) "Newer Poperazino Oxadiazoled, Formazans, and Tetrazolium Salts as Antiparkinsonian Agents," *Ind. J. Chem. B Org. Chem. Inc. Med. Chem.* 29B(1):91-94.

Khanna et al. (2006) "The Dog as a Cancer Model," *Nat. Biotechnol.* 24(9):1065-1066.

Kimura et al. (2006) "*Homo sapiens* Caspase 7, Apoptosis-Related Cystene Peptidase (CASP7), Transcript Variant Alpha, mRNA," NCBI Accession No. NM_01227.

Klotzbucher et al. (2004) "Identification of Low Molecular Weight Compounds Mediating Apoptosis by Directly Inducing Cleavage of Procaspase 3," Abstract, In; *Proceedings of the 95th Annual Meeting, American Association for Cancer Research*, Mar. 27-31, Orlando Florida, Abstract No. 4894 (*Proc. Am. Assoc. Cancer. Res.* vol. 45).

Konstantinov et al. (1998) "Alkylphosphocholines: Effects on Human Leukemic Cell Lines and Normal Bone Marrow Cells," *Int. J. Cancer* 77:778-786.

Koty et al. (1999) "Antisense Bcl-2 Treatment Increases Programmed Cell Death in Non-Small Cell Lung Cancer Cell Lines," *Lung Cancer* 23:115-127.

Krepela et all. (Feb. 2004) "Increased Expression of Apaf-1 and Procaspase-3 and the Functionality of Intrinsic Apoptosis Apparatus in Non-Small Cell Lung Carcinoma," *Biol Chem* 385:153-168.

Kunishima et al. (2001) "Formation of Carboxamides by Direct Condensation of Carboxylic Acids and Amines in Alcohols Using a New Alcohol- and Water-Soluble Condensing Agent: DMT-MM," *Tetrahedron* 47:1551-1558.

Kunishima et al. (2002) "Approach to Green Chemistry of DMT-MM: Recovery and Recycle of Coproduct to Chloromethane-Free DMT-MM," *Tetrahedron Lett.* 43:3323-3326.

Lavoie et al. (2007) "Extracellular Chelation of Zinc Does Not Affect Hippocampal Excitability and Seizure-Induced Cell Death in Rats," *J Physiol* 578:275-89.

Lee et al. (2001) "Two New Constituents of *Isodon Excisus* and Their Evaluation in an Apoptosis Inhibition Assay," *J. Nat. Prod.* 64:659-660.

Lee et al. (2002) "Agastinal and Agastenol, Novel Lignans from *Agastache rugosa* and Their Evaluation in an Apoptosis Inhibition Assay," *J. Nat. Prod.* 65:414-416.

Lev et al. (Jun. 1, 2004) "Exposure of Melanoma Cells to Dacarbazine Results in Enhanced Tumor Growth and Metastasis in Vivo," *J. Clin. Oncol.* 22:2092-2100.

Li et al. (2000) "Immunotoxicity of *N,N*-Diethylaniline in Mice: Effect an Natural Killer Activity, Cytotoxic T Lymphocyte Activity, Lymphocyte Proliferation Response and Cellular Components of the Spleen," *Toxicology* 150:179-189.

Li et al. (2004) "A Small Molecule Smac Mimic Potentiates TRAIL- and TNFa-Mediated Cell Death," *Science* 305:1471-1474.

Liang et al. (2002) "Role of Caspase 3-Dependent Bcl-2 Cleavage in Potentiation of Apoptosis by Bcl-2," *Mol. Pharmacol.* 61:142-149.

Lo Russo et al. (1999) "Preclinical Antitumor Activity of XK469 (NSC 656889)," *Invest. New Drugs* 16:287-296.

Lowe et al. (2004) "Intrinsic Tumor Suppression," *Nature* 432:307-315.

Lucas et al. (2011) "Pharmacokinetics and Derication of an Anticancer Dosing Regimen for PAC-1, A Preferential Small Molecule Activator of Procaspase-3, in Healthy Dogs," *Invest. New Drugs* 29:901-911 (Published online May 25, 2010).

Makin et al. (Jun. 2003) "Recent Advances in Understanding Apoptosis: New Therapeutic Opportunities in Cancer Chemotherapy," *Trends Mol. Med.* 9:251-255.

Marvel Library Compound Collection, http://www.scs.uiuc.edu/~phgroup/comcollections.html, Downloaded on Jul. 18, 2006.

Marx, J. (Sep. 21, 2001) "New Leads on the 'How' of Alzheimers," *Science* 293:2192-2194.

Mattson et al. (Nov. 2000) "Apoptosis in Neurodegenerative Disorders," *Nat. Rev. Mol. Cell Biol.* 1:120-129.

McGovern et al. (1985) "Pathology of Melanoma: An Overview," In; *Cutaneous Melnoma: Clinical Management and Treatment Results Worldwide*, Ch 3, Balch et al. eds., J.B. Lippincott Co., Philadelphia, pp. 29-42.

(56) References Cited

OTHER PUBLICATIONS

Meergans et al. (2000) "The Short Prodomain Influences Caspase-3 Activation in HeLa Cells," *Biochem. J.* 349:135-140.

Middleton et al. (2000) "A Randomized Phase III Study Comparing Dacarbazine, BCNU, Cisplatin and Tamoxifen with Dacarbazine and Inerferon in Advanced Melanoma," *Br. J. Cancer* 82:1158-1162.

Migianu et al. (2005) "New Efficient Synthesis of 1-Hydroxymethylene-1,1-Bisphosphonate Monomethyl Esters," *Synlett.* 3:425-428.

Monks et al. (Oct. 1997) "The NCI Anti-Cancer Drug Screen: A Smart Screen to Identify Effectors of Novel Targets," *Anti-Cancer Drug Design* 12(7):533-541.

Mühlenbeck et al. (1996) "Formation of Hydroxycinnamoylamides and Alpha-Hydroxyacetovanillone in Cell Cultures of *Solanum khasianum*," *Phytochem.* 42(6):1573-1579.

Naganawa et al. (2006) "Further Optimization of Sulfonamide Analogs as EP1 Receptor Antagonists: Synthesis and Evaluation of Bioisosteres fr the carboxylic Acid Group," *Bioorg. Med. Chem.* 14:7121-7137.

Nakagawara et al. (1997) "High Levels of Expression and Nuclear Localization of Interleukin-1 Beta Converting Enzyme (ICE) and CPP32 in Favorable Human Neuroblastomas," *Cancer Res.* 57:4578-4584.

National Center for Biotechnology Information (NCBI) Database of the National Library of Medicine / National Institutes of Health (NIH) website: http://www.ncbi.nlm.nih.gov/ using the Gene database to search for CASP3 (caspase 3, apoptosis-related cysteine protease [Homo sapiens] GeneID: 836 Locus tag: HGNC:1504; MIM: 600636 updated May 15, 2005.

Negrel et al. (1996) "Ether-Linked Ferulic Acid Amides in Natural and Wound Periderms of Potato Tuber," *Phytochem.* 43(6):1195-1199.

Nesterenko et al. (2003) "The Use of pH to Influence Regio- and Chemoselectivity in the Asymmetric Aminohydroxylation of Styrenes," *Org. Lett.* 5(3):281-284.

Nesterenko et al. (Dec. 3, 2003) "Identification from a Combinatorial Library of a Small Molecule that Selectively Induces Apoptosis in Cancer Cells," *J. Am. Chem. Soc.* 125(48):14672-14673.

Newmeyer et al. (Feb. 21, 2003) "Mitochondria: Releasing Power for Life and Unleashing the Machineries of Death," *Cell* 112:481-490.

Nguyen et al. (Jun. 24, 2003) "Direct Activation of the Apoptosis Machinery as a Mechanism to Target Cancer Cells," *Proc. Nat. Acad. Sci. USA* 100:7533-7538.

Nielsen et al. (Apr. 1988) "Glycoamide Esters as Biolabile Prodrugs of Carboxilic Acid Agents: Synthesis, Stability, Bioconversion, and Physicochemical Properties," *J. Pharm. Sci.* 77(4):285-298.

Norgrady (1985) "Pro-Drugs and Soft Drugs," In; *Medicinal Chemistry A Biochemical Approach*, Oxford University Press, New York, pp. 388-392.

O'Donovan et al. (2003) "Caspase 3 in Breast Cancer," *Clin Cancer Res* 9:738-742.

Okada et al. (2004) "Pathways of Apoptotic and Non-Apoptotic Death in Tumour Cells," *Nature Rev. Cancer* 4:592-603.

Oltersdorf et al. (Jun. 2005) "An Inhibitor of Bcl-2 Family Proteins Induces Regression of Solid Tumours," *Nature* 435:677-681.

Oredipe et al. (2003) "Limits of Stimulation of Proliferation and Differentiation of Bone Marrow Cells of Mice Treated with Swainsonine," *Internation. Immunopharm.* 3:1537-1547.

Padhani et al. (2001) "The RECIST (Response Evaluation Criteria in Solid Tumors) Criteria: Implications for Diagnostic Radiologists," *Br. J. Radiol.* 74:983-986.

Paoloni et al. (2008) "Translation of New Cancer Treatments from Pet Dogs to Humans," *Nat Rev Cancer* 8:147-156.

Papadopoulos et al. (Aug. 2006) "The Role of Companion Diagnostics in the Development and use of Mutation-Targeted Cancer Therapies," *Nat Biotechnol* 24(8):985-995.

Patton et al. (2004) "Some Precautions in using Chelatos to Buffer Metals in Biological Solutions," *Cell Calcium* 35:427-431.

Persad et al. (2004) "Overexpression of Caspase-3 in Heptocellular Carcinomas," *Modern Patholo.* 17:861-867.

Peterson et al. (Web Release Aug. 26, 2009) "Procaspase-3 Activation as an Anti-Cancer Strategy: Structure-Activity Relationship of Procaspase-Activating Compound 1 (PAC-1) and its Cellular Co-Localization with Caspase-3," *J. Med. Chem.* 52(18):5721-5731.

Peterson et al. (Web Release Mar. 10, 2009) "PAC-1 Activates Procaspase-3 in Vitro Through Relief of Zinc-Mediated Inhibition," *J. Mol. Biol.* 388:144-158.

Peterson et al. (Web Release Sep. 7, 2010) "Discovery and Canine Preclinical Assessment of a Nontoxic Procaspase-3-Activating Compound," *Cancer Res.* 70(18):7232-7241.

Plowman, J. (1995) "Efficacy of the Quinocarmycins KW2152 and DX-52-1 Against Human Melanoma Lines Growing in Culture and in Mice," *Cancer Res.* 55(4):862-867.

Pop et al. (2003) "Mutations in the Procaspase-3 Dimer Interface Affect the Activity of the Zymogen," *Biochem.* 42:12311-12320.

Prater et al. (2002) "Single-Dose Topical Exposure to the Pyrethroid Insecticide, Permethrin in C57BL/6N Mice: Effects on Thymus and Spleen," *Food Chem. Toxicol.* 40:1863-1873.

Putt et al. (2005) "Direct Quantification of Poly(ADP-ribose) Polymerase (PARP) Activity as a Means to Distinguish Necrotic and Apoptotic Death in Cell and Tissue Samples," *ChemBioChem* 6:53-55.

Putt et al. (Aug. 27, 2006) "Small-Molecule Activation of Procaspase-3 to Caspase-3 as a Personalized Anticancer Strategy," *Nat. Chem. Biol.* 2(10):543-550.

Putt et al. (Mar. 1, 2004) "An Enzymatic Assay for Poly(ADP-ribose) Polymerase-1 (PARP-1_Via the Chemical Quantitation of NAD(+): Application to the High-Throughput Screening of Small Molecules as Potential Inhibitors," *Anal. Biochem.* 326(1):78-86.

Putt et al. (Oct. 15, 2004) "A Nonradiometric, High-Throughput Assay for Poly(ADP-ribose) Glycohydrolase (PARG): Application to Inhibitor Identification and Evaluation." *Anal. Biochem.* 333(2):256-264.

Rassnick et al. (2002) MOPP Chemotherapy for Treatment of Resistant Lymphoma in Dogs: A Retrospective Study of 117 Cases (1989-2000) *J. Vet Intern. Med.* 16:576-580.

Reed et al. (Feb. 2002) "Apoptosis-Based Therapies," *Nat. Rev. Drug Dis.* 1:111-121.

Ren et al. (2008) "Characterization of the in Vivo and in Vitro Metabolic Profile of PAC-a Using Liquid Chromatography-Mass Spectrometry," *J. Chromatogr. B* 876(1):47-53.

Roy et al. (2001) "Maintenance of Caspase-3 Proenzyme Dormancy by an Intrinsic "Safety Catch" Regulatory Tripeptide," *Proc. Nat. Acad. Sci. USA* 98:6132-6137.

Sala et al. (Published online May 5, 2008) "BRAF Silencing by Short Hairpin RNA or Chemical Blockade by PLX4032 Leads to Different Responses in Melanoma and Thyroid Carcinoma Cells," *Mol Cancer Res* 6:751-759.

Salerno et al. (Jan. 2010) Cytostatic Activity of Adenosine Triphosphate-Competitive Kinase Inhibitors in BRAF Mutant Thyroid Carcinoma Cells. *J Clin Endocrinol Metab* 95(1): 450-455.

Satoh et al. (Published online May 26, 2009) "Phase I Study of YM155, a Novel Survivin Suppressant, in Patients with Advanced Solid Tumors," *Clin. Cancer Res.* 15:3872-3880.

Satyamoorthy et al. (May 2001) "No Longer a Molecular Black Box—New Clues to Apoptosis and Drug Resistance in Melanoma," *Trends Mol. Med.* 7:191-194.

Schadendorf et al. (Jan. 1, 1994) "Chemosensitivity Testing of Human Malignant Melanoma. A Retrospective Analysis of Clinical Response and in Vitro Drug Sensitivity," *Cancer* 73:103-108.

Sengupta et al. (1978) "Search for Potential Psychotropic Agents. Part II. N-Benzylidene Derivatives of 4-Arylpiperazine-1-Acetic Acid Hydrazides," *Polish J. Pharm. Pharmacy* 30(1):89-94.

Serrone et al. (2000) "Dacarbazine-Based Chemotherapy for Metastic Melaname: Thirty-Year Experience Overview," *J. Exp. Clin. Cancer Res.* 19:21-34.

Shermolovich et al. (1980) "Reactions of Fuchsone with Dialkyl Hydrogen and Trialkyl Phosphites," *J. Gen. Chem. USSR* 50(4):649-652, 811-815.

Shi, Y. (2002) "Mechanisms of Caspase Activation and Inhibition During Apoptosis," *Mol. Cell* 9:459-470.

(56) References Cited

OTHER PUBLICATIONS

Silverman et al. (2006) "Combinatorial Chemistry and Molecular Diversity Tools for Molecular Diversification and Their Applications in Chemical Biology," *Curr. Opin. Chem. Biol.* 10(3):185-187.
Singh et al. (Jan. 2004) "Sulforaphane Induces Caspase-Mediated Apoptosis in Cultured PC-3 Human Prostate Cancer Cells and Retards Growth of PC-3 Xeonografts in Vivo," *Carcinogenesis* 25(1):83-90.
Slee et al. (Apr. 1, 1996) "Benzyloxycarbonyl-Val-Ala-Asp (OMe) Fluoromethylketone (Z-VAD.FMK) Inhibits Apoptosis by Blocking the Processing of CPP32," *Biochem. J.* 315(1):21-24.
Soengas et al. (2003) "Apoptosis and Melanoma Chemoresistance," *Oncogene* 22:3138-3151.
Soengas et al. (Jan. 11, 2001) "Inactivation of the Apoptosis Effector Apaf-1 in Malignant Melanoma," *Nature* 409:207-211.
Stennicke et al. (1998) "Pro-Caspase-3 Is a Major Physiologic Target of Caspase-8," *J. Biol. Chem.* 273:27084-27090.
Sun et al. (Oct. 2008) "Design of Small-Molecule Peptidic and Nonpeptidic Smac Mimetics," *Acc. Chem. Res.* 41(10):1264-1277.
Sundström et al. (1976) "Establishment and Characterization of a Human Histiocytic Lymphoma Cell Line (U-937)," *Int. J. Cancer* 17:565-577.
Supplementary European Search Report, Corresponding to European Application No. EP 06 77 1588, Completed Jul. 19, 2010.
Supplementary European Search Report, Corresponding to European Application No. EP 10 73 9254, Completed Jul. 25, 2012.
Svingen et al. (2004) "Components of the Cell Death Machine and Drug Sensitivity of the National Cancer Institute Cell Line Panel," *Clin. Cancer Res.* 10:6807-6820.
Tagawa et al. (1985) "Low-Dose Cytosine Arabinoside Regimen Induced a Complete Remission with Normal Karyotypes in a Case with Hypoplastic Acute Myeloid Leukaemia with No. 8-Trisomy: In Vitro and in Vivo Evidence for Normal Haematopoietic Recovery," *Br J Haematol* 60:449-455.
Tomita et al. (Dec. 1990) "A New Screening Method for Melanin Biosynthesis Inhibitors Using *Streptomyces bikiniensis*," *J. Antibiotics* 43(12):1601-1605.
Tovar et al. (Feb. 7, 2006) "Small-Molecule MDM2 Antagonists Reveal Aberrant p53 Signaling in Cancer: Implications for Therapy," *PNAS* 103(6):1888-1893.
Traven et al. (2004) "Protein Hijacking: Key Proteins Held Captive Against Their Will," *Cancer Cell* 5:107-108.
Vassilev et al. (2004) "In Vivo Activation of the p53 Pathway by Small-Molecule Antagonists of MDM2," *Science* 303:844-848.
Vail et al., (2004) "Vetrinary Co-operative Oncology Group—Common Terminology Criteria for Adverse Events (VCOG-CTCAE) Following Chemotherapy of Biological Antineoplastic Therapy in Dogs and Cats v1.0," *Vet Comp. Oncol.* 2:195-213.
Vichai et al. (Published online Aug. 17, 2006) "Sulforhodamine B Colorimetric Assay for Cytotoxicity Screening," *Nat. Protocols* 1(3):1112-1116.
Vogelstein et al. (2001) "Achilles' Heel of Cancer," *Nature* 412:865-866.
Vogelstein et al. (Aug. 2004) "Cancer Genes and the Pathways they Control," *Nat Med* 10(8):789-799.
Wadsworth et al. (1973) "Ethyl Cyclohexylideneacetate," *Organic Synthesis Coll.* 5:547, 45:44.
Wajant et al. (2003) "Targeting the FLICE Inhibitory Protein (FLIP) in Cancer Therapy," *Mol. Interv.* 3:124-127.
Wang et al. (2000) "Structure-Based Discovery of an Organic Compound that Binds Bcl-2 Protein and Induces Apoptosis of Tumor Cells," *Proc. Natl. Acad. Sci.* 97:7124-7129.
Wright et al. (Oct. 6, 1997) "Activation of CPP32-Like Proteases is Not Sufficient to Trigger Apoptosis: Inhibition of Apoptosis by Agents that Suppress Activation of AP24, but not CPP32-Like Activity," *J. Exp. Med.* 186(7):1107-1117.
Yamaura et al. (Feb. 2002) "Inhibition of the Antibody Production by Acetaminophen Independent of Liver Injury in Mice," *Bio. Pharm. Bull.* 25(2):201-205.
Young et al. (1956) "The Use of Phosphorous Acid Chlorides in Peptide Synthesis," *J. Am. Chem. Soc.* 78:2126-2131.
Zalupski et al. (Jul. 3, 1991) "Phase III Comparison of Doxorubicin and Dacarbazine Given by Bolus Versus Infusion in Patients With Soft-Tissue Sarcomas: A Southwest Oncology Group Study," *J. Natl. Cancer Inst.* 83(13):926-932.
Zornig et al. (2001) "Apoptosis Regulators and their Role in Tumorigenesis," *Biochim. Biophys. Acta* 1551:F1-F37, abstract only.
Dorn et al. (1970) "The Epidemiology of Canine Leukemia and Lymphoma," *Bibl Haematol.* :403-415.
Franklin et al. (2005) "Zinc and Zinc Transporters in Normal Prostate and the Pathogenesis of Prostate Cancer," *Front. Biosci.* 10:2230-2239.
Kahl, B. (2008) "Chemotherapy Combinations with Monoclonal Antibodies in non-Hodgkin's Lymphoma," *Semin Hematol* 45:90-94.
Wang et al. (Jan. 2002) "CPP32 Expression and its Significance in Multidrug-Resistant Tumor Cells and their Parent Cells," *Di Yi Jun Yi Da Xue Xue Bao* 22(1):32-34.

* cited by examiner

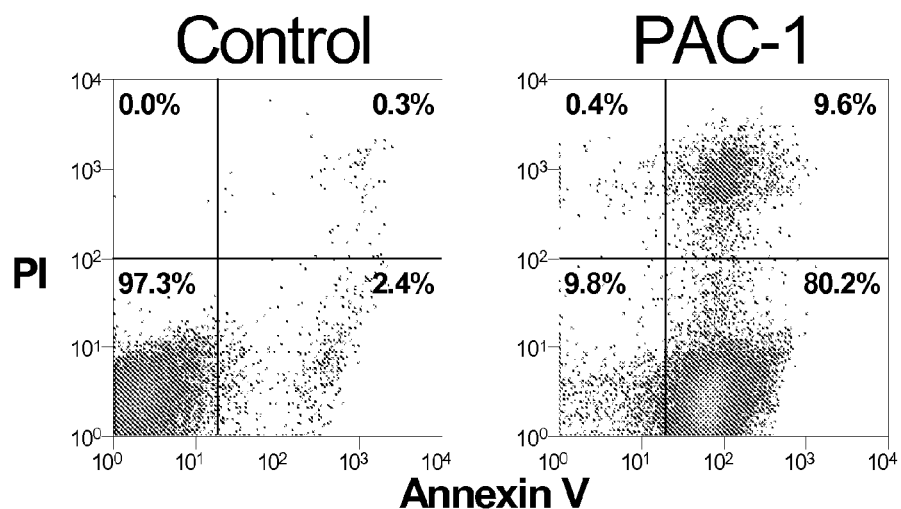
FIG. 3A (color)
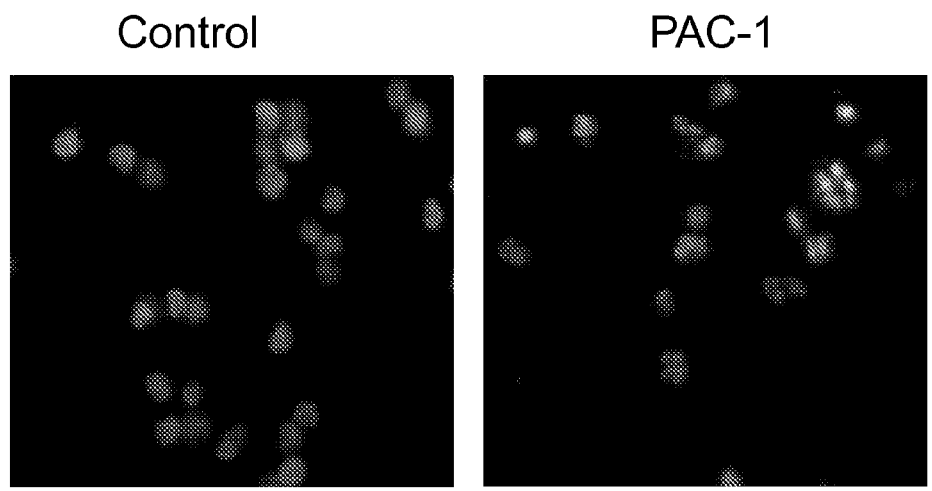
FIG. 3B (color)

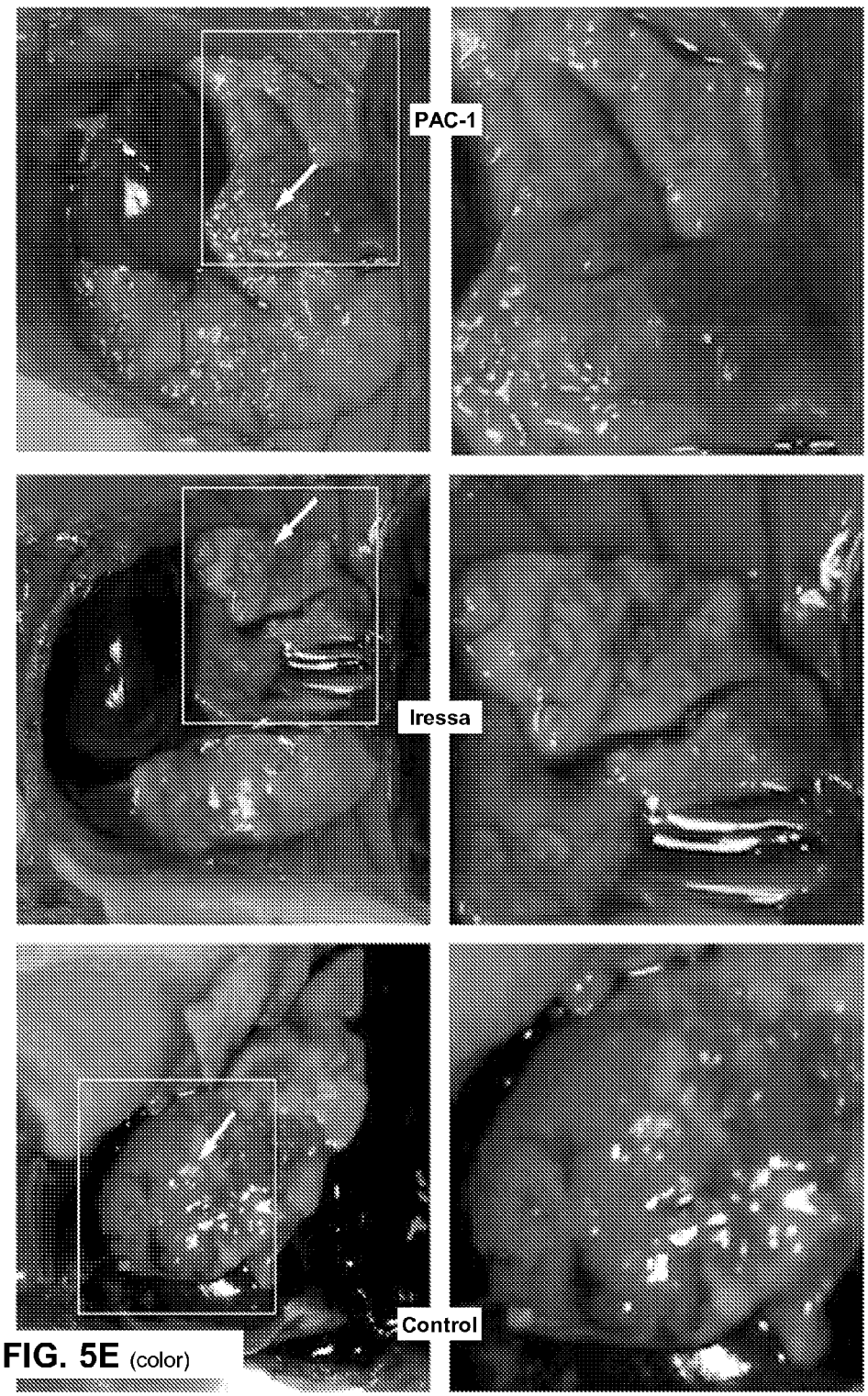
FIG. 5E (color)

Homo sapiens caspase 3 (CASP3), Accession No. NM_004346

```
   1  acatctcccg gcggcgggcc gcggaagcag tgcagacgcg gctcctagcg gatgggtgct
  61  attgtgaggc ggttgtagaa gagtttcgtg agtgctcgca gctcatacct gtggctgtgt
 121  atccgtggcc acagctggtt ggcgtcgcct tgaaatccca ggccgtgagg agttagcgag
 181  ccctgctcac actcggcgct ctggttttcg gtgggtgtgc cctgcacctg cctcttcccc
 241  cattctcatt aataaaggta tccatggaga acactgaaaa ctcagtggat tcaaaatcca
 301  ttaaaaattt ggaaccaaag atcatacatg gaagcgaatc aatggactct ggaatatccc
 361  tggacaacag ttataaaatg gattatcctg agatgggttt atgtataata attaataata
 421  agaattttca taaaagcact ggaatgacat ctcggtctgg tacagatgtc gatgcagcaa
 481  acctcaggga acattcaga aacttgaaat atgaagtcag gaataaaaat gatcttacac
 541  gtgaagaaat tgtggaattg atgcgtgatg tttctaaaga agatcacagc aaaaggagca
 601  gttttgtttg tgtgcttctg agccatggtg aagaaggaat aattttggac acaaatggac
 661  ctgttgacct gaaaaaata acaaactttt tcagagggga tcgttgtaga agtctaactg
 721  gaaaacccaa acttttcatt attcaggcct gccgtggtac agaactggac tgtggcattg
 781  agacagacag tggtgttgat gatgacatgg cgtgtcataa ataccagtg gaggccgact
 841  tcttgtatgc atactccaca gcacctggtt attattcttg gcgaaattca aaggatggct
 901  cctggttcat ccagtcgctt tgtgccatgc tgaaacagta tgccgacaag cttgaattta
 961  tgcacattct tacccgggtt aaccgaaagg tggcaacaga atttgagtcc ttttcctttg
1021  acgctacttt tcatgcaaag aaacagattc catgtattgt tccatgctc acaaaagaac
1081  tctatttta tcactaaaga aatggttggt tggtggtttt tttagtttg tatgccaagt
1141  gagaagatgg tatatttggt actgtatttc cctctcattt tgacctactc tcatgctgca
1201  gagggtactt taagacatac tccttccatc aaatagaacc actatgaagc tacctcaaac
1261  ttccagtcag gtagttgcaa ttgaattaaa ttaggaataa ataaaaatgg atactggtgc
1321  agtcattatg agaggcaatg attgttaatt tacagctttc atgattagca agttacagtg
1381  atgctgtgct atgaattttc aagtaattgt gaaaagtta acattgaag taatgaattt
1441  ttatgatatt ccccccactt aagactgtgt attctagttt tgtcaaactg tagaaatgat
1501  gatgtggaag aacttaggca tctgtgggca tggtcaaagg ctcaaacctt tatttagaa
1561  ttgatataca cggatgactt aactgcattt ttagaccatt tatctgggat tatggttttg
1621  tgatgttgt cctgaacact tttgttgtaa aaaataata ataatgtta atattgagaa
1681  agaaactaat attttatgtg agagaaagtg tgagcaaact aacttgactt taaggctaa
1741  aacttaacat tcatagaggg gtggagtttt aactgtaagg tgctacaatg ccctggatc
1801  taccagcata aatatcttct gatttgtccc tatgcatatc agttgagctt catataccag
1861  caatatatct gaagagctat tatataaaa ccccaaactg ttgattatta gccaggtaat
1921  gtgaataaat tctataggaa catatgaaaa tacaacttaa ataataaaca gtggaatata
1981  aggaaagcaa taatgaatg ggctgagctg cctgtaactt gagagtagat ggtttgagcc
2041  tgagcagaga catgactcag cctgttccat gaaggcagag ccatggacca cgcaggaagg
2101  gcctacagcc catttctcca tacgcactgg tatgtgtgga tgatgctgcc agggcgccat
2161  cgccaagtaa gaaagtgaag caaatcagaa acttgtgaag tggaaatgtt ctaaaggtgg
2221  tgaggcaata aaaatcatag tactctttgt agcaaaattc ttaagtatgt tatttctgt
2281  tgaagtttac aatcaaagga aatagtaat gttttatact gtttactgaa agaaaaagac
2341  ctatgagcac ataggactct agacggcatc cagccggagg ccagagctga gccctcagcc
2401  cggaggcag gctccaggcc tcagcaggt cggagccgtc actgcaccaa gtctcactgg
2461  ctgtcagtat gacatttcac gggagatttc ttgttgctca aaaatgagc tcgcatttgt
2521  caatgacagt ttcttttttc ttactagacc tgtaactttt gtaaatacac atagcatgta
2581  atggtatctt aaagtgtgtt tctatgtgac aattttgtac aaatttgtta ttttccattt
2641  ttatttcaaa atatacattc aaacttaaaa ttaaaaaaaa aaaaaaaa
```

FIG. 9

```
Homo sapiens caspase 7 (CASP7), Accession No. NM_001227
    1 ctcccgcgcg cgggctcaac tttgtagagc gaggggccaa cttggcagag cgcgcggcca
   61 gctttgcaga gagcgccctc cagggactat gcgtgcgggg acacgggtcg ctttgggctc
  121 ttccacccct gcggagcgca ctaccccgag ccaggggcgg tgcaagcccc gcccggccct
  181 acccagggcg gctcctccct ccgcagcgcc gagactttta gtttcgcttt cgctaaaggg
  241 gccccagacc cttgctgcgg agcgacggag agagactgtg ccagtcccag ccgccctacc
  301 gccgtgggaa cgatggcaga tgatcagggc tgtattgaag agcagggggt tgaggattca
  361 gcaaatgaag attcagtgga tgctaagcca gaccggtcct cgtttgtacc gtccctcttc
  421 agtaagaaga agaaaaatgt caccatgcga tccatcaaga ccaccccggga ccgagtgcct
  481 acatatcagt acaacatgaa ttttgaaaag ctgggcaaat gcatcataat aaacaacaag
  541 aactttgata aagtgacagg tatgggcgtt cgaaacggaa cagacaaaga tgccgaggcg
  601 ctcttcaagt gcttccgaag cctgggtttt gacgtgattg tctataatga ctgctcttgt
  661 gccaagatgc aagatctgct taaaaaagct tctgaagagg accatacaaa tgccgcctgc
  721 ttcgcctgca tcctcttaag ccatggagaa gaaaatgtaa tttatgggaa agatggtgtc
  781 acaccaataa aggatttgac agcccacttt agggggggata gatgcaaaac cctttttagag
  841 aaacccaaac tcttcttcat tcaggcttgc cgagggaccg agcttgatga tggcatccag
  901 gccgactcgg ggcccatcaa tgacacagat gctaatcctc gatacaagat cccagtggaa
  961 gctgacttcc tcttcgccta ttccacggtt ccaggctatt actcgtggag gagcccagga
 1021 agaggctcct ggtttgtgca agccctctgc tccatcctgg aggagcacgg aaaagacctg
 1081 gaaatcatgc agatcctcac cagggtgaat gacagagttg ccaggcactt tgagtctcag
 1141 tctgatgacc cacacttcca tgagaagaag cagatcccct gtgtggtctc catgctcacc
 1201 aaggaactct acttcagtca atagccatat cagggtgtaca ttctagctga agcaatgg
 1261 gtcactcatt aatgaatcac attttttttat gctcttgaaa tattcagaaa ttctccagga
 1321 ttttaatttc aggaaaatgt attgattcaa cagggaagaa actttctggt gctgtctttt
 1381 gttctctgaa ttttcagaga cttttttttat aatgttattc atttggtgac tgtgtaactt
 1441 tctcttaaga ttaattttct ctttgtatgt ctgttacctt gttaatagac ttaatacatg
 1501 caacagaagt gacttctgga gaaagctcat ggctgtgtcc actgcaattg gtggtaacag
 1561 tggtagagtc atgtttgcac ttggcaaaaa gaatcccaat gtttgacaaa acacagccaa
 1621 ggggatattt actgctcttt attgcagaat gtgggtattg agtgtgatttt gaatgatttt
 1681 tcattggctt agggcagatt ttcatgcaaa agttctcata tgagttagag gagaaaaagc
 1741 ttaatgattc tgatatgtat ccatcaggat ccagtctgga aaacagaaac cattctaggt
 1801 gtttcaacag agggagttta atacaggaaa ttgacttaca tagatgataa aagagaagcc
 1861 aaacagcaag aagctgttac cacacccagg gctatgagga taatgggaag aggtttggtt
 1921 tcctgtgtcc agtagtggga tcatccagag gagctggaac catggtgggg gctgcctagt
 1981 gggagttagg accaccaatg gattgtgaa aatggagcca tgacaagaac aaagccactg
 2041 actgagatgg agtgagctga gacagataag agaatacctt ggtctcacct atcctgccct
 2101 cacatcttcc accagcacct tactgcccag gcctatctgg aagccacctc accaaggacc
 2161 ttggaagagc aagggacagt gaggcaggag aagaacaaga atggatgta agcctggccc
 2221 ataatgtgaa cataagtaat cactaatgct caacaattta tccattcaat catttattca
 2281 ttgggttgtc agatagtcta tgtatgtgta aaacaatctg ttttggcttt atgtgcaaaa
 2341 tctgttatag ctttaaaata tatctggaac tttttagatt attccaagcc ttatttgag
 2401 taaatatttg ttacttttag ttctataagt gaggaagagt ttatggcaaa gattttttgc
 2461 actttgtttt caagatggtg ttatcttttg aattcttgat aaatgactgt ttttttctgc
 2521 ctaatagtaa ctggttaaaa aacaaatgtt catatttatt gattaaaaat gtggttgctt
 2581 aattcctaaa aaaaaaaaaa aaaaa
```

FIG. 10

SEQUENCE LISTING

```
<160> NUMBER OF SEQ ID NOS: 27

<210> SEQ ID NO 1
<211> LENGTH: 834
<212> TYPE: DNA
<213> ORGANISM: Homo sapiens
<220> FEATURE:
<221> NAME/KEY: CDS
<222> LOCATION: (1)..(834)
<223> OTHER INFORMATION: Procaspase-3; with amino acid DDD wild-type
      safety catch sequence (ACCESSION Number NM_004346)

<400> SEQUENCE: 1 atg gag aac act gaa aac tca gtg gat tca aaa tcc att aaa aat ttg      48
Met Glu Asn Thr Glu Asn Ser Val Asp Ser Lys Ser Ile Lys Asn Leu
1               5                   10                  15 gaa cca aag atc ata cat gga agc gaa tca atg gac tct gga ata tcc      96
Glu Pro Lys Ile Ile His Gly Ser Glu Ser Met Asp Ser Gly Ile Ser
            20                  25                  30 ctg gac aac agt tat aaa atg gat tat cct gag atg ggt tta tgt ata     144
Leu Asp Asn Ser Tyr Lys Met Asp Tyr Pro Glu Met Gly Leu Cys Ile
        35                  40                  45 ata att aat aat aag aat ttt cat aaa agc act gga atg aca tct cgg     192
Ile Ile Asn Asn Lys Asn Phe His Lys Ser Thr Gly Met Thr Ser Arg
```

```
                  50                  55                  60
tct ggt aca gat gtc gat gca gca aac ctc agg gaa aca ttc aga aac      240
Ser Gly Thr Asp Val Asp Ala Ala Asn Leu Arg Glu Thr Phe Arg Asn
 65                  70                  75                  80 ttg aaa tat gaa gtc agg aat aaa aat gat ctt aca cgt gaa gaa att      288
Leu Lys Tyr Glu Val Arg Asn Lys Asn Asp Leu Thr Arg Glu Glu Ile
                 85                  90                  95 gtg gaa ttg atg cgt gat gtt tct aaa gaa gat cac agc aaa agg agc      336
Val Glu Leu Met Arg Asp Val Ser Lys Glu Asp His Ser Lys Arg Ser
            100                 105                 110 agt ttt gtt tgt gtg ctt ctg agc cat ggt gaa gaa gga ata att ttt      384
Ser Phe Val Cys Val Leu Leu Ser His Gly Glu Glu Gly Ile Ile Phe
        115                 120                 125 gga aca aat gga cct gtt gac ctg aaa aaa ata aca aac ttt ttc aga      432
Gly Thr Asn Gly Pro Val Asp Leu Lys Lys Ile Thr Asn Phe Phe Arg
    130                 135                 140 ggg gat cgt tgt aga agt cta act gga aaa ccc aaa ctt ttc att att      480
Gly Asp Arg Cys Arg Ser Leu Thr Gly Lys Pro Lys Leu Phe Ile Ile
145                 150                 155                 160 cag gcc tgc cgt ggt aca gaa ctg gac tgt ggc att gag aca gac agt      528
Gln Ala Cys Arg Gly Thr Glu Leu Asp Cys Gly Ile Glu Thr Asp Ser
                165                 170                 175 ggt gtt gat gat gac atg gcg tgt cat aaa ata cca gtg gag gcc gac      576
Gly Val Asp Asp Asp Met Ala Cys His Lys Ile Pro Val Glu Ala Asp
            180                 185                 190 ttc ttg tat gca tac tcc aca gca cct ggt tat tat tct tgg cga aat      624
Phe Leu Tyr Ala Tyr Ser Thr Ala Pro Gly Tyr Tyr Ser Trp Arg Asn
        195                 200                 205 tca aag gat ggc tcc tgg ttc atc cag tcg ctt tgt gcc atg ctg aaa      672
Ser Lys Asp Gly Ser Trp Phe Ile Gln Ser Leu Cys Ala Met Leu Lys
    210                 215                 220 cag tat gcc gac aag ctt gaa ttt atg cac att ctt acc cgg gtt aac      720
Gln Tyr Ala Asp Lys Leu Glu Phe Met His Ile Leu Thr Arg Val Asn
225                 230                 235                 240 cga aag gtg gca aca gaa ttt gag tcc ttt tcc ttt gac gct act ttt      768
Arg Lys Val Ala Thr Glu Phe Glu Ser Phe Ser Phe Asp Ala Thr Phe
                245                 250                 255 cat gca aag aaa cag att cca tgt att gtt tcc atg ctc aca aaa gaa      816
His Ala Lys Lys Gln Ile Pro Cys Ile Val Ser Met Leu Thr Lys Glu
            260                 265                 270 ctc tat ttt tat cac taa                                              834
Leu Tyr Phe Tyr His
        275

<210> SEQ ID NO 2
<211> LENGTH: 277
<212> TYPE: PRT
<213> ORGANISM: Homo sapiens

<400> SEQUENCE: 2

Met Glu Asn Thr Glu Asn Ser Val Asp Ser Lys Ser Ile Lys Asn Leu
 1               5                  10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
 65                  70                  75                  80
```

-continued

Leu Lys Tyr Glu Val Arg Asn Lys Asn Asp Leu Thr Arg Glu Glu Ile
            85                  90                  95

Val Glu Leu Met Arg Asp Val Ser Lys Glu Asp His Ser Lys Arg Ser
        100                 105                 110

Ser Phe Val Cys Val Leu Leu Ser His Gly Glu Gly Ile Ile Phe
    115                 120                 125

Gly Thr Asn Gly Pro Val Asp Leu Lys Lys Ile Thr Asn Phe Phe Arg
130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275

```
<210> SEQ ID NO 3
<211> LENGTH: 1326
<212> TYPE: DNA
<213> ORGANISM: Homo sapiens
<220> FEATURE:
<221> NAME/KEY: CDS
<222> LOCATION: (50)..(880)
<223> OTHER INFORMATION: Procaspase-3; with amino acid DDD to ADD safety
      catch mutant sequence
<220> FEATURE:
<221> NAME/KEY: misc_feature
<222> LOCATION: (934)..(934)
<223> OTHER INFORMATION: n is a, c, g, t or u
<220> FEATURE:
<221> NAME/KEY: misc_feature
<222> LOCATION: (939)..(939)
<223> OTHER INFORMATION: n is a, c, g, t or u
<220> FEATURE:
<221> NAME/KEY: misc_feature
<222> LOCATION: (954)..(954)
<223> OTHER INFORMATION: n is a, c, g, t or u
<220> FEATURE:
<221> NAME/KEY: misc_feature
<222> LOCATION: (982)..(982)
<223> OTHER INFORMATION: n is a, c, g, t or u
<220> FEATURE:
<221> NAME/KEY: misc_feature
<222> LOCATION: (988)..(988)
<223> OTHER INFORMATION: n is a, c, g, t or u
<220> FEATURE:
<221> NAME/KEY: misc_feature
<222> LOCATION: (1000)..(1000)
<223> OTHER INFORMATION: n is a, c, g, t or u
<220> FEATURE:
<221> NAME/KEY: misc_feature
<222> LOCATION: (1024)..(1024)
<223> OTHER INFORMATION: n is a, c, g, t or u
<220> FEATURE:
<221> NAME/KEY: misc_feature
```

-continued

```
<222> LOCATION: (1036)..(1036)
<223> OTHER INFORMATION: n is a, c, g, t or u
<220> FEATURE:
<221> NAME/KEY: misc_feature
<222> LOCATION: (1045)..(1045)
<223> OTHER INFORMATION: n is a, c, g, t or u
<220> FEATURE:
<221> NAME/KEY: misc_feature
<222> LOCATION: (1051)..(1051)
<223> OTHER INFORMATION: n is a, c, g, t or u
<220> FEATURE:
<221> NAME/KEY: misc_feature
<222> LOCATION: (1053)..(1053)
<223> OTHER INFORMATION: n is a, c, g, t or u
<220> FEATURE:
<221> NAME/KEY: misc_feature
<222> LOCATION: (1063)..(1063)
<223> OTHER INFORMATION: n is a, c, g, t or u
<220> FEATURE:
<221> NAME/KEY: misc_feature
<222> LOCATION: (1071)..(1071)
<223> OTHER INFORMATION: n is a, c, g, t or u
<220> FEATURE:
<221> NAME/KEY: misc_feature
<222> LOCATION: (1075)..(1075)
<223> OTHER INFORMATION: n is a, c, g, t or u
<220> FEATURE:
<221> NAME/KEY: misc_feature
<222> LOCATION: (1079)..(1079)
<223> OTHER INFORMATION: n is a, c, g, t or u
<220> FEATURE:
<221> NAME/KEY: misc_feature
<222> LOCATION: (1086)..(1086)
<223> OTHER INFORMATION: n is a, c, g, t or u
<220> FEATURE:
<221> NAME/KEY: misc_feature
<222> LOCATION: (1093)..(1093)
<223> OTHER INFORMATION: n is a, c, g, t or u
<220> FEATURE:
<221> NAME/KEY: misc_feature
<222> LOCATION: (1095)..(1095)
<223> OTHER INFORMATION: n is a, c, g, t or u
<220> FEATURE:
<221> NAME/KEY: misc_feature
<222> LOCATION: (1100)..(1100)
<223> OTHER INFORMATION: n is a, c, g, t or u
<220> FEATURE:
<221> NAME/KEY: misc_feature
<222> LOCATION: (1104)..(1104)
<223> OTHER INFORMATION: n is a, c, g, t or u
<220> FEATURE:
<221> NAME/KEY: misc_feature
<222> LOCATION: (1106)..(1106)
<223> OTHER INFORMATION: n is a, c, g, t or u
<220> FEATURE:
<221> NAME/KEY: misc_feature
<222> LOCATION: (1125)..(1125)
<223> OTHER INFORMATION: n is a, c, g, t or u
<220> FEATURE:
<221> NAME/KEY: misc_feature
<222> LOCATION: (1140)..(1140)
<223> OTHER INFORMATION: n is a, c, g, t or u
<220> FEATURE:
<221> NAME/KEY: misc_feature
<222> LOCATION: (1146)..(1146)
<223> OTHER INFORMATION: n is a, c, g, t or u
<220> FEATURE:
<221> NAME/KEY: misc_feature
<222> LOCATION: (1149)..(1150)
<223> OTHER INFORMATION: n is a, c, g, t or u
<220> FEATURE:
<221> NAME/KEY: misc_feature
<222> LOCATION: (1155)..(1155)
<223> OTHER INFORMATION: n is a, c, g, t or u
<220> FEATURE:
<221> NAME/KEY: misc_feature
<222> LOCATION: (1157)..(1157)
<223> OTHER INFORMATION: n is a, c, g, t or u
<220> FEATURE:
<221> NAME/KEY: misc_feature
```

```
<222> LOCATION: (1159)..(1159)
<223> OTHER INFORMATION: n is a, c, g, t or u
<220> FEATURE:
<221> NAME/KEY: misc_feature
<222> LOCATION: (1190)..(1190)
<223> OTHER INFORMATION: n is a, c, g, t or u
<220> FEATURE:
<221> NAME/KEY: misc_feature
<222> LOCATION: (1199)..(1200)
<223> OTHER INFORMATION: n is a, c, g, t or u
<220> FEATURE:
<221> NAME/KEY: misc_feature
<222> LOCATION: (1209)..(1209)
<223> OTHER INFORMATION: n is a, c, g, t or u
<220> FEATURE:
<221> NAME/KEY: misc_feature
<222> LOCATION: (1212)..(1212)
<223> OTHER INFORMATION: n is a, c, g, t or u
<220> FEATURE:
<221> NAME/KEY: misc_feature
<222> LOCATION: (1223)..(1224)
<223> OTHER INFORMATION: n is a, c, g, t or u
<220> FEATURE:
<221> NAME/KEY: misc_feature
<222> LOCATION: (1233)..(1233)
<223> OTHER INFORMATION: n is a, c, g, t or u
<220> FEATURE:
<221> NAME/KEY: misc_feature
<222> LOCATION: (1235)..(1235)
<223> OTHER INFORMATION: n is a, c, g, t or u
<220> FEATURE:
<221> NAME/KEY: misc_feature
<222> LOCATION: (1238)..(1238)
<223> OTHER INFORMATION: n is a, c, g, t or u
<220> FEATURE:
<221> NAME/KEY: misc_feature
<222> LOCATION: (1241)..(1241)
<223> OTHER INFORMATION: n is a, c, g, t or u
<220> FEATURE:
<221> NAME/KEY: misc_feature
<222> LOCATION: (1246)..(1246)
<223> OTHER INFORMATION: n is a, c, g, t or u
<220> FEATURE:
<221> NAME/KEY: misc_feature
<222> LOCATION: (1256)..(1256)
<223> OTHER INFORMATION: n is a, c, g, t or u
<220> FEATURE:
<221> NAME/KEY: misc_feature
<222> LOCATION: (1259)..(1259)
<223> OTHER INFORMATION: n is a, c, g, t or u
<220> FEATURE:
<221> NAME/KEY: misc_feature
<222> LOCATION: (1262)..(1262)
<223> OTHER INFORMATION: n is a, c, g, t or u
<220> FEATURE:
<221> NAME/KEY: misc_feature
<222> LOCATION: (1273)..(1273)
<223> OTHER INFORMATION: n is a, c, g, t or u
<220> FEATURE:
<221> NAME/KEY: misc_feature
<222> LOCATION: (1276)..(1276)
<223> OTHER INFORMATION: n is a, c, g, t or u
<220> FEATURE:
<221> NAME/KEY: misc_feature
<222> LOCATION: (1282)..(1282)
<223> OTHER INFORMATION: n is a, c, g, t or u
<220> FEATURE:
<221> NAME/KEY: misc_feature
<222> LOCATION: (1285)..(1285)
<223> OTHER INFORMATION: n is a, c, g, t or u
<220> FEATURE:
<221> NAME/KEY: misc_feature
<222> LOCATION: (1288)..(1288)
<223> OTHER INFORMATION: n is a, c, g, t or u
<220> FEATURE:
<221> NAME/KEY: misc_feature
<222> LOCATION: (1294)..(1294)
<223> OTHER INFORMATION: n is a, c, g, t or u
<220> FEATURE:
<221> NAME/KEY: misc_feature
```

-continued

```
<222> LOCATION: (1299)..(1299)
<223> OTHER INFORMATION: n is a, c, g, t or u
<220> FEATURE:
<221> NAME/KEY: misc_feature
<222> LOCATION: (1302)..(1302)
<223> OTHER INFORMATION: n is a, c, g, t or u
<220> FEATURE:
<221> NAME/KEY: misc_feature
<222> LOCATION: (1306)..(1306)
<223> OTHER INFORMATION: n is a, c, g, t or u

<400> SEQUENCE: 3
gtacattccc tctgaataat tttgtttact ttaagaagga gatatacat atg gag aac        58
                                                       Met Glu Asn
                                                         1 act gaa aac tca gtg gat tca aaa tcc att aaa aat ttg gaa cca aag         106
Thr Glu Asn Ser Val Asp Ser Lys Ser Ile Lys Asn Leu Glu Pro Lys
      5                  10                  15 atc ata cat gga agc gaa tca atg gac tct gga ata tcc ctg gac aac         154
Ile Ile His Gly Ser Glu Ser Met Asp Ser Gly Ile Ser Leu Asp Asn
 20                  25                  30                  35 agt tat aaa atg gat tat cct gag atg ggt tta tgt ata ata att aat         202
Ser Tyr Lys Met Asp Tyr Pro Glu Met Gly Leu Cys Ile Ile Ile Asn
              40                  45                  50 aat aag aat ttt cat aaa agc act gga atg aca tct cgg tct ggt aca         250
Asn Lys Asn Phe His Lys Ser Thr Gly Met Thr Ser Arg Ser Gly Thr
         55                  60                  65 gat gtc gat gca gca aac ctc agg gaa aca ttc aga aac ttg aaa tat         298
Asp Val Asp Ala Ala Asn Leu Arg Glu Thr Phe Arg Asn Leu Lys Tyr
     70                  75                  80 gaa gtc agg aat aaa aat gat ctt aca cgt gaa gaa att gtg gaa ttg         346
Glu Val Arg Asn Lys Asn Asp Leu Thr Arg Glu Glu Ile Val Glu Leu
 85                  90                  95 atg cgt gat gtt tct aaa gaa gat cac agc aaa agg agc agt ttt gtt         394
Met Arg Asp Val Ser Lys Glu Asp His Ser Lys Arg Ser Ser Phe Val
100                 105                 110                 115 tgt gtg ctt ctg agc cat ggt gaa gaa gga ata att ttt gga aca aat         442
Cys Val Leu Leu Ser His Gly Glu Glu Gly Ile Ile Phe Gly Thr Asn
                120                 125                 130 gga cct gtt gac ctg aaa aaa ata aca aac ttt ttc aga ggg gat cgt         490
Gly Pro Val Asp Leu Lys Lys Ile Thr Asn Phe Phe Arg Gly Asp Arg
            135                 140                 145 tgt aga agt cta act gga aaa ccc aaa ctt ttc att att cag gcc tgc         538
Cys Arg Ser Leu Thr Gly Lys Pro Lys Leu Phe Ile Ile Gln Ala Cys
        150                 155                 160 cgt ggt aca gaa ctg gac tgt ggc att gag aca gac agt ggt gtt gcg         586
Arg Gly Thr Glu Leu Asp Cys Gly Ile Glu Thr Asp Ser Gly Val Ala
    165                 170                 175 gat gac atg gcg tgt cat aaa ata cca gtg gag gcc gac ttc ttg tat         634
Asp Asp Met Ala Cys His Lys Ile Pro Val Glu Ala Asp Phe Leu Tyr
180                 185                 190                 195 gca tac tcc aca gca cct ggt tat tat tct tgg cga aat tca aag gat         682
Ala Tyr Ser Thr Ala Pro Gly Tyr Tyr Ser Trp Arg Asn Ser Lys Asp
                200                 205                 210 ggc tcc tgg ttc atc cag tcg ctt tgt gcc atg ctg aaa cag tat gcc         730
Gly Ser Trp Phe Ile Gln Ser Leu Cys Ala Met Leu Lys Gln Tyr Ala
            215                 220                 225 gac aag ctt gaa ttt atg cac att ctt acc cgg gtt aac cga aag gtg         778
Asp Lys Leu Glu Phe Met His Ile Leu Thr Arg Val Asn Arg Lys Val
        230                 235                 240 gca aca gaa ttt gag tcc ttt tcc ttt gac gct act ttt cat gca aag         826
Ala Thr Glu Phe Glu Ser Phe Ser Phe Asp Ala Thr Phe His Ala Lys
    245                 250                 255
```

```
aaa cag att cca tgt att gtt tcc atg ctc aca aaa gaa ctc tat ttt      874
Lys Gln Ile Pro Cys Ile Val Ser Met Leu Thr Lys Glu Leu Tyr Phe
260             265                 270                 275 tat cac ctcgagcacc accaccacca ccactgagat ccggctgcta caagccgaaa        930
Tyr His gganctgant tggctgctgc cccnctgacc atactacata ccccctgggg cnctaacngg     990 tctgggggn ttttttgctga aggagacttt tccngatggc aatggnaccc cctgnccgcc     1050
ntnacccggc ggnggggtt nccnacgng acctancttg ccngncctan cccncncttc       1110
cttttccttc ttccnccgtt ccggttcccn cagctnaann ggggncntng gtccattggc     1170 ttcgccccc caaactgttn ggggtccnn ggcccccna angtttccct tanngacccc        1230
ttnanggnct ntcccngacc ccccncccnt tnttttaagg tcnccnccg gnaanggnta      1290 aatnccttna ancccntggg ttgggggccc tttttt                              1326

<210> SEQ ID NO 4
<211> LENGTH: 277
<212> TYPE: PRT
<213> ORGANISM: Homo sapiens

<400> SEQUENCE: 4

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Ala Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270
```

Leu Tyr Phe Tyr His
    275

<210> SEQ ID NO 5
<211> LENGTH: 1398
<212> TYPE: DNA
<213> ORGANISM: Homo sapiens
<220> FEATURE:
<221> NAME/KEY: CDS
<222> LOCATION: (51)..(881)
<223> OTHER INFORMATION: Procaspase-3; with amino acid DDD to DAD safety
      catch mutant sequence
<220> FEATURE:
<221> NAME/KEY: misc_feature
<222> LOCATION: (923)..(923)
<223> OTHER INFORMATION: n is a, c, g, t or u
<220> FEATURE:
<221> NAME/KEY: misc_feature
<222> LOCATION: (933)..(933)
<223> OTHER INFORMATION: n is a, c, g, t or u
<220> FEATURE:
<221> NAME/KEY: misc_feature
<222> LOCATION: (942)..(942)
<223> OTHER INFORMATION: n is a, c, g, t or u
<220> FEATURE:
<221> NAME/KEY: misc_feature
<222> LOCATION: (963)..(963)
<223> OTHER INFORMATION: n is a, c, g, t or u
<220> FEATURE:
<221> NAME/KEY: misc_feature
<222> LOCATION: (978)..(978)
<223> OTHER INFORMATION: n is a, c, g, t or u
<220> FEATURE:
<221> NAME/KEY: misc_feature
<222> LOCATION: (991)..(991)
<223> OTHER INFORMATION: n is a, c, g, t or u
<220> FEATURE:
<221> NAME/KEY: misc_feature
<222> LOCATION: (994)..(994)
<223> OTHER INFORMATION: n is a, c, g, t or u
<220> FEATURE:
<221> NAME/KEY: misc_feature
<222> LOCATION: (1022)..(1022)
<223> OTHER INFORMATION: n is a, c, g, t or u
<220> FEATURE:
<221> NAME/KEY: misc_feature
<222> LOCATION: (1031)..(1031)
<223> OTHER INFORMATION: n is a, c, g, t or u
<220> FEATURE:
<221> NAME/KEY: misc_feature
<222> LOCATION: (1033)..(1033)
<223> OTHER INFORMATION: n is a, c, g, t or u
<220> FEATURE:
<221> NAME/KEY: misc_feature
<222> LOCATION: (1045)..(1045)
<223> OTHER INFORMATION: n is a, c, g, t or u
<220> FEATURE:
<221> NAME/KEY: misc_feature
<222> LOCATION: (1047)..(1047)
<223> OTHER INFORMATION: n is a, c, g, t or u
<220> FEATURE:
<221> NAME/KEY: misc_feature
<222> LOCATION: (1061)..(1061)
<223> OTHER INFORMATION: n is a, c, g, t or u
<220> FEATURE:
<221> NAME/KEY: misc_feature
<222> LOCATION: (1067)..(1067)
<223> OTHER INFORMATION: n is a, c, g, t or u
<220> FEATURE:
<221> NAME/KEY: misc_feature
<222> LOCATION: (1069)..(1069)
<223> OTHER INFORMATION: n is a, c, g, t or u
<220> FEATURE:
<221> NAME/KEY: misc_feature
<222> LOCATION: (1076)..(1076)
<223> OTHER INFORMATION: n is a, c, g, t or u
<220> FEATURE:
<221> NAME/KEY: misc_feature

```
<222> LOCATION: (1091)..(1091)
<223> OTHER INFORMATION: n is a, c, g, t or u
<220> FEATURE:
<221> NAME/KEY: misc_feature
<222> LOCATION: (1095)..(1095)
<223> OTHER INFORMATION: n is a, c, g, t or u
<220> FEATURE:
<221> NAME/KEY: misc_feature
<222> LOCATION: (1098)..(1098)
<223> OTHER INFORMATION: n is a, c, g, t or u
<220> FEATURE:
<221> NAME/KEY: misc_feature
<222> LOCATION: (1102)..(1102)
<223> OTHER INFORMATION: n is a, c, g, t or u
<220> FEATURE:
<221> NAME/KEY: misc_feature
<222> LOCATION: (1105)..(1105)
<223> OTHER INFORMATION: n is a, c, g, t or u
<220> FEATURE:
<221> NAME/KEY: misc_feature
<222> LOCATION: (1112)..(1112)
<223> OTHER INFORMATION: n is a, c, g, t or u
<220> FEATURE:
<221> NAME/KEY: misc_feature
<222> LOCATION: (1116)..(1116)
<223> OTHER INFORMATION: n is a, c, g, t or u
<220> FEATURE:
<221> NAME/KEY: misc_feature
<222> LOCATION: (1122)..(1123)
<223> OTHER INFORMATION: n is a, c, g, t or u
<220> FEATURE:
<221> NAME/KEY: misc_feature
<222> LOCATION: (1126)..(1126)
<223> OTHER INFORMATION: n is a, c, g, t or u
<220> FEATURE:
<221> NAME/KEY: misc_feature
<222> LOCATION: (1129)..(1129)
<223> OTHER INFORMATION: n is a, c, g, t or u
<220> FEATURE:
<221> NAME/KEY: misc_feature
<222> LOCATION: (1134)..(1134)
<223> OTHER INFORMATION: n is a, c, g, t or u
<220> FEATURE:
<221> NAME/KEY: misc_feature
<222> LOCATION: (1139)..(1139)
<223> OTHER INFORMATION: n is a, c, g, t or u
<220> FEATURE:
<221> NAME/KEY: misc_feature
<222> LOCATION: (1144)..(1144)
<223> OTHER INFORMATION: n is a, c, g, t or u
<220> FEATURE:
<221> NAME/KEY: misc_feature
<222> LOCATION: (1148)..(1148)
<223> OTHER INFORMATION: n is a, c, g, t or u
<220> FEATURE:
<221> NAME/KEY: misc_feature
<222> LOCATION: (1150)..(1150)
<223> OTHER INFORMATION: n is a, c, g, t or u
<220> FEATURE:
<221> NAME/KEY: misc_feature
<222> LOCATION: (1158)..(1158)
<223> OTHER INFORMATION: n is a, c, g, t or u
<220> FEATURE:
<221> NAME/KEY: misc_feature
<222> LOCATION: (1175)..(1175)
<223> OTHER INFORMATION: n is a, c, g, t or u
<220> FEATURE:
<221> NAME/KEY: misc_feature
<222> LOCATION: (1180)..(1180)
<223> OTHER INFORMATION: n is a, c, g, t or u
<220> FEATURE:
<221> NAME/KEY: misc_feature
<222> LOCATION: (1190)..(1190)
<223> OTHER INFORMATION: n is a, c, g, t or u
<220> FEATURE:
<221> NAME/KEY: misc_feature
<222> LOCATION: (1196)..(1196)
<223> OTHER INFORMATION: n is a, c, g, t or u
<220> FEATURE:
<221> NAME/KEY: misc_feature
```

```
<222> LOCATION: (1200)..(1200)
<223> OTHER INFORMATION: n is a, c, g, t or u
<220> FEATURE:
<221> NAME/KEY: misc_feature
<222> LOCATION: (1202)..(1202)
<223> OTHER INFORMATION: n is a, c, g, t or u
<220> FEATURE:
<221> NAME/KEY: misc_feature
<222> LOCATION: (1206)..(1207)
<223> OTHER INFORMATION: n is a, c, g, t or u
<220> FEATURE:
<221> NAME/KEY: misc_feature
<222> LOCATION: (1215)..(1215)
<223> OTHER INFORMATION: n is a, c, g, t or u
<220> FEATURE:
<221> NAME/KEY: misc_feature
<222> LOCATION: (1224)..(1224)
<223> OTHER INFORMATION: n is a, c, g, t or u
<220> FEATURE:
<221> NAME/KEY: misc_feature
<222> LOCATION: (1231)..(1231)
<223> OTHER INFORMATION: n is a, c, g, t or u
<220> FEATURE:
<221> NAME/KEY: misc_feature
<222> LOCATION: (1238)..(1238)
<223> OTHER INFORMATION: n is a, c, g, t or u
<220> FEATURE:
<221> NAME/KEY: misc_feature
<222> LOCATION: (1245)..(1245)
<223> OTHER INFORMATION: n is a, c, g, t or u
<220> FEATURE:
<221> NAME/KEY: misc_feature
<222> LOCATION: (1249)..(1249)
<223> OTHER INFORMATION: n is a, c, g, t or u
<220> FEATURE:
<221> NAME/KEY: misc_feature
<222> LOCATION: (1273)..(1273)
<223> OTHER INFORMATION: n is a, c, g, t or u
<220> FEATURE:
<221> NAME/KEY: misc_feature
<222> LOCATION: (1276)..(1276)
<223> OTHER INFORMATION: n is a, c, g, t or u
<220> FEATURE:
<221> NAME/KEY: misc_feature
<222> LOCATION: (1284)..(1284)
<223> OTHER INFORMATION: n is a, c, g, t or u
<220> FEATURE:
<221> NAME/KEY: misc_feature
<222> LOCATION: (1299)..(1299)
<223> OTHER INFORMATION: n is a, c, g, t or u
<220> FEATURE:
<221> NAME/KEY: misc_feature
<222> LOCATION: (1309)..(1309)
<223> OTHER INFORMATION: n is a, c, g, t or u
<220> FEATURE:
<221> NAME/KEY: misc_feature
<222> LOCATION: (1312)..(1312)
<223> OTHER INFORMATION: n is a, c, g, t or u
<220> FEATURE:
<221> NAME/KEY: misc_feature
<222> LOCATION: (1319)..(1319)
<223> OTHER INFORMATION: n is a, c, g, t or u
<220> FEATURE:
<221> NAME/KEY: misc_feature
<222> LOCATION: (1321)..(1321)
<223> OTHER INFORMATION: n is a, c, g, t or u
<220> FEATURE:
<221> NAME/KEY: misc_feature
<222> LOCATION: (1325)..(1325)
<223> OTHER INFORMATION: n is a, c, g, t or u
<220> FEATURE:
<221> NAME/KEY: misc_feature
<222> LOCATION: (1328)..(1328)
<223> OTHER INFORMATION: n is a, c, g, t or u
<220> FEATURE:
<221> NAME/KEY: misc_feature
<222> LOCATION: (1335)..(1335)
<223> OTHER INFORMATION: n is a, c, g, t or u
<220> FEATURE:
<221> NAME/KEY: misc_feature
```

<222> LOCATION: (1337)..(1337)
<223> OTHER INFORMATION: n is a, c, g, t or u
<220> FEATURE:
<221> NAME/KEY: misc_feature
<222> LOCATION: (1345)..(1345)
<223> OTHER INFORMATION: n is a, c, g, t or u
<220> FEATURE:
<221> NAME/KEY: misc_feature
<222> LOCATION: (1348)..(1348)
<223> OTHER INFORMATION: n is a, c, g, t or u
<220> FEATURE:
<221> NAME/KEY: misc_feature
<222> LOCATION: (1355)..(1355)
<223> OTHER INFORMATION: n is a, c, g, t or u
<220> FEATURE:
<221> NAME/KEY: misc_feature
<222> LOCATION: (1358)..(1358)
<223> OTHER INFORMATION: n is a, c, g, t or u
<220> FEATURE:
<221> NAME/KEY: misc_feature
<222> LOCATION: (1364)..(1364)
<223> OTHER INFORMATION: n is a, c, g, t or u
<220> FEATURE:
<221> NAME/KEY: misc_feature
<222> LOCATION: (1369)..(1369)
<223> OTHER INFORMATION: n is a, c, g, t or u
<220> FEATURE:
<221> NAME/KEY: misc_feature
<222> LOCATION: (1376)..(1376)
<223> OTHER INFORMATION: n is a, c, g, t or u
<220> FEATURE:
<221> NAME/KEY: misc_feature
<222> LOCATION: (1379)..(1379)
<223> OTHER INFORMATION: n is a, c, g, t or u
<220> FEATURE:
<221> NAME/KEY: misc_feature
<222> LOCATION: (1387)..(1387)
<223> OTHER INFORMATION: n is a, c, g, t or u
<220> FEATURE:
<221> NAME/KEY: misc_feature
<222> LOCATION: (1390)..(1390)
<223> OTHER INFORMATION: n is a, c, g, t or u

<400> SEQUENCE: 5

```
cgtacattcc ctctgaataa ttttgtttac tttaagaagg agatatacat atg gag         56
                                                         Met Glu
                                                         1 aac act gaa aac tca gtg gat tca aaa tcc att aaa aat ttg gaa cca       104
Asn Thr Glu Asn Ser Val Asp Ser Lys Ser Ile Lys Asn Leu Glu Pro
        5                  10                  15 aag atc ata cat gga agc gaa tca atg gac tct gga ata tcc ctg gac       152
Lys Ile Ile His Gly Ser Glu Ser Met Asp Ser Gly Ile Ser Leu Asp
 20                  25                  30 aac agt tat aaa atg gat tat cct gag atg ggt tta tgt ata ata att       200
Asn Ser Tyr Lys Met Asp Tyr Pro Glu Met Gly Leu Cys Ile Ile Ile
 35                  40                  45                  50 aat aat aag aat ttt cat aaa agc act gga atg aca tct cgg tct ggt       248
Asn Asn Lys Asn Phe His Lys Ser Thr Gly Met Thr Ser Arg Ser Gly
             55                  60                  65 aca gat gtc gat gca gca aac ctc agg gaa aca ttc aga aac ttg aaa       296
Thr Asp Val Asp Ala Ala Asn Leu Arg Glu Thr Phe Arg Asn Leu Lys
         70                  75                  80 tat gaa gtc agg aat aaa aat gat ctt aca cgt gaa gaa att gtg gaa       344
Tyr Glu Val Arg Asn Lys Asn Asp Leu Thr Arg Glu Glu Ile Val Glu
     85                  90                  95 ttg atg cgt gat gtt tct aaa gaa gat cac agc aaa agg agc agt ttt       392
Leu Met Arg Asp Val Ser Lys Glu Asp His Ser Lys Arg Ser Ser Phe
100                 105                 110 gtt tgt gtg ctt ctg agc cat ggt gaa gaa gga ata att ttt gga aca       440
Val Cys Val Leu Leu Ser His Gly Glu Glu Gly Ile Ile Phe Gly Thr
115                 120                 125                 130
```

```
aat gga cct gtt gac ctg aaa aaa ata aca aac ttt ttc aga ggg gat        488
Asn Gly Pro Val Asp Leu Lys Lys Ile Thr Asn Phe Phe Arg Gly Asp
            135                 140                 145 cgt tgt aga agt cta act gga aaa ccc aaa ctt ttc att att cag gcc        536
Arg Cys Arg Ser Leu Thr Gly Lys Pro Lys Leu Phe Ile Ile Gln Ala
            150                 155                 160 tgc cgt ggt aca gaa ctg gac tgt ggc att gag aca gac agt ggt gtt        584
Cys Arg Gly Thr Glu Leu Asp Cys Gly Ile Glu Thr Asp Ser Gly Val
            165                 170                 175 gat gct gac atg gcg tgt cat aaa ata cca gtg gag gcc gac ttc ttg        632
Asp Ala Asp Met Ala Cys His Lys Ile Pro Val Glu Ala Asp Phe Leu
        180                 185                 190 tat gca tac tcc aca gca cct ggt tat tat tct tgg cga aat tca aag        680
Tyr Ala Tyr Ser Thr Ala Pro Gly Tyr Tyr Ser Trp Arg Asn Ser Lys
195                 200                 205                 210 gat ggc tcc tgg ttc atc cag tcg ctt tgt gcc atg ctg aaa cag tat        728
Asp Gly Ser Trp Phe Ile Gln Ser Leu Cys Ala Met Leu Lys Gln Tyr
            215                 220                 225 gcc gac aag ctt gaa ttt atg cac att ctt acc cgg gtt aac cga aag        776
Ala Asp Lys Leu Glu Phe Met His Ile Leu Thr Arg Val Asn Arg Lys
            230                 235                 240 gtg gca aca gaa ttt gag tcc ttt tcc ttt gac gct act ttt cat gca        824
Val Ala Thr Glu Phe Glu Ser Phe Ser Phe Asp Ala Thr Phe His Ala
            245                 250                 255 aag aaa cag att cca tgt att gtt tcc atg ctc aca aaa gaa ctc tat        872
Lys Lys Gln Ile Pro Cys Ile Val Ser Met Leu Thr Lys Glu Leu Tyr
            260                 265                 270 ttt tat cac ctcgagcacc accaccacca ccactgagat ccggctgcta                921
Phe Tyr His
275 cnaagcccga angaagctga nttggctgct gccccgctg ancaataact agcatanccc      981 cttggggccn ctnaacgggt ctggaggggt ttttgctgaa nggggacctn tntccggatt     1041 ggcnanggga ccccccctgn accgcncntt aaccncgcgg ggggggggtn cccncanggg     1101 nccnctacct ngccgcccc nnacncncc ccnttcnttt ctncctncnt tccccccngtt     1161 cccgggtttc ccgnagccna acgggggnc ccttnggtnc nattnngctt tccnccccc      1221 ccnaaacttn taggggnggt cccngggncc ccccgaaagg tttccccttg cnggnccccc     1281 ttnaaggact ttcccagnaa cccccccncg nccctttntn aggntcnccc cccngnaaag    1341 ggtnaantcc gttnaanccc ttnggctngg gggcnccntt tttttnttnc ccccccc       1398

<210> SEQ ID NO 6
<211> LENGTH: 277
<212> TYPE: PRT
<213> ORGANISM: Homo sapiens

<400> SEQUENCE: 6

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80
```

```
Leu Lys Tyr Glu Val Arg Asn Lys Asn Asp Leu Thr Arg Glu Glu Ile
                 85                  90                  95
Val Glu Leu Met Arg Asp Val Ser Lys Glu Asp His Ser Lys Arg Ser
            100                 105                 110
Ser Phe Val Cys Val Leu Leu Ser His Gly Glu Glu Gly Ile Ile Phe
        115                 120                 125
Gly Thr Asn Gly Pro Val Asp Leu Lys Lys Ile Thr Asn Phe Phe Arg
    130                 135                 140
Gly Asp Arg Cys Arg Ser Leu Thr Gly Lys Pro Lys Leu Phe Ile Ile
145                 150                 155                 160
Gln Ala Cys Arg Gly Thr Glu Leu Asp Cys Gly Ile Glu Thr Asp Ser
                165                 170                 175
Gly Val Asp Ala Asp Met Ala Cys His Lys Ile Pro Val Glu Ala Asp
            180                 185                 190
Phe Leu Tyr Ala Tyr Ser Thr Ala Pro Gly Tyr Tyr Ser Trp Arg Asn
        195                 200                 205
Ser Lys Asp Gly Ser Trp Phe Ile Gln Ser Leu Cys Ala Met Leu Lys
    210                 215                 220
Gln Tyr Ala Asp Lys Leu Glu Phe Met His Ile Leu Thr Arg Val Asn
225                 230                 235                 240
Arg Lys Val Ala Thr Glu Phe Glu Ser Phe Ser Phe Asp Ala Thr Phe
                245                 250                 255
His Ala Lys Lys Gln Ile Pro Cys Ile Val Ser Met Leu Thr Lys Glu
            260                 265                 270
Leu Tyr Phe Tyr His
        275

<210> SEQ ID NO 7
<211> LENGTH: 1316
<212> TYPE: DNA
<213> ORGANISM: Homo sapiens
<220> FEATURE:
<221> NAME/KEY: CDS
<222> LOCATION: (51)..(881)
<223> OTHER INFORMATION: Procaspase-3; with amino acid DDD to DAD safety
      catch mutant sequence
<220> FEATURE:
<221> NAME/KEY: misc_feature
<222> LOCATION: (914)..(914)
<223> OTHER INFORMATION: n is a, c, g, t or u
<220> FEATURE:
<221> NAME/KEY: misc_feature
<222> LOCATION: (942)..(942)
<223> OTHER INFORMATION: n is a, c, g, t or u
<220> FEATURE:
<221> NAME/KEY: misc_feature
<222> LOCATION: (958)..(958)
<223> OTHER INFORMATION: n is a, c, g, t or u
<220> FEATURE:
<221> NAME/KEY: misc_feature
<222> LOCATION: (982)..(982)
<223> OTHER INFORMATION: n is a, c, g, t or u
<220> FEATURE:
<221> NAME/KEY: misc_feature
<222> LOCATION: (986)..(986)
<223> OTHER INFORMATION: n is a, c, g, t or u
<220> FEATURE:
<221> NAME/KEY: misc_feature
<222> LOCATION: (988)..(988)
<223> OTHER INFORMATION: n is a, c, g, t or u
<220> FEATURE:
<221> NAME/KEY: misc_feature
<222> LOCATION: (1006)..(1006)
<223> OTHER INFORMATION: n is a, c, g, t or u
<220> FEATURE:
<221> NAME/KEY: misc_feature
<222> LOCATION: (1026)..(1026)
```

```
<223> OTHER INFORMATION: n is a, c, g, t or u
<220> FEATURE:
<221> NAME/KEY: misc_feature
<222> LOCATION: (1032)..(1032)
<223> OTHER INFORMATION: n is a, c, g, t or u
<220> FEATURE:
<221> NAME/KEY: misc_feature
<222> LOCATION: (1038)..(1038)
<223> OTHER INFORMATION: n is a, c, g, t or u
<220> FEATURE:
<221> NAME/KEY: misc_feature
<222> LOCATION: (1040)..(1041)
<223> OTHER INFORMATION: n is a, c, g, t or u
<220> FEATURE:
<221> NAME/KEY: misc_feature
<222> LOCATION: (1051)..(1051)
<223> OTHER INFORMATION: n is a, c, g, t or u
<220> FEATURE:
<221> NAME/KEY: misc_feature
<222> LOCATION: (1062)..(1062)
<223> OTHER INFORMATION: n is a, c, g, t or u
<220> FEATURE:
<221> NAME/KEY: misc_feature
<222> LOCATION: (1067)..(1067)
<223> OTHER INFORMATION: n is a, c, g, t or u
<220> FEATURE:
<221> NAME/KEY: misc_feature
<222> LOCATION: (1073)..(1073)
<223> OTHER INFORMATION: n is a, c, g, t or u
<220> FEATURE:
<221> NAME/KEY: misc_feature
<222> LOCATION: (1097)..(1097)
<223> OTHER INFORMATION: n is a, c, g, t or u
<220> FEATURE:
<221> NAME/KEY: misc_feature
<222> LOCATION: (1101)..(1101)
<223> OTHER INFORMATION: n is a, c, g, t or u
<220> FEATURE:
<221> NAME/KEY: misc_feature
<222> LOCATION: (1106)..(1106)
<223> OTHER INFORMATION: n is a, c, g, t or u
<220> FEATURE:
<221> NAME/KEY: misc_feature
<222> LOCATION: (1108)..(1108)
<223> OTHER INFORMATION: n is a, c, g, t or u
<220> FEATURE:
<221> NAME/KEY: misc_feature
<222> LOCATION: (1114)..(1114)
<223> OTHER INFORMATION: n is a, c, g, t or u
<220> FEATURE:
<221> NAME/KEY: misc_feature
<222> LOCATION: (1118)..(1118)
<223> OTHER INFORMATION: n is a, c, g, t or u
<220> FEATURE:
<221> NAME/KEY: misc_feature
<222> LOCATION: (1123)..(1123)
<223> OTHER INFORMATION: n is a, c, g, t or u
<220> FEATURE:
<221> NAME/KEY: misc_feature
<222> LOCATION: (1129)..(1129)
<223> OTHER INFORMATION: n is a, c, g, t or u
<220> FEATURE:
<221> NAME/KEY: misc_feature
<222> LOCATION: (1134)..(1134)
<223> OTHER INFORMATION: n is a, c, g, t or u
<220> FEATURE:
<221> NAME/KEY: misc_feature
<222> LOCATION: (1148)..(1149)
<223> OTHER INFORMATION: n is a, c, g, t or u
<220> FEATURE:
<221> NAME/KEY: misc_feature
<222> LOCATION: (1151)..(1151)
<223> OTHER INFORMATION: n is a, c, g, t or u
<220> FEATURE:
<221> NAME/KEY: misc_feature
<222> LOCATION: (1154)..(1154)
<223> OTHER INFORMATION: n is a, c, g, t or u
<220> FEATURE:
<221> NAME/KEY: misc_feature
<222> LOCATION: (1156)..(1157)
```

```
<223> OTHER INFORMATION: n is a, c, g, t or u
<220> FEATURE:
<221> NAME/KEY: misc_feature
<222> LOCATION: (1173)..(1173)
<223> OTHER INFORMATION: n is a, c, g, t or u
<220> FEATURE:
<221> NAME/KEY: misc_feature
<222> LOCATION: (1193)..(1193)
<223> OTHER INFORMATION: n is a, c, g, t or u
<220> FEATURE:
<221> NAME/KEY: misc_feature
<222> LOCATION: (1200)..(1200)
<223> OTHER INFORMATION: n is a, c, g, t or u
<220> FEATURE:
<221> NAME/KEY: misc_feature
<222> LOCATION: (1206)..(1206)
<223> OTHER INFORMATION: n is a, c, g, t or u
<220> FEATURE:
<221> NAME/KEY: misc_feature
<222> LOCATION: (1215)..(1215)
<223> OTHER INFORMATION: n is a, c, g, t or u
<220> FEATURE:
<221> NAME/KEY: misc_feature
<222> LOCATION: (1228)..(1230)
<223> OTHER INFORMATION: n is a, c, g, t or u
<220> FEATURE:
<221> NAME/KEY: misc_feature
<222> LOCATION: (1232)..(1232)
<223> OTHER INFORMATION: n is a, c, g, t or u
<220> FEATURE:
<221> NAME/KEY: misc_feature
<222> LOCATION: (1247)..(1247)
<223> OTHER INFORMATION: n is a, c, g, t or u
<220> FEATURE:
<221> NAME/KEY: misc_feature
<222> LOCATION: (1250)..(1250)
<223> OTHER INFORMATION: n is a, c, g, t or u
<220> FEATURE:
<221> NAME/KEY: misc_feature
<222> LOCATION: (1261)..(1261)
<223> OTHER INFORMATION: n is a, c, g, t or u
<220> FEATURE:
<221> NAME/KEY: misc_feature
<222> LOCATION: (1263)..(1264)
<223> OTHER INFORMATION: n is a, c, g, t or u
<220> FEATURE:
<221> NAME/KEY: misc_feature
<222> LOCATION: (1272)..(1272)
<223> OTHER INFORMATION: n is a, c, g, t or u
<220> FEATURE:
<221> NAME/KEY: misc_feature
<222> LOCATION: (1275)..(1275)
<223> OTHER INFORMATION: n is a, c, g, t or u
<220> FEATURE:
<221> NAME/KEY: misc_feature
<222> LOCATION: (1277)..(1277)
<223> OTHER INFORMATION: n is a, c, g, t or u
<220> FEATURE:
<221> NAME/KEY: misc_feature
<222> LOCATION: (1286)..(1286)
<223> OTHER INFORMATION: n is a, c, g, t or u
<220> FEATURE:
<221> NAME/KEY: misc_feature
<222> LOCATION: (1289)..(1289)
<223> OTHER INFORMATION: n is a, c, g, t or u
<220> FEATURE:
<221> NAME/KEY: misc_feature
<222> LOCATION: (1291)..(1292)
<223> OTHER INFORMATION: n is a, c, g, t or u
<220> FEATURE:
<221> NAME/KEY: misc_feature
<222> LOCATION: (1294)..(1294)
<223> OTHER INFORMATION: n is a, c, g, t or u
<220> FEATURE:
<221> NAME/KEY: misc_feature
<222> LOCATION: (1299)..(1299)
<223> OTHER INFORMATION: n is a, c, g, t or u
<220> FEATURE:
<221> NAME/KEY: misc_feature
<222> LOCATION: (1301)..(1301)
```

```
<223> OTHER INFORMATION: n is a, c, g, t or u
<220> FEATURE:
<221> NAME/KEY: misc_feature
<222> LOCATION: (1304)..(1304)
<223> OTHER INFORMATION: n is a, c, g, t or u
<220> FEATURE:
<221> NAME/KEY: misc_feature
<222> LOCATION: (1307)..(1307)
<223> OTHER INFORMATION: n is a, c, g, t or u
<220> FEATURE:
<221> NAME/KEY: misc_feature
<222> LOCATION: (1316)..(1316)
<223> OTHER INFORMATION: n is a, c, g, t or u

<400> SEQUENCE: 7
cgtacattcc ctctgaataa ttttgtttac tttaagaagg agatatacat atg gag        56
                                                        Met Glu
                                                        1 aac act gaa aac tca gtg gat tca aaa tcc att aaa aat ttg gaa cca      104
Asn Thr Glu Asn Ser Val Asp Ser Lys Ser Ile Lys Asn Leu Glu Pro
        5                  10                  15 aag atc ata cat gga agc gaa tca atg gac tct gga ata tcc ctg gac      152
Lys Ile Ile His Gly Ser Glu Ser Met Asp Ser Gly Ile Ser Leu Asp
 20                  25                  30 aac agt tat aaa atg gat tat cct gag atg ggt tta tgt ata ata att      200
Asn Ser Tyr Lys Met Asp Tyr Pro Glu Met Gly Leu Cys Ile Ile Ile
 35                  40                  45                  50 aat aat aag aat ttt cat aaa agc act gga atg aca tct cgg tct ggt      248
Asn Asn Lys Asn Phe His Lys Ser Thr Gly Met Thr Ser Arg Ser Gly
                 55                  60                  65 aca gat gtc gat gca gca aac ctc agg gaa aca ttc aga aac ttg aaa      296
Thr Asp Val Asp Ala Ala Asn Leu Arg Glu Thr Phe Arg Asn Leu Lys
             70                  75                  80 tat gaa gtc agg aat aaa aat gat ctt aca cgt gaa gaa att gtg gaa      344
Tyr Glu Val Arg Asn Lys Asn Asp Leu Thr Arg Glu Glu Ile Val Glu
         85                  90                  95 ttg atg cgt gat gtt tct aaa gaa gat cac agc aaa agg agc agt ttt      392
Leu Met Arg Asp Val Ser Lys Glu Asp His Ser Lys Arg Ser Ser Phe
    100                 105                 110 gtt tgt gtg ctt ctg agc cat ggt gaa gaa gga ata att ttt gga aca      440
Val Cys Val Leu Leu Ser His Gly Glu Glu Gly Ile Ile Phe Gly Thr
115                 120                 125                 130 aat gga cct gtt gac ctg aaa aaa ata aca aac ttt ttc aga ggg gat      488
Asn Gly Pro Val Asp Leu Lys Lys Ile Thr Asn Phe Phe Arg Gly Asp
                135                 140                 145 cgt tgt aga agt cta act gga aaa ccc aaa ctt ttc att att cag gcc      536
Arg Cys Arg Ser Leu Thr Gly Lys Pro Lys Leu Phe Ile Ile Gln Ala
            150                 155                 160 tgc cgt ggt aca gaa ctg gac tgt ggc att gag aca gac agt ggt gtt      584
Cys Arg Gly Thr Glu Leu Asp Cys Gly Ile Glu Thr Asp Ser Gly Val
        165                 170                 175 gat gat gcc atg gcg tgt cat aaa ata cca gtg gag gcc gac ttc ttg      632
Asp Asp Ala Met Ala Cys His Lys Ile Pro Val Glu Ala Asp Phe Leu
    180                 185                 190 tat gca tac tcc aca gca cct ggt tat tat tct tgg cga aat tca aag      680
Tyr Ala Tyr Ser Thr Ala Pro Gly Tyr Tyr Ser Trp Arg Asn Ser Lys
195                 200                 205                 210 gat ggc tcc tgg ttc atc cag tcg ctt tgt gcc atg ctg aaa cag tat      728
Asp Gly Ser Trp Phe Ile Gln Ser Leu Cys Ala Met Leu Lys Gln Tyr
                215                 220                 225 gcc gac aag ctt gaa ttt atg cac att ctt acc cgg gtt aac cga aag      776
Ala Asp Lys Leu Glu Phe Met His Ile Leu Thr Arg Val Asn Arg Lys
            230                 235                 240
```

```
gtg gca aca gaa ttt gag tcc ttt tcc ttt gac gct act ttt cat gca      824
Val Ala Thr Glu Phe Glu Ser Phe Ser Phe Asp Ala Thr Phe His Ala
            245                 250                 255 aag aaa cag att cca tgt att gtt tcc atg ctc aca aaa gaa ctc tat      872
Lys Lys Gln Ile Pro Cys Ile Val Ser Met Leu Thr Lys Glu Leu Tyr
    260                 265                 270 ttt tat cac ctcgagcacc ccccaccac cactgagatc cgnctgctac               921
Phe Tyr His
275 aaagcccgaa aggaagctga nttggctgct gccccncctg accataccta gcatacccct    981 ngggncncta acgggtctgg ggggnttttg ctgaaggggg acctnttccg natggcnann    1041 ggacccccn gtaccgccct naaccngcgg gnggggttc cccacggac cctacntgcn       1101 gcccnanccc ccnccttncct tntcctcntt ccnccgtccg gttccnnan ctannggc      1161 ccttggtcca tnggcttcgc cccccccaaa cnttagggng gtccngggcc cccnaaaggt   1221 tcccttnnng nccccttaa ggactntcnc ggacccccn cnnctttttt nagntncctc      1281 cctgnaangn ntnaaatncn ttnaancct gggcn                                1316
```

<210> SEQ ID NO 8
<211> LENGTH: 277
<212> TYPE: PRT
<213> ORGANISM: Homo sapiens

<400> SEQUENCE: 8

```
Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Ala Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
```

245                 250                 255
His Ala Lys Lys Gln Ile Pro Cys Ile Val Ser Met Leu Thr Lys Glu
            260                 265                 270

Leu Tyr Phe Tyr His
        275

<210> SEQ ID NO 9
<211> LENGTH: 277
<212> TYPE: PRT
<213> ORGANISM: Homo sapiens
<220> FEATURE:
<221> NAME/KEY: MISC_FEATURE
<222> LOCATION: (1)..(277)
<223> OTHER INFORMATION: Procaspase-3; with amino acid DDD wild-type
      safety catch sequence (ACCESSION Number NM_004346)

<400> SEQUENCE: 9

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275

<210> SEQ ID NO 10
<211> LENGTH: 277
<212> TYPE: PRT
<213> ORGANISM: Homo sapiens

```
<220> FEATURE:
<221> NAME/KEY: MISC_FEATURE
<222> LOCATION: (1)..(277)
<223> OTHER INFORMATION: Procaspase-3; with amino acid DDD to ADD safety
      catch mutant sequence

<400> SEQUENCE: 10

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Ala Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275

<210> SEQ ID NO 11
<211> LENGTH: 277
<212> TYPE: PRT
<213> ORGANISM: Homo sapiens
<220> FEATURE:
<221> NAME/KEY: MISC_FEATURE
<222> LOCATION: (1)..(277)
<223> OTHER INFORMATION: Procaspase-3; with amino acid DDD to DAD safety
      catch mutant sequence

<400> SEQUENCE: 11

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30
```

Leu Asp Asn Ser Tyr Lys Met Asp Tyr Pro Glu Met Gly Leu Cys Ile
            35                  40                  45

Ile Ile Asn Asn Lys Asn Phe His Lys Ser Thr Gly Met Thr Ser Arg
 50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Ala Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Xaa Lys Lys Gln Ile Pro Cys Ile Val Ser Met Leu Thr Lys Glu
            260                 265                 270

Leu Tyr Phe Tyr His
        275

<210> SEQ ID NO 12
<211> LENGTH: 277
<212> TYPE: PRT
<213> ORGANISM: Homo sapiens
<220> FEATURE:
<221> NAME/KEY: MISC_FEATURE
<222> LOCATION: (1)..(277)
<223> OTHER INFORMATION: Procaspase-3; with amino acid DDD to DAD safety
      catch mutant sequence

<400> SEQUENCE: 12

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

```
Val Glu Leu Met Arg Asp Val Ser Lys Glu Asp His Ser Lys Arg Ser
            100                 105                 110

Ser Phe Val Cys Val Leu Leu Ser His Gly Glu Gly Ile Ile Phe
        115                 120                 125

Gly Thr Asn Gly Pro Val Asp Leu Lys Lys Ile Thr Asn Phe Phe Arg
130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Ala Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275

<210> SEQ ID NO 13
<211> LENGTH: 45
<212> TYPE: DNA
<213> ORGANISM: Artificial
<220> FEATURE:
<223> OTHER INFORMATION: Synthetic oligo

<400> SEQUENCE: 13
gacagacagt ggtgttgcgg atgacatggc gtgtcataaa atacc                45

<210> SEQ ID NO 14
<211> LENGTH: 45
<212> TYPE: DNA
<213> ORGANISM: Artificial
<220> FEATURE:
<223> OTHER INFORMATION: Synthetic oligo

<400> SEQUENCE: 14
gacagacagt ggtgttgatg ctgacatggc gtgtcataaa atacc                45

<210> SEQ ID NO 15
<211> LENGTH: 45
<212> TYPE: DNA
<213> ORGANISM: Artificial
<220> FEATURE:
<223> OTHER INFORMATION: Synthetic oligo

<400> SEQUENCE: 15
gacagacagt ggtgttgatg atgccatggc gtgtcataaa atacc                45

<210> SEQ ID NO 16
<211> LENGTH: 912
<212> TYPE: DNA
<213> ORGANISM: Homo sapiens
<220> FEATURE:
<221> NAME/KEY: CDS
<222> LOCATION: (1)..(912)
```

<223> OTHER INFORMATION: Procaspase-7 with amino acid DTD wild-type safety catch sequence (Accession Number NM_001227)

<400> SEQUENCE: 16

| | | | | | | | | | | | | | | | | |
|---|---|---|---|---|---|---|---|---|---|---|---|---|---|---|---|---|
| atg | gca | gat | gat | cag | ggc | tgt | att | gaa | gag | cag | ggg | gtt | gag | gat | tca | 48 |
| Met | Ala | Asp | Asp | Gln | Gly | Cys | Ile | Glu | Glu | Gln | Gly | Val | Glu | Asp | Ser | |
| 1 | | | | 5 | | | | | 10 | | | | | 15 | | |
| gca | aat | gaa | gat | tca | gtg | gat | gct | aag | cca | gac | cgg | tcc | tcg | ttt | gta | 96 |
| Ala | Asn | Glu | Asp | Ser | Val | Asp | Ala | Lys | Pro | Asp | Arg | Ser | Ser | Phe | Val | |
| | | | 20 | | | | | 25 | | | | | 30 | | | |
| ccg | tcc | ctc | ttc | agt | aag | aag | aag | aaa | aat | gtc | acc | atg | cga | tcc | atc | 144 |
| Pro | Ser | Leu | Phe | Ser | Lys | Lys | Lys | Lys | Asn | Val | Thr | Met | Arg | Ser | Ile | |
| | | 35 | | | | | 40 | | | | | 45 | | | | |
| aag | acc | acc | cgg | gac | cga | gtg | cct | aca | tat | cag | tac | aac | atg | aat | ttt | 192 |
| Lys | Thr | Thr | Arg | Asp | Arg | Val | Pro | Thr | Tyr | Gln | Tyr | Asn | Met | Asn | Phe | |
| 50 | | | | | 55 | | | | | 60 | | | | | | |
| gaa | aag | ctg | ggc | aaa | tgc | ata | ata | aac | aac | aag | aac | ttt | gat | aaa | 240 | |
| Glu | Lys | Leu | Gly | Lys | Cys | Ile | Ile | Ile | Asn | Asn | Lys | Asn | Phe | Asp | Lys | |
| 65 | | | | 70 | | | | | 75 | | | | | 80 | | |
| gtg | aca | ggt | atg | ggc | gtt | cga | aac | gga | aca | gac | aaa | gat | gcc | gag | gcg | 288 |
| Val | Thr | Gly | Met | Gly | Val | Arg | Asn | Gly | Thr | Asp | Lys | Asp | Ala | Glu | Ala | |
| | | | | 85 | | | | | 90 | | | | | 95 | | |
| ctc | ttc | aag | tgc | ttc | cga | agc | ctg | ggt | ttt | gac | gtg | att | gtc | tat | aat | 336 |
| Leu | Phe | Lys | Cys | Phe | Arg | Ser | Leu | Gly | Phe | Asp | Val | Ile | Val | Tyr | Asn | |
| | | 100 | | | | | 105 | | | | | 110 | | | | |
| gac | tgc | tct | tgt | gcc | aag | atg | caa | gat | ctg | ctt | aaa | aaa | gct | tct | gaa | 384 |
| Asp | Cys | Ser | Cys | Ala | Lys | Met | Gln | Asp | Leu | Leu | Lys | Lys | Ala | Ser | Glu | |
| | | 115 | | | | | 120 | | | | | 125 | | | | |
| gag | gac | cat | aca | aat | gcc | gcc | tgc | ttc | gcc | tgc | atc | ctc | tta | agc | cat | 432 |
| Glu | Asp | His | Thr | Asn | Ala | Ala | Cys | Phe | Ala | Cys | Ile | Leu | Leu | Ser | His | |
| 130 | | | | | 135 | | | | | 140 | | | | | | |
| gga | gaa | gaa | aat | gta | att | tat | ggg | aaa | gat | ggt | gtc | aca | cca | ata | aag | 480 |
| Gly | Glu | Glu | Asn | Val | Ile | Tyr | Gly | Lys | Asp | Gly | Val | Thr | Pro | Ile | Lys | |
| 145 | | | | | 150 | | | | | 155 | | | | | 160 | |
| gat | ttg | aca | gcc | cac | ttt | agg | ggg | gat | aga | tgc | aaa | acc | ctt | tta | gag | 528 |
| Asp | Leu | Thr | Ala | His | Phe | Arg | Gly | Asp | Arg | Cys | Lys | Thr | Leu | Leu | Glu | |
| | | | | 165 | | | | | 170 | | | | | 175 | | |
| aaa | ccc | aaa | ctc | ttc | ttc | att | cag | gct | tgc | cga | ggg | acc | gag | ctt | gat | 576 |
| Lys | Pro | Lys | Leu | Phe | Phe | Ile | Gln | Ala | Cys | Arg | Gly | Thr | Glu | Leu | Asp | |
| | | | 180 | | | | | 185 | | | | | 190 | | | |
| gat | ggc | atc | cag | gcc | gac | tcg | ggg | ccc | atc | aat | gac | aca | gat | gct | aat | 624 |
| Asp | Gly | Ile | Gln | Ala | Asp | Ser | Gly | Pro | Ile | Asn | Asp | Thr | Asp | Ala | Asn | |
| | | 195 | | | | | 200 | | | | | 205 | | | | |
| cct | cga | tac | aag | atc | cca | gtg | gaa | gct | gac | ttc | ctc | ttc | gcc | tat | tcc | 672 |
| Pro | Arg | Tyr | Lys | Ile | Pro | Val | Glu | Ala | Asp | Phe | Leu | Phe | Ala | Tyr | Ser | |
| 210 | | | | | 215 | | | | | 220 | | | | | | |
| acg | gtt | cca | ggc | tat | tac | tcg | tgg | agg | agc | cca | gga | aga | ggc | tcc | tgg | 720 |
| Thr | Val | Pro | Gly | Tyr | Tyr | Ser | Trp | Arg | Ser | Pro | Gly | Arg | Gly | Ser | Trp | |
| 225 | | | | | 230 | | | | | 235 | | | | | 240 | |
| ttt | gtg | caa | gcc | ctc | tgc | tcc | atc | ctg | gag | gag | cac | gga | aaa | gac | ctg | 768 |
| Phe | Val | Gln | Ala | Leu | Cys | Ser | Ile | Leu | Glu | Glu | His | Gly | Lys | Asp | Leu | |
| | | | | 245 | | | | | 250 | | | | | 255 | | |
| gaa | atc | atg | cag | atc | ctc | acc | agg | gtg | aat | gac | aga | gtt | gcc | agg | cac | 816 |
| Glu | Ile | Met | Gln | Ile | Leu | Thr | Arg | Val | Asn | Asp | Arg | Val | Ala | Arg | His | |
| | | | 260 | | | | | 265 | | | | | 270 | | | |
| ttt | gag | tct | cag | tct | gat | gac | cca | cac | ttc | cat | gag | aag | aag | cag | atc | 864 |
| Phe | Glu | Ser | Gln | Ser | Asp | Asp | Pro | His | Phe | His | Glu | Lys | Lys | Gln | Ile | |
| | | 275 | | | | | 280 | | | | | 285 | | | | |
| ccc | tgt | gtg | gtc | tcc | atg | ctc | acc | aag | gaa | ctc | tac | ttc | agt | caa | tag | 912 |
| Pro | Cys | Val | Val | Ser | Met | Leu | Thr | Lys | Glu | Leu | Tyr | Phe | Ser | Gln | | |
| | 290 | | | | | 295 | | | | | 300 | | | | | |

<210> SEQ ID NO 17
<211> LENGTH: 303
<212> TYPE: PRT
<213> ORGANISM: Homo sapiens

<400> SEQUENCE: 17

Met Ala Asp Asp Gln Gly Cys Ile Glu Glu Gln Gly Val Glu Asp Ser
1               5                   10                  15

Ala Asn Glu Asp Ser Val Asp Ala Lys Pro Asp Arg Ser Ser Phe Val
            20                  25                  30

Pro Ser Leu Phe Ser Lys Lys Lys Asn Val Thr Met Arg Ser Ile
        35                  40                  45

Lys Thr Thr Arg Asp Arg Val Pro Thr Tyr Gln Tyr Asn Met Asn Phe
50                  55                  60

Glu Lys Leu Gly Lys Cys Ile Ile Ile Asn Asn Lys Asn Phe Asp Lys
65                  70                  75                  80

Val Thr Gly Met Gly Val Arg Asn Gly Thr Asp Lys Asp Ala Glu Ala
                85                  90                  95

Leu Phe Lys Cys Phe Arg Ser Leu Gly Phe Asp Val Ile Val Tyr Asn
            100                 105                 110

Asp Cys Ser Cys Ala Lys Met Gln Asp Leu Leu Lys Lys Ala Ser Glu
        115                 120                 125

Glu Asp His Thr Asn Ala Ala Cys Phe Ala Cys Ile Leu Leu Ser His
130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Cys Arg Gly Thr Glu Leu Asp
            180                 185                 190

Asp Gly Ile Gln Ala Asp Ser Gly Pro Ile Asn Asp Thr Asp Ala Asn
        195                 200                 205

Pro Arg Tyr Lys Ile Pro Val Glu Ala Asp Phe Leu Phe Ala Tyr Ser
210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255

Glu Ile Met Gln Ile Leu Thr Arg Val Asn Asp Arg Val Ala Arg His
            260                 265                 270

Phe Glu Ser Gln Ser Asp Asp Pro His Phe His Glu Lys Lys Gln Ile
        275                 280                 285

Pro Cys Val Val Ser Met Leu Thr Lys Glu Leu Tyr Phe Ser Gln
290                 295                 300

<210> SEQ ID NO 18
<211> LENGTH: 912
<212> TYPE: DNA
<213> ORGANISM: Homo sapiens
<220> FEATURE:
<221> NAME/KEY: CDS
<222> LOCATION: (1)..(912)
<223> OTHER INFORMATION: Procaspase-7 DDD wild-type safety catch
      sequence

<400> SEQUENCE: 18 atg gca gat gat cag ggc tgt att gaa gag cag ggg gtt gag gat tca            48

```
Met Ala Asp Asp Gln Gly Cys Ile Glu Glu Gln Gly Val Glu Asp Ser
1               5                   10                  15 gca aat gaa gat tca gtg gat gct aag cca gac cgg tcc tcg ttt gta      96
Ala Asn Glu Asp Ser Val Asp Ala Lys Pro Asp Arg Ser Ser Phe Val
            20                  25                  30 ccg tcc ctc ttc agt aag aag aag aaa aat gtc acc atg cga tcc atc     144
Pro Ser Leu Phe Ser Lys Lys Lys Lys Asn Val Thr Met Arg Ser Ile
        35                  40                  45 aag acc acc cgg gac cga gtg cct aca tat cag tac aac atg aat ttt     192
Lys Thr Thr Arg Asp Arg Val Pro Thr Tyr Gln Tyr Asn Met Asn Phe
    50                  55                  60 gaa aag ctg ggc aaa tgc atc ata ata aac aac aag aac ttt gat aaa     240
Glu Lys Leu Gly Lys Cys Ile Ile Ile Asn Asn Lys Asn Phe Asp Lys
65                  70                  75                  80 gtg aca ggt atg ggc gtt cga aac gga aca gac aaa gat gcc gag gcg     288
Val Thr Gly Met Gly Val Arg Asn Gly Thr Asp Lys Asp Ala Glu Ala
                85                  90                  95 ctc ttc aag tgc ttc cga agc ctg ggt ttt gac gtg att gtc tat aat     336
Leu Phe Lys Cys Phe Arg Ser Leu Gly Phe Asp Val Ile Val Tyr Asn
            100                 105                 110 gac tgc tct tgt gcc aag atg caa gat ctg ctt aaa aaa gct tct gaa     384
Asp Cys Ser Cys Ala Lys Met Gln Asp Leu Leu Lys Lys Ala Ser Glu
        115                 120                 125 gag gac cat aca aat gcc gcc tgc ttc gcc tgc atc ctc tta agc cat     432
Glu Asp His Thr Asn Ala Ala Cys Phe Ala Cys Ile Leu Leu Ser His
    130                 135                 140 gga gaa gaa aat gta att tat ggg aaa gat ggt gtc aca cca ata aag     480
Gly Glu Glu Asn Val Ile Tyr Gly Lys Asp Gly Val Thr Pro Ile Lys
145                 150                 155                 160 gat ttg aca gcc cac ttt agg ggg gat aga tgc aaa acc ctt tta gag     528
Asp Leu Thr Ala His Phe Arg Gly Asp Arg Cys Lys Thr Leu Leu Glu
                165                 170                 175 aaa ccc aaa ctc ttc ttc att cag gct tgc cga ggg acc gag ctt gat     576
Lys Pro Lys Leu Phe Phe Ile Gln Ala Cys Arg Gly Thr Glu Leu Asp
            180                 185                 190 gat ggc atc cag gcc gac tcg ggg ccc atc aat gac gca gat gct aat     624
Asp Gly Ile Gln Ala Asp Ser Gly Pro Ile Asn Asp Ala Asp Ala Asn
        195                 200                 205 cct cga tac aag atc cca gtg gaa gct gac ttc ctc ttc gcc tat tcc     672
Pro Arg Tyr Lys Ile Pro Val Glu Ala Asp Phe Leu Phe Ala Tyr Ser
    210                 215                 220 acg gtt cca ggc tat tac tcg tgg agg agc cca gga aga ggc tcc tgg     720
Thr Val Pro Gly Tyr Tyr Ser Trp Arg Ser Pro Gly Arg Gly Ser Trp
225                 230                 235                 240 ttt gtg caa gcc ctc tgc tcc atc ctg gag gag cac gga aaa gac ctg     768
Phe Val Gln Ala Leu Cys Ser Ile Leu Glu Glu His Gly Lys Asp Leu
                245                 250                 255 gaa atc atg cag atc ctc acc agg gtg aat gac aga gtt gcc agg cac     816
Glu Ile Met Gln Ile Leu Thr Arg Val Asn Asp Arg Val Ala Arg His
            260                 265                 270 ttt gag tct cag tct gat gac cca cac ttc cat gag aag aag cag atc     864
Phe Glu Ser Gln Ser Asp Asp Pro His Phe His Glu Lys Lys Gln Ile
        275                 280                 285 ccc tgt gtg gtc tcc atg ctc acc aag gaa ctc tac ttc agt caa tag    912
Pro Cys Val Val Ser Met Leu Thr Lys Glu Leu Tyr Phe Ser Gln
    290                 295                 300

<210> SEQ ID NO 19
<211> LENGTH: 303
<212> TYPE: PRT
<213> ORGANISM: Homo sapiens
```

<400> SEQUENCE: 19

| | | | | | | | | | | | | | | |
|---|---|---|---|---|---|---|---|---|---|---|---|---|---|---|
| Met | Ala | Asp | Asp | Gln | Gly | Cys | Ile | Glu | Glu | Gln | Gly | Val | Glu | Asp | Ser |
| 1 | | | | 5 | | | | | 10 | | | | | 15 | |

Ala Asn Glu Asp Ser Val Asp Ala Lys Pro Asp Arg Ser Ser Phe Val
            20                  25                  30

Pro Ser Leu Phe Ser Lys Lys Lys Asn Val Thr Met Arg Ser Ile
        35                  40                  45

Lys Thr Thr Arg Asp Arg Val Pro Thr Tyr Gln Tyr Asn Met Asn Phe
 50                  55                  60

Glu Lys Leu Gly Lys Cys Ile Ile Asn Asn Lys Asn Phe Asp Lys
 65                  70                  75                  80

Val Thr Gly Met Gly Val Arg Asn Gly Thr Asp Lys Asp Ala Glu Ala
                85                  90                  95

Leu Phe Lys Cys Phe Arg Ser Leu Gly Phe Asp Val Ile Val Tyr Asn
            100                 105                 110

Asp Cys Ser Cys Ala Lys Met Gln Asp Leu Leu Lys Lys Ala Ser Glu
            115                 120                 125

Glu Asp His Thr Asn Ala Ala Cys Phe Ala Cys Ile Leu Leu Ser His
130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Cys Arg Gly Thr Glu Leu Asp
            180                 185                 190

Asp Gly Ile Gln Ala Asp Ser Gly Pro Ile Asn Asp Ala Asp Ala Asn
            195                 200                 205

Pro Arg Tyr Lys Ile Pro Val Glu Ala Asp Phe Leu Phe Ala Tyr Ser
        210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255

Glu Ile Met Gln Ile Leu Thr Arg Val Asn Asp Arg Val Ala Arg His
            260                 265                 270

Phe Glu Ser Gln Ser Asp Asp Pro His Phe His Glu Lys Lys Gln Ile
        275                 280                 285

Pro Cys Val Val Ser Met Leu Thr Lys Glu Leu Tyr Phe Ser Gln
    290                 295                 300

<210> SEQ ID NO 20
<211> LENGTH: 936
<212> TYPE: DNA
<213> ORGANISM: Homo sapiens
<220> FEATURE:
<221> NAME/KEY: CDS
<222> LOCATION: (1)..(936)
<223> OTHER INFORMATION: Procaspase-7 DTD wild-type safety catch, active
      site C to A mutant sequence

<400> SEQUENCE: 20 atg gca gat gat cag ggc tgt att gaa gag cag ggg gtt gag gat tca    48
Met Ala Asp Asp Gln Gly Cys Ile Glu Glu Gln Gly Val Glu Asp Ser
1               5                   10                  15 gca aat gaa gat tca gtg gat gct aag cca gac cgg tcc tcg ttt gta    96
Ala Asn Glu Asp Ser Val Asp Ala Lys Pro Asp Arg Ser Ser Phe Val
            20                  25                  30

| | | | | | | | | | | | | | | | | |
|---|---|---|---|---|---|---|---|---|---|---|---|---|---|---|---|---|
| ccg | tcc | ctc | ttc | agt | aag | aag | aag | aaa | aat | gtc | acc | atg | cga | tcc | atc | 144 |
| Pro | Ser | Leu | Phe | Ser | Lys | Lys | Lys | Lys | Asn | Val | Thr | Met | Arg | Ser | Ile | |
| | | 35 | | | | 40 | | | | 45 | | | | | | |
| aag | acc | acc | cgg | gac | cga | gtg | cct | aca | tat | cag | tac | aac | atg | aat | ttt | 192 |
| Lys | Thr | Thr | Arg | Asp | Arg | Val | Pro | Thr | Tyr | Gln | Tyr | Asn | Met | Asn | Phe | |
| | 50 | | | | 55 | | | | 60 | | | | | | | |
| gaa | aag | ctg | ggc | aaa | tgc | atc | ata | ata | aac | aac | aag | aac | ttt | gat | aaa | 240 |
| Glu | Lys | Leu | Gly | Lys | Cys | Ile | Ile | Ile | Asn | Asn | Lys | Asn | Phe | Asp | Lys | |
| 65 | | | | 70 | | | | 75 | | | | 80 | | | | |
| gtg | aca | ggt | atg | ggc | gtt | cga | aac | gga | aca | gac | aaa | gat | gcc | gag | gcg | 288 |
| Val | Thr | Gly | Met | Gly | Val | Arg | Asn | Gly | Thr | Asp | Lys | Asp | Ala | Glu | Ala | |
| | | | | 85 | | | | 90 | | | | 95 | | | | |
| ctc | ttc | aag | tgc | ttc | cga | agc | ctg | ggt | ttt | gac | gtg | att | gtc | tat | aat | 336 |
| Leu | Phe | Lys | Cys | Phe | Arg | Ser | Leu | Gly | Phe | Asp | Val | Ile | Val | Tyr | Asn | |
| | | 100 | | | | 105 | | | | 110 | | | | | | |
| gac | tgc | tct | tgt | gcc | aag | atg | caa | gat | ctg | ctt | aaa | aaa | gct | tct | gaa | 384 |
| Asp | Cys | Ser | Cys | Ala | Lys | Met | Gln | Asp | Leu | Leu | Lys | Lys | Ala | Ser | Glu | |
| | | 115 | | | | 120 | | | | 125 | | | | | | |
| gag | gac | cat | aca | aat | gcc | gcc | tgc | ttc | gcc | tgc | atc | ctc | tta | agc | cat | 432 |
| Glu | Asp | His | Thr | Asn | Ala | Ala | Cys | Phe | Ala | Cys | Ile | Leu | Leu | Ser | His | |
| | 130 | | | | 135 | | | | 140 | | | | | | | |
| gga | gaa | gaa | aat | gta | att | tat | ggg | aaa | gat | ggt | gtc | aca | cca | ata | aag | 480 |
| Gly | Glu | Glu | Asn | Val | Ile | Tyr | Gly | Lys | Asp | Gly | Val | Thr | Pro | Ile | Lys | |
| 145 | | | | 150 | | | | 155 | | | | 160 | | | | |
| gat | ttg | aca | gcc | cac | ttt | agg | ggg | gat | aga | tgc | aaa | acc | ctt | tta | gag | 528 |
| Asp | Leu | Thr | Ala | His | Phe | Arg | Gly | Asp | Arg | Cys | Lys | Thr | Leu | Leu | Glu | |
| | | | | 165 | | | | 170 | | | | 175 | | | | |
| aaa | ccc | aaa | ctc | ttc | ttc | att | cag | gct | gcc | cga | ggg | acc | gag | ctt | gat | 576 |
| Lys | Pro | Lys | Leu | Phe | Phe | Ile | Gln | Ala | Ala | Arg | Gly | Thr | Glu | Leu | Asp | |
| | | 180 | | | | 185 | | | | 190 | | | | | | |
| gat | ggc | atc | cag | gcc | gac | tcg | ggg | ccc | atc | aat | gac | aca | gat | gct | aat | 624 |
| Asp | Gly | Ile | Gln | Ala | Asp | Ser | Gly | Pro | Ile | Asn | Asp | Thr | Asp | Ala | Asn | |
| | | 195 | | | | 200 | | | | 205 | | | | | | |
| cct | cga | tac | aag | atc | cca | gtg | gaa | gct | gac | ttc | ctc | ttc | gcc | tat | tcc | 672 |
| Pro | Arg | Tyr | Lys | Ile | Pro | Val | Glu | Ala | Asp | Phe | Leu | Phe | Ala | Tyr | Ser | |
| | 210 | | | | 215 | | | | 220 | | | | | | | |
| acg | gtt | cca | ggc | tat | tac | tcg | tgg | agg | agc | cca | gga | aga | ggc | tcc | tgg | 720 |
| Thr | Val | Pro | Gly | Tyr | Tyr | Ser | Trp | Arg | Ser | Pro | Gly | Arg | Gly | Ser | Trp | |
| 225 | | | | 230 | | | | 235 | | | | 240 | | | | |
| ttt | gtg | caa | gcc | ctc | tgc | tcc | atc | ctg | gag | gag | cac | gga | aaa | gac | ctg | 768 |
| Phe | Val | Gln | Ala | Leu | Cys | Ser | Ile | Leu | Glu | Glu | His | Gly | Lys | Asp | Leu | |
| | | | | 245 | | | | 250 | | | | 255 | | | | |
| gaa | atc | atg | cag | atc | ctc | acc | agg | gtg | aat | gac | aga | gtt | gcc | agg | cac | 816 |
| Glu | Ile | Met | Gln | Ile | Leu | Thr | Arg | Val | Asn | Asp | Arg | Val | Ala | Arg | His | |
| | | | 260 | | | | 265 | | | | 270 | | | | | |
| ttt | gag | tct | cag | tct | gat | gac | cca | cac | ttc | cat | gag | aag | aag | cag | atc | 864 |
| Phe | Glu | Ser | Gln | Ser | Asp | Asp | Pro | His | Phe | His | Glu | Lys | Lys | Gln | Ile | |
| | | 275 | | | | 280 | | | | 285 | | | | | | |
| ccc | tgt | gtg | gtc | tcc | atg | ctc | acc | aag | gaa | ctc | tac | ttc | agt | caa | ctc | 912 |
| Pro | Cys | Val | Val | Ser | Met | Leu | Thr | Lys | Glu | Leu | Tyr | Phe | Ser | Gln | Leu | |
| | 290 | | | | 295 | | | | 300 | | | | | | | |
| gag | cac | cac | cac | cac | cac | cac | tga | | | | | | | | | 936 |
| Glu | His | His | His | His | His | His | | | | | | | | | | |
| 305 | | | | 310 | | | | | | | | | | | | |

```
<210> SEQ ID NO 21
<211> LENGTH: 311
<212> TYPE: PRT
<213> ORGANISM: Homo sapiens

<400> SEQUENCE: 21
```

```
Met Ala Asp Asp Gln Gly Cys Ile Glu Glu Gln Gly Val Glu Asp Ser
1               5                   10                  15

Ala Asn Glu Asp Ser Val Asp Ala Lys Pro Asp Arg Ser Ser Phe Val
            20                  25                  30

Pro Ser Leu Phe Ser Lys Lys Lys Asn Val Thr Met Arg Ser Ile
        35                  40                  45

Lys Thr Thr Arg Asp Arg Val Pro Thr Tyr Gln Tyr Asn Met Asn Phe
50                  55                  60

Glu Lys Leu Gly Lys Cys Ile Ile Ile Asn Asn Lys Asn Phe Asp Lys
65                  70                  75                  80

Val Thr Gly Met Gly Val Arg Asn Gly Thr Asp Lys Asp Ala Glu Ala
                85                  90                  95

Leu Phe Lys Cys Phe Arg Ser Leu Gly Phe Asp Val Ile Val Tyr Asn
                100                 105                 110

Asp Cys Ser Cys Ala Lys Met Gln Asp Leu Leu Lys Lys Ala Ser Glu
            115                 120                 125

Glu Asp His Thr Asn Ala Ala Cys Phe Ala Cys Ile Leu Leu Ser His
    130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Ala Arg Gly Thr Glu Leu Asp
            180                 185                 190

Asp Gly Ile Gln Ala Asp Ser Gly Pro Ile Asn Asp Thr Asp Ala Asn
        195                 200                 205

Pro Arg Tyr Lys Ile Pro Val Glu Ala Asp Phe Leu Phe Ala Tyr Ser
210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255

Glu Ile Met Gln Ile Leu Thr Arg Val Asn Asp Arg Val Ala Arg His
            260                 265                 270

Phe Glu Ser Gln Ser Asp Asp Pro His Phe His Glu Lys Lys Gln Ile
        275                 280                 285

Pro Cys Val Val Ser Met Leu Thr Lys Glu Leu Tyr Phe Ser Gln Leu
290                 295                 300

Glu His His His His His His
305                 310

<210> SEQ ID NO 22
<211> LENGTH: 936
<212> TYPE: DNA
<213> ORGANISM: Homo sapiens
<220> FEATURE:
<221> NAME/KEY: CDS
<222> LOCATION: (1)..(936)
<223> OTHER INFORMATION: Procaspase-7 DDD wild-type safety catch, active
      site C to A mutant sequence

<400> SEQUENCE: 22 atg gca gat gat cag ggc tgt att gaa gag cag ggg gtt gag gat tca      48
Met Ala Asp Asp Gln Gly Cys Ile Glu Glu Gln Gly Val Glu Asp Ser
1               5                   10                  15 gca aat gaa gat tca gtg gat gct aag cca gac cgg tcc tcg ttt gta     96
Ala Asn Glu Asp Ser Val Asp Ala Lys Pro Asp Arg Ser Ser Phe Val
```

```
                  20                  25                  30
ccg tcc ctc ttc agt aag aag aag aaa aat gtc acc atg cga tcc atc        144
Pro Ser Leu Phe Ser Lys Lys Lys Lys Asn Val Thr Met Arg Ser Ile
         35                  40                  45 aag acc acc cgg gac cga gtg cct aca tat cag tac aac atg aat ttt        192
Lys Thr Thr Arg Asp Arg Val Pro Thr Tyr Gln Tyr Asn Met Asn Phe
 50                  55                  60 gaa aag ctg ggc aaa tgc atc ata ata aac aac aag aac ttt gat aaa        240
Glu Lys Leu Gly Lys Cys Ile Ile Ile Asn Asn Lys Asn Phe Asp Lys
 65                  70                  75                  80 gtg aca ggt atg ggc gtt cga aac gga aca gac aaa gat gcc gag gcg        288
Val Thr Gly Met Gly Val Arg Asn Gly Thr Asp Lys Asp Ala Glu Ala
                 85                  90                  95 ctc ttc aag tgc ttc cga agc ctg ggt ttt gac gtg att gtc tat aat        336
Leu Phe Lys Cys Phe Arg Ser Leu Gly Phe Asp Val Ile Val Tyr Asn
                100                 105                 110 gac tgc tct tgt gcc aag atg caa gat ctg ctt aaa aaa gct tct gaa        384
Asp Cys Ser Cys Ala Lys Met Gln Asp Leu Leu Lys Lys Ala Ser Glu
            115                 120                 125 gag gac cat aca aat gcc gcc tgc ttc gcc tgc atc ctc tta agc cat        432
Glu Asp His Thr Asn Ala Ala Cys Phe Ala Cys Ile Leu Leu Ser His
130                 135                 140 gga gaa gaa aat gta att tat ggg aaa gat ggt gtc aca cca ata aag        480
Gly Glu Glu Asn Val Ile Tyr Gly Lys Asp Gly Val Thr Pro Ile Lys
145                 150                 155                 160 gat ttg aca gcc cac ttt agg ggg gat aga tgc aaa acc ctt tta gag        528
Asp Leu Thr Ala His Phe Arg Gly Asp Arg Cys Lys Thr Leu Leu Glu
                165                 170                 175 aaa ccc aaa ctc ttc ttc att cag gct gcc cga ggg acc gag ctt gat        576
Lys Pro Lys Leu Phe Phe Ile Gln Ala Ala Arg Gly Thr Glu Leu Asp
            180                 185                 190 gat ggc atc cag gcc gac tcg ggg ccc atc aat gac gca gat gct aat        624
Asp Gly Ile Gln Ala Asp Ser Gly Pro Ile Asn Asp Ala Asp Ala Asn
        195                 200                 205 cct cga tac aag atc cca gtg gaa gct gac ttc ctc ttc gcc tat tcc        672
Pro Arg Tyr Lys Ile Pro Val Glu Ala Asp Phe Leu Phe Ala Tyr Ser
    210                 215                 220 acg gtt cca ggc tat tac tcg tgg agg agc cca gga aga ggc tcc tgg        720
Thr Val Pro Gly Tyr Tyr Ser Trp Arg Ser Pro Gly Arg Gly Ser Trp
225                 230                 235                 240 ttt gtg caa gcc ctc tgc tcc atc ctg gag gag cac gga aaa gac ctg        768
Phe Val Gln Ala Leu Cys Ser Ile Leu Glu Glu His Gly Lys Asp Leu
                245                 250                 255 gaa atc atg cag atc ctc acc agg gtg aat gac aga gtt gcc agg cac        816
Glu Ile Met Gln Ile Leu Thr Arg Val Asn Asp Arg Val Ala Arg His
            260                 265                 270 ttt gag tct cag tct gat gac cca cac ttc cat gag aag aag cag atc        864
Phe Glu Ser Gln Ser Asp Asp Pro His Phe His Glu Lys Lys Gln Ile
        275                 280                 285 ccc tgt gtg gtc tcc atg ctc acc aag gaa ctc tac ttc agt caa ctc        912
Pro Cys Val Val Ser Met Leu Thr Lys Glu Leu Tyr Phe Ser Gln Leu
    290                 295                 300 gag cac cac cac cac cac cac tga                                        936
Glu His His His His His His
305                 310

<210> SEQ ID NO 23
<211> LENGTH: 311
<212> TYPE: PRT
<213> ORGANISM: Homo sapiens
```

-continued

```
<400> SEQUENCE: 23

Met Ala Asp Asp Gln Gly Cys Ile Glu Glu Gln Gly Val Glu Asp Ser
1               5                   10                  15

Ala Asn Glu Asp Ser Val Asp Ala Lys Pro Asp Arg Ser Ser Phe Val
            20                  25                  30

Pro Ser Leu Phe Ser Lys Lys Lys Asn Val Thr Met Arg Ser Ile
        35                  40                  45

Lys Thr Thr Arg Asp Arg Val Pro Thr Tyr Gln Tyr Asn Met Asn Phe
50                  55                  60

Glu Lys Leu Gly Lys Cys Ile Ile Ile Asn Asn Lys Asn Phe Asp Lys
65                  70                  75                  80

Val Thr Gly Met Gly Val Arg Asn Gly Thr Asp Lys Asp Ala Glu Ala
                85                  90                  95

Leu Phe Lys Cys Phe Arg Ser Leu Gly Phe Asp Val Ile Val Tyr Asn
            100                 105                 110

Asp Cys Ser Cys Ala Lys Met Gln Asp Leu Leu Lys Lys Ala Ser Glu
            115                 120                 125

Glu Asp His Thr Asn Ala Ala Cys Phe Ala Cys Ile Leu Leu Ser His
        130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Ala Arg Gly Thr Glu Leu Asp
            180                 185                 190

Asp Gly Ile Gln Ala Asp Ser Gly Pro Ile Asn Asp Ala Asp Ala Asn
        195                 200                 205

Pro Arg Tyr Lys Ile Pro Val Glu Ala Asp Phe Leu Phe Ala Tyr Ser
210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255

Glu Ile Met Gln Ile Leu Thr Arg Val Asn Asp Arg Val Ala Arg His
            260                 265                 270

Phe Glu Ser Gln Ser Asp Asp Pro His Phe His Glu Lys Lys Gln Ile
        275                 280                 285

Pro Cys Val Val Ser Met Leu Thr Lys Glu Leu Tyr Phe Ser Gln Leu
290                 295                 300

Glu His His His His His His
305                 310

<210> SEQ ID NO 24
<211> LENGTH: 303
<212> TYPE: PRT
<213> ORGANISM: Homo sapiens
<220> FEATURE:
<221> NAME/KEY: MISC_FEATURE
<222> LOCATION: (1)..(303)
<223> OTHER INFORMATION: Procaspase-7 with amino acid DTD wild-type
      safety catch sequence (Accession Number NM_001227)

<400> SEQUENCE: 24

Met Ala Asp Asp Gln Gly Cys Ile Glu Glu Gln Gly Val Glu Asp Ser
1               5                   10                  15

Ala Asn Glu Asp Ser Val Asp Ala Lys Pro Asp Arg Ser Ser Phe Val
            20                  25                  30
```

```
Pro Ser Leu Phe Ser Lys Lys Lys Asn Val Thr Met Arg Ser Ile
         35                  40                  45

Lys Thr Thr Arg Asp Arg Val Pro Thr Tyr Gln Tyr Asn Met Asn Phe
 50                  55                  60

Glu Lys Leu Gly Lys Cys Ile Ile Ile Asn Asn Lys Asn Phe Asp Lys
 65                  70                  75                  80

Val Thr Gly Met Gly Val Arg Asn Gly Thr Asp Lys Asp Ala Glu Ala
                 85                  90                  95

Leu Phe Lys Cys Phe Arg Ser Leu Gly Phe Asp Val Ile Val Tyr Asn
                100                 105                 110

Asp Cys Ser Cys Ala Lys Met Gln Asp Leu Leu Lys Lys Ala Ser Glu
                115                 120                 125

Glu Asp His Thr Asn Ala Ala Cys Phe Ala Cys Ile Leu Leu Ser His
130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Cys Arg Gly Thr Glu Leu Asp
                180                 185                 190

Asp Gly Ile Gln Ala Asp Ser Gly Pro Ile Asn Asp Thr Asp Ala Asn
                195                 200                 205

Pro Arg Tyr Lys Ile Pro Val Glu Ala Asp Phe Leu Phe Ala Tyr Ser
210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255

Glu Ile Met Gln Ile Leu Thr Arg Val Asn Asp Arg Val Ala Arg His
                260                 265                 270

Phe Glu Ser Gln Ser Asp Asp Pro His Phe His Glu Lys Lys Gln Ile
                275                 280                 285

Pro Cys Val Val Ser Met Leu Thr Lys Glu Leu Tyr Phe Ser Gln
                290                 295                 300

<210> SEQ ID NO 25
<211> LENGTH: 303
<212> TYPE: PRT
<213> ORGANISM: Homo sapiens
<220> FEATURE:
<221> NAME/KEY: MISC_FEATURE
<222> LOCATION: (1)..(303)
<223> OTHER INFORMATION: Procaspase-7 DDD wild-type safety catch
      sequence

<400> SEQUENCE: 25

Met Ala Asp Asp Gln Gly Cys Ile Glu Glu Gly Val Glu Asp Ser
 1                5                  10                  15

Ala Asn Glu Asp Ser Val Asp Ala Lys Pro Asp Arg Ser Ser Phe Val
                 20                  25                  30

Pro Ser Leu Phe Ser Lys Lys Lys Asn Val Thr Met Arg Ser Ile
         35                  40                  45

Lys Thr Thr Arg Asp Arg Val Pro Thr Tyr Gln Tyr Asn Met Asn Phe
 50                  55                  60

Glu Lys Leu Gly Lys Cys Ile Ile Ile Asn Asn Lys Asn Phe Asp Lys
 65                  70                  75                  80
```

```
Val Thr Gly Met Gly Val Arg Asn Gly Thr Asp Lys Asp Ala Glu Ala
            85                  90                  95
Leu Phe Lys Cys Phe Arg Ser Leu Gly Phe Asp Val Ile Val Tyr Asn
            100                 105                 110
Asp Cys Ser Cys Ala Lys Met Gln Asp Leu Leu Lys Lys Ala Ser Glu
            115                 120                 125
Glu Asp His Thr Asn Ala Ala Cys Phe Ala Cys Ile Leu Leu Ser His
            130                 135                 140
Gly Glu Glu Asn Val Ile Tyr Gly Lys Asp Gly Val Thr Pro Ile Lys
145                 150                 155                 160
Asp Leu Thr Ala His Phe Arg Gly Asp Arg Cys Lys Thr Leu Leu Glu
            165                 170                 175
Lys Pro Lys Leu Phe Phe Ile Gln Ala Cys Arg Gly Thr Glu Leu Asp
            180                 185                 190
Asp Gly Ile Gln Ala Asp Ser Gly Pro Ile Asn Asp Asp Ala Asn
            195                 200                 205
Pro Arg Tyr Lys Ile Pro Val Glu Ala Asp Phe Leu Phe Ala Tyr Ser
            210                 215                 220
Thr Val Pro Gly Tyr Tyr Ser Trp Arg Ser Pro Gly Arg Gly Ser Trp
225                 230                 235                 240
Phe Val Gln Ala Leu Cys Ser Ile Leu Glu Glu His Gly Lys Asp Leu
            245                 250                 255
Glu Ile Met Gln Ile Leu Thr Arg Val Asn Asp Arg Val Ala Arg His
            260                 265                 270
Phe Glu Ser Gln Ser Asp Asp Pro His Phe His Glu Lys Lys Gln Ile
            275                 280                 285
Pro Cys Val Val Ser Met Leu Thr Lys Glu Leu Tyr Phe Ser Gln
            290                 295                 300

<210> SEQ ID NO 26
<211> LENGTH: 303
<212> TYPE: PRT
<213> ORGANISM: Homo sapiens
<220> FEATURE:
<221> NAME/KEY: MISC_FEATURE
<222> LOCATION: (1)..(303)
<223> OTHER INFORMATION: Procaspase-7 DTD wild-type safety catch, active
      site C to A mutant sequence

<400> SEQUENCE: 26

Met Ala Asp Asp Gln Gly Cys Ile Glu Glu Gln Gly Val Glu Asp Ser
1               5                   10                  15
Ala Asn Glu Asp Ser Val Asp Ala Lys Pro Asp Arg Ser Ser Phe Val
            20                  25                  30
Pro Ser Leu Phe Ser Lys Lys Lys Asn Val Thr Met Arg Ser Ile
            35                  40                  45
Lys Thr Thr Arg Asp Arg Val Pro Thr Tyr Gln Tyr Asn Met Asn Phe
50                  55                  60
Glu Lys Leu Gly Lys Cys Ile Ile Ile Asn Asn Lys Asn Phe Asp Lys
65                  70                  75                  80
Val Thr Gly Met Gly Val Arg Asn Gly Thr Asp Lys Asp Ala Glu Ala
            85                  90                  95
Leu Phe Lys Cys Phe Arg Ser Leu Gly Phe Asp Val Ile Val Tyr Asn
            100                 105                 110
Asp Cys Ser Cys Ala Lys Met Gln Asp Leu Leu Lys Lys Ala Ser Glu
            115                 120                 125
Glu Asp His Thr Asn Ala Ala Cys Phe Ala Cys Ile Leu Leu Ser His
```

```
            130                 135                 140
Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Ala Arg Gly Thr Glu Leu Asp
            180                 185                 190

Asp Gly Ile Gln Ala Asp Ser Gly Pro Ile Asn Asp Thr Asp Ala Asn
            195                 200                 205

Pro Arg Tyr Lys Ile Pro Val Glu Ala Asp Phe Leu Phe Ala Tyr Ser
210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255

Glu Ile Met Gln Ile Leu Thr Arg Val Asn Asp Arg Val Ala Arg His
            260                 265                 270

Phe Glu Ser Gln Ser Asp Asp Pro His Phe His Glu Lys Lys Gln Ile
            275                 280                 285

Pro Cys Val Val Ser Met Leu Thr Lys Glu Leu Tyr Phe Ser Gln
            290                 295                 300
```

<210> SEQ ID NO 27
<211> LENGTH: 303
<212> TYPE: PRT
<213> ORGANISM: Homo sapiens
<220> FEATURE:
<221> NAME/KEY: MISC_FEATURE
<222> LOCATION: (1)..(303)
<223> OTHER INFORMATION: Procaspase-7 DDD wild-type safety catch, active
      site C to A mutant sequence

<400> SEQUENCE: 27

```
Met Ala Asp Asp Gln Gly Cys Ile Glu Glu Gln Gly Val Glu Asp Ser
1               5                   10                  15

Ala Asn Glu Asp Ser Val Asp Ala Lys Pro Asp Arg Ser Ser Phe Val
                20                  25                  30

Pro Ser Leu Phe Ser Lys Lys Lys Lys Asn Val Thr Met Arg Ser Ile
            35                  40                  45

Lys Thr Thr Arg Asp Arg Val Pro Thr Tyr Gln Tyr Asn Met Asn Phe
50                  55                  60

Glu Lys Leu Gly Lys Cys Ile Ile Ile Asn Asn Lys Asn Phe Asp Lys
65                  70                  75                  80

Val Thr Gly Met Gly Val Arg Asn Gly Thr Asp Lys Asp Ala Glu Ala
                85                  90                  95

Leu Phe Lys Cys Phe Arg Ser Leu Gly Phe Asp Val Ile Val Tyr Asn
            100                 105                 110

Asp Cys Ser Cys Ala Lys Met Gln Asp Leu Leu Lys Lys Ala Ser Glu
            115                 120                 125

Glu Asp His Thr Asn Ala Ala Cys Phe Ala Cys Ile Leu Leu Ser His
            130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Ala Arg Gly Thr Glu Leu Asp
            180                 185                 190
```

```
Asp Gly Ile Gln Ala Asp Ser Gly Pro Ile Asn Asp Asp Ala Asn
        195                 200                 205
Pro Arg Tyr Lys Ile Pro Val Glu Ala Asp Phe Leu Phe Ala Tyr Ser
        210                 215                 220
Thr Val Pro Gly Tyr Tyr Ser Trp Arg Ser Pro Gly Arg Gly Ser Trp
225                 230                 235                 240
Phe Val Gln Ala Leu Cys Ser Ile Leu Glu Glu His Gly Lys Asp Leu
                245                 250                 255
Glu Ile Met Gln Ile Leu Thr Arg Val Asn Asp Arg Val Ala Arg His
                260                 265                 270
Phe Glu Ser Gln Ser Asp Asp Pro His Phe His Glu Lys Lys Gln Ile
            275                 280                 285
Pro Cys Val Val Ser Met Leu Thr Lys Glu Leu Tyr Phe Ser Gln
        290                 295                 300
```

COMPOSITIONS AND METHODS INCLUDING CELL DEATH INDUCERS AND PROCASPASE ACTIVATION

CROSS-REFERENCES TO RELATED APPLICATIONS

This application is a continuation of U.S. patent application Ser. No. 12/597,287, filed Oct. 23, 2009, which is the U.S. National Stage of PCT International Application No. PCT/US2008/061510, filed Apr. 25, 2008, which claims the benefit of U.S. provisional application 60/914,592, filed Apr. 27, 2007, and is a continuation-in-part of U.S. patent application Ser. No. 11/420,425, filed May 25, 2006, which claims the benefit of U.S. Provisional Patent Application Ser. No. 60/684,807, filed May 26, 2005 and U.S. Provisional Patent Application Ser. No. 60/743,878, filed Mar. 28, 2006; all of which are is incorporated by reference in its entirety herein.

STATEMENT ON FEDERALLY SPONSORED RESEARCH OR DEVELOPMENT

Not applicable

BACKGROUND OF THE INVENTION

Apoptosis, or programmed cell death, plays a central role in the development and homeostasis of all multicellular organisms (Shi Y, 2002, Molecular Cell 9:459-470). A frequent hallmark of cancer is resistance to natural apoptotic signals. Depending on the cancer type, this resistance is typically due to up- or down-regulation of key proteins in the apoptotic cascade or to mutations in genes encoding these proteins. Such changes occur in both the intrinsic apoptotic pathway, which funnels through the mitochondria and caspase-9, and the extrinsic apoptotic pathway, which involves the action of death receptors and caspase-8. For example, alterations in proper levels of proteins such as p53, Bim, Bax, Apaf-1, FLIP and many others have been observed in cancers. The alterations can lead to a defective apoptotic cascade, one in which the upstream pro-apoptotic signal is not adequately transmitted to activate the executioner caspases, caspase-3 and caspase-7.

As most apoptotic pathways ultimately involve the activation of procaspase-3, upstream genetic abnormalities are effectively "breaks" in the apoptotic circuitry, and as a result such cells proliferate atypically. Given the central role of apoptosis in cancer, efforts have been made to develop therapeutics that target specific proteins in the apoptotic cascade. For instance, peptidic or small molecule binders to cascade members such as p53 and proteins in the Bcl family or to the inhibitor of apoptosis (IAP) family of proteins have pro-apoptotic activity, as do compounds that promote the oligomerization of Apaf-1. However, because such compounds target early (or intermediate to high) positions on the apoptotic cascade, cancers with mutations in proteins downstream of those members can still be resistant to the possible beneficial effects of those compounds.

For therapeutic purposes it would be advantageous to identify a small molecule that directly activates a proapoptotic protein far downstream in the apoptotic cascade. The approach to our invention involves such a relatively low position in the cascade, thus enabling the killing of even those cells that have mutations in their upstream apoptotic machinery. Moreover, the therapeutic strategies disclosed herein can have a higher likelihood of success if that proapoptotic protein were upregulated in cancer cells. In the present invention, our efforts to identify small molecules began with targeting the significant downstream effector protein of apoptosis, procaspase-3.

The conversion or activation of procaspase-3 to caspase-3 results in the generation of the active "executioner" caspase form that subsequently catalyzes the hydrolysis of a multitude of protein substrates. Active caspase-3 is a homodimer of heterodimers and is produced by proteolysis of procaspase-3. In vivo, this proteolytic activation typically occurs through the action of caspase-8 or caspase-9. To ensure that the proenzyme or zymogen is not prematurely activated, procaspase-3 has a 12 amino acid "safety catch" that blocks access to the IETD site (amino acid sequence, ile-glu-thr-asp) of proteolysis. See Roy, S. et al.; Maintenance of caspase-3 proenzyme dormancy by an intrinsic "safety catch" regulatory tripeptide, Proc. Natl. Acad. Sci. 98, 6132-6137 (2001).

This safety catch enables procaspase-3 to resist autocatalytic activation and proteolysis by caspase-9. Mutagenic studies indicate that three consecutive aspartic acid residues appear to be the critical components of the safety catch. The position of the safety catch is sensitive to pH; thus, upon cellular acidification (as occurs during apoptosis) the safety catch is thought to allow access to the site of proteolysis, and active caspase-3 can be produced either by the action of caspase-9 or through an autoactivation mechanism.

In particular cancers, the expression of procaspase-3 is upregulated. A study of primary isolates from 20 colon cancer patients revealed that on average, procaspase-3 was upregulated six-fold in such isolates relative to adjacent non-cancerous tissue (Roy et al., 2001). In addition, procaspase-3 is upregulated in certain neuroblastomas, lymphomas, and liver cancers (Nakagawara, A. et al., 1997, Cancer Res. 57:4578-4584; Izban, K. F. et al., Am. J. Pathol. 154:1439-1447; Persad, R. et al., Modern Patholo. 17:861-867). Furthermore, a systematic evaluation was performed of procaspase-3 levels in the 60 cell-line panel used for cancer screening by the National Cancer Institute (NCI) Developmental Therapeutics Program. The evaluation revealed that certain lung, melanoma, renal, and breast cancers show greatly enhanced levels of procaspase-3 expression (Svingen, P. A. et al., Clin. Cancer Res. 10:6807-6820).

Due to the role of active caspase-3 in achieving apoptosis, the relatively high expression levels of procaspase-3 in certain cancerous cell types, and the intriguing safety catch-mediated suppression of its autoactivation, we reasoned that small molecules that directly modify procaspase-3 could be identified and that such molecules could have great applicability in targeted cancer therapy.

Herein we disclose, inter alia, compositions and methods including small molecules capable of inducing cell death. In embodiments, compositions and methods involve compounds which can interact directly or indirectly with programmed cell death pathway members such as procaspase-3.

U.S. Provisional Application Ser. 60/684,807 filed May 26, 2005; U.S. Provisional Application Ser. 60/743,878 filed Mar. 28, 2006; U.S. patent application Ser. No. 11/420,425 filed May 25, 2006 (published as US 20070049602, Mar. 1, 2007); PCT International Application Serial PCT/US 06/020910 filed May 26, 2006 (published as WO2006/128173, 30 Nov. 2006), which are incorporated by reference herein, relate to the subject matter of the present application.

SUMMARY OF THE INVENTION

The invention broadly provides compounds, methods of therapeutic treatment, methods of screening for compounds, and methods of screening for cell and patient suitability for treatment in connection with modifiers of procaspases. In an embodiment, the modifiers are inhibitors. In an embodiment, the modifiers are activators. In an embodiment, the invention provides such compounds and methods in connection with activators of procaspase-3 and procaspase-7. In embodiments, the inventions are applicable in the context of a variety of cancer diseases and cancer cell types such as breast, lymphoma, adrenal, renal, melanoma, leukemia, neuroblastoma, lung, brain, and others known in the art.

As a further introduction, compounds capable of activating an enzyme that is often overexpressed in its inactive form in cancer cells have been discovered. The compound induces programmed cell death (apoptosis) in cancer cells, including those that have upregulated procaspase-3. Many cancers resist standard chemotherapy. Compounds of the invention can take advantage of a biological target that may be upregulated in cancer cells and thus can prove effective even in cells with defects in their apoptotic machinery. These compounds can also be successful in targeted cancer therapy, where there can be advantages of selectivity in the killing of cancer cells with comparably reduced toxicity to non-cancerous cells having lower levels of procaspase-3.

Without wishing to be bound by a particular theory, it is believed that embodiments of compounds and methods of the invention may act via the mechanism of modulation of apoptosis or programmed cell death to be effective in the treatment of cancer cells. In a preferred embodiment, the modulation of apoptosis is by induction of apoptosis. In another embodiment, the modulation of apoptosis is by inhibition of apoptosis.

In an embodiment, the invention provides a method of selectively inducing apoptosis in a cancer cell, comprising: (a) administering to said cancer cell an effective amount of a compound capable of modifying a procaspase-3 molecule of said cancer cell; and (b) modifying said procaspase-3 molecule so as to induce apoptosis. In an embodiment, said cancer cell is in a patient in need of treatment.

In an embodiment, compounds and methods may act indirectly in connection with a programmed cell death pathway member, e.g., procaspase-3, such as by chelating or otherwise interacting directly or indirectly with a molecule which is necessary for the pathway member. In an embodiment the molecule is a metal such as zinc.

In an embodiment, said compound is of formula Z:

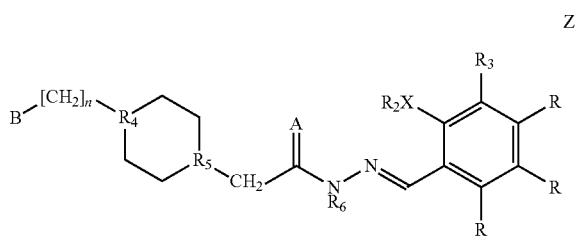

Z and salts thereof,
wherein n=0, 1 or 2;
each R, independently of other R, is selected from hydrogen, halogen, alkyl, alkoxy or alkenyl;
$R_2X$ is a halogen or X is O, S, $NR_7$, CO, OCO, or OCS, when X is O or S, $R_2$=hydrogen, alkyl, aryl, $R_8$CO—, $R_8$OCO—, $R_8$SCO, $R_8$OCS— or a moiety that is removable under physiological conditions, where $R_5$ is alkyl or aryl, when X is $NR_7$, $R_2$ and $R_7$, independently, are selected from hydrogen, alkyl, aryl, $R_8$CO—, $R_8$OCO—, or a moiety that is removable under physiological conditions; when X is CO, OCO or OCS, $R_2$ is hydrogen, alkyl, aryl, or a moiety that is removable under physiological conditions;
$R_3$ is selected from hydrogen, halogen, alkyl, haloalkyl, alkenyl, alkenol, alkanol, or haloalkenyl;
$R_4$ and $R_5$ are both N; $R_4$ is N and $R_5$ is CH; $R_4$ is CH and $R_5$ is N or $R_4$ and $R_5$ are both CH;
$R_6$ is hydrogen or alkyl;
A=oxygen or sulfur; and
B is aryl, heteroaryl or $R_9$—O—CO—, where $R_9$ is alkyl or aryl.

In a more specific embodiment of formula Z, $R_3$ is allyl. In another embodiment of formula Z, $R_2X$ is OH. In another embodiment of formula Z, $R_2X$ is $NH_2$. In specific embodiments, aryl groups are phenyl groups substituted with one or more R groups as defined above. In specific embodiments, alkyl groups are C1-C6 alkyl groups or C1-C3 alkyl groups. In specific embodiments, alkenyl groups are C2-C6 alkenyl groups or C2-C4 alkenyl groups. In specific embodiments, alkenyl groups are allyl groups. In specific embodiments of formula Z, B is a $R_9$—O—CO—. In specific embodiments of formula Z, B is a phenyl substituted with one or more R substituents. In specific embodiments of formula Z, $R_9$ is a t-butyl group. In specific embodiments, $R_6$ is hydrogen or methyl. In specific embodiments, n is 0 and B is $R_9$—O—CO—. In specific embodiments, n is 1 or 2 and B is aryl. In a specific embodiment, A is O. In a specific embodiment, R is hydrogen. In a specific embodiment of formula Z, at least one R or $R_3$ is a substituent other than hydrogen. In a specific embodiment of formula Z, at least one R is a substituent other than hydrogen. In a specific embodiment of formula Z, $R_2X$ is OH and $R_3$ is allyl. In a specific embodiment of formula Z, n is 1 and B is pyridinyl. In a specific embodiment of formula Z, n is 1 and B is 2-pyridinyl. In a specific embodiment of formula Z, n is 1 and B is 3-pyridinyl. In a specific embodiment of formula Z, n is 1 and B is 4-pyridinyl. In specific embodiments of formula Z, n is 0 and B is $R_9$—OCO— and $R_9$ is alkyl. In specific embodiments of formula Z, n is 0 and B is $R_9$—OCO— and $R_9$ is t-butyl.

In an embodiment, said compound is of formula ZA:

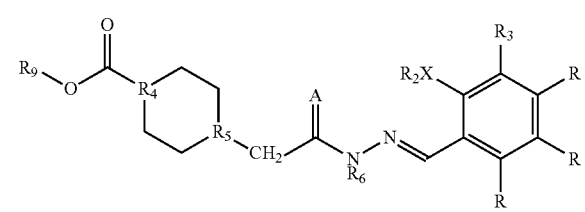

ZA and salts thereof;
wherein each R, independently of other R, is selected from hydrogen, halogen, alkyl, or alkenyl;
$R_2X$ is a halogen or X is O, S, $NR_7$, CO, OCO, or OCS, when X is O or S, $R_2$=hydrogen, alkyl, aryl, $R_8$CO—, $R_8$OCO—, $R_8$SCO, $R_8$OCS— or a moiety that is removable under physiological conditions, where $R_8$ is alkyl or aryl, when X is $NR_7$, $R_2$ and $R_7$, independently, are selected from hydrogen, alkyl, aryl, $R_8$CO—, $R_8$OCO—, or a moiety that is removable under physiological conditions; when X is CO, OCO or OCS, $R_2$ is hydrogen, alkyl, aryl, or a moiety that is removable under physiological conditions;
$R_3$ is selected from hydrogen, halogen, alkyl, haloalkyl, alkenyl, alkenol, alkanol, or haloalkenyl;

$R_4$ and $R_5$ are both N; $R_4$ is N and $R_5$ is CH; $R_4$ is CH and $R_5$ is N or $R_4$ and $R_5$ are both CH;

$R_6$ is hydrogen or alkyl;

A=oxygen or sulfur; and $R_9$ is alkyl or aryl.

In a more specific embodiment of formula ZA, $R_3$ is allyl. In specific embodiments of formula ZA, $R_9$ is an alkyl group. In specific embodiments of formula ZA, $R_9$ is an C1-C6 alkyl group. In specific embodiments, $R_9$ is a t-butyl group. In another embodiment of formula ZA, $R_2X$ is OH. In another embodiment of formula ZA, $R_2X$ is $NH_2$. In specific embodiments of formula ZA, aryl groups are phenyl groups substituted with one or more R groups as defined above. In specific embodiments of formula ZA, alkyl groups are C1-C6 alkyl groups or C1-C3 alkyl groups. In specific embodiments of formula ZA, alkenyl groups are C2-C6 alkenyl groups or C2-C4 alkenyl groups. In specific embodiments of formula ZA, alkenyl groups are allyl groups. In specific embodiments of formula ZA, $R_6$ is hydrogen or methyl. In a specific embodiment of formula ZA, A is O. In a specific embodiment of formula ZA, R is hydrogen. In a specific embodiment of formula ZA, at least one R or $R_3$ is a substituent other than hydrogen. In a specific embodiment of formula ZA, at least one R is a substituent other than hydrogen. In a specific embodiment of formula ZA, $R_2X$ is OH and $R_3$ is allyl.

In an embodiment, said compound is of formula ZZ:

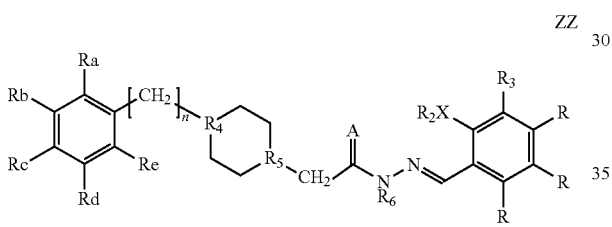

ZZ and salts thereof, wherein n=1 or 2; Ra, Rb, Rc, Rd, and Re are independently selected from hydrogen, halogen, alkyl, alkenyl, alkoxy, and aryl and other variables are as defined in formula Z.

In a specific embodiment of formula ZZ, n is 1. In a specific embodiment of formula ZZ, $R_2X$ is OH. In a specific embodiment of formula ZZ, $R_2X$ is $NH_2$. In a specific embodiment of formula ZZ, A is O. In a specific embodiment of formula ZZ, $R_3$ is allyl. In a specific embodiment of formula ZZ, $R_6$ is hydrogen. In a specific embodiment of formula ZZ, R is hydrogen. In a specific embodiment of formula ZZ, one or two of Ra, Rb, Rc, Rd and Re are C1-C3 alkyl, C1-C3 alkoxy or halogens and the remaining groups are hydrogens. In a specific embodiment, Rc is a C1-C3 alkyl or a C1-C3 alkoxy and Ra, Rb, Rd, and Re are all hydrogens. In a specific embodiment, all of Ra, Rb, Rc, Rd and Re are hydrogens. In a specific embodiment, Rc is fluorine and Ra, Rb, Rc, Rd and Re are all hydrogens. In a specific embodiment, $R_2X$ is chlorine. In a specific embodiment, $R_2X$ is OH. In a specific embodiment, $R_2X$ is SH. In a specific embodiment, $R_2X$ is $CH_3S$. In a specific embodiment, $R_2X$ is HO—CO—. In a specific embodiment, $R_2X$ is $CH_3O$—CO—.

In additional embodiments of formula ZZ, $R_4$ and $R_5$ are both N, A is oxygen, and other variable groups are as defined above. In an embodiment of formula ZZ, $R_4$ and $R_5$ are both N, A is oxygen, $R_2$ is hydrogen, and other variable groups are as defined above. In an embodiment of formula ZZ, $R_4$ and $R_5$ and both N, A is oxygen, $R_2$ is hydrogen, $R_3$ is allyl, and other variable groups are as defined above. In an embodiment of ZZ, one of R is a fluorine. In a specific embodiment of formula ZZ, at least one R or $R_3$ is a substituent other than hydrogen. In a specific embodiment of formula ZZ, at least one R is a substituent other than hydrogen. In a specific embodiment of formula ZZ, $R_2X$ is OH and $R_3$ is allyl. In a specific embodiment of formula ZZ, at least one of Ra-Re is a substituent other than hydrogen. In a specific embodiment of formula ZZ, at least one R or R3 is a substituent other than hydrogen, and at least one of Ra-Re is a substituent other than hydrogen.

In an embodiment, the invention provides compounds of formula ZB:

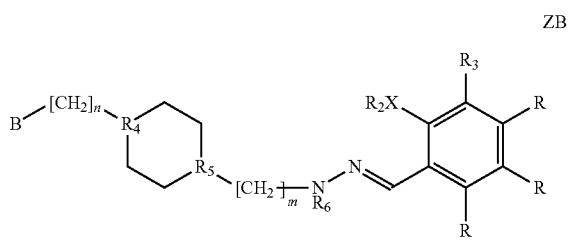

ZB or salts thereof, where m is 1-4 and other variables are as defined for formula Z. In specific embodiments of formula ZB, m is 2. In additional embodiments of formula ZB, $R_4$ and $R_5$ are both N. In an embodiment of formula ZB, $R_3$ is allyl. In specific embodiments of formula ZB, B is aryl. In specific embodiments of formula ZB, B is $R_9$—O—CO—. In another embodiment of formula ZB, $R_2X$ is OH. In another embodiment of formula ZB, $R_2X$ is $NH_2$. In specific embodiments of formula ZB, aryl groups are phenyl groups substituted with one or more R groups as defined above. In specific embodiments of formula ZB, alkyl groups are C1-C6 alkyl groups or C1-C3 alkyl groups. In specific embodiments of formula ZB, alkenyl groups are C2-C6 alkenyl groups or C2-C4 alkenyl groups. In specific embodiments of formula ZB, alkenyl groups are allyl groups. In specific embodiments of formula ZB, $R_9$ is a t-butyl group. In specific embodiments of formula ZB, $R_6$ is hydrogen or methyl. In specific embodiments of formula ZB, n is 0 and B is $R_9$—O—CO—. In specific embodiments, n is 1 or 2 and B is aryl. In a specific embodiment of formula ZB, R is hydrogen. In a specific embodiment of formula ZB, at least one R or $R_3$ is a substituent other than hydrogen. In a specific embodiment of formula ZB, at least one R is a substituent other than hydrogen. In a specific embodiment of formula ZB, $R_2X$ is OH and $R_3$ is allyl.

In an embodiment, the invention provides compounds of formula ZC:

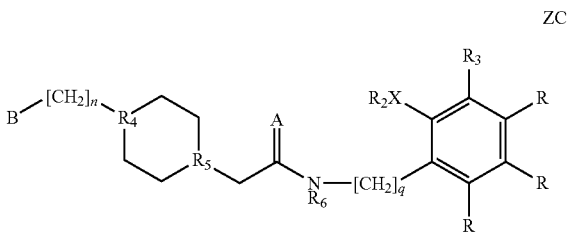

ZC and salts thereof, where q is 1 or 2 and other variables are as defined for formula Z.

In a specific embodiment of formula ZC, q is 2. In a specific embodiment of formula ZC, $R_3$ is allyl. In another embodiment of formula ZC, $R_2X$ is OH. In another embodiment of formula ZC, $R_2X$ is $NH_2$. In specific embodiments of formula ZC, aryl groups are phenyl groups substituted with one or more R groups as defined above. In specific embodiments of formula ZC, alkyl groups are C1-C6 alkyl groups or C1-C3 alkyl groups. In specific embodiments of formula ZC, alkenyl groups are C2-C6 alkenyl groups or C2-C4 alkenyl groups. In specific embodiments of formula ZC, alkenyl groups are allyl groups. In specific embodiments of formula ZC, B is a $R_9$—O—CO—. In specific embodiments of formula ZC, B is a phenyl substituted with one or more R substituents. In specific embodiments of formula ZC, $R_9$ is a t-butyl group. In specific embodiments, $R_6$ is hydrogen or methyl. In specific embodiments of formula ZC, n is 0 and B is $R_9$—O—CO—. In specific embodiments of formula ZC, n is 1 or 2 and B is aryl. In a specific embodiment of formula ZC, A is O. In a specific embodiment of formula ZC, R is hydrogen. In a specific embodiment of formula ZC, at least one R or $R_3$ is a substituent other than hydrogen. In a specific embodiment of formula ZC, at least one R is a substituent other than hydrogen. In a specific embodiment of formula ZC, $R_2X$ is OH and $R_3$ is allyl.

In an embodiment, the invention provides compounds of formula ZD:

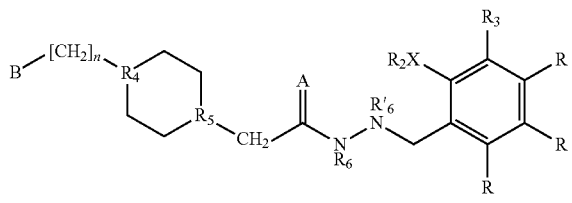

ZD and salts thereof, where each of $R_6$ and $R'_6$ is independently selected from hydrogen or alkyl and other variables are as defined in formula Z.

In specific embodiments of formula ZD, $R_6$ is hydrogen or methyl and $R'_6$ is hydrogen. In specific embodiments of formula ZD, $R'_6$ is hydrogen. In specific embodiments of formula ZD, n is 1 and B is aryl. In specific embodiments of formula ZD, n is 1 and B is phenyl substituted with one or more R groups as defined above. In specific embodiments of formula ZD, A is O.

In an embodiment, the invention provides compounds of formula ZY:

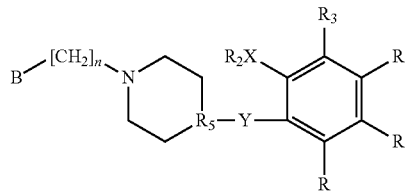

ZY and salts thereof, where Y is selected from any one of:

Y1=—$CH_2$—CO—$NR_6$—N=CH—

Y2=—$CH_2$—CO—$NR_6$—$NR'_6$—$CH_2$

Y3=—$CH_2$—$CH_2$—$NR_6$—N=CH—

Y4=—$CH_2$—$CH_2$—$NR_6$—$NR'_6$—$CH_2$

Y5=—$CH_2$—CO—NH—$CH_2$—$CH_2$—, or

Y6=—$CH_2$—CO—NH—$CH_2$—, $R_5$ is CH or N and other variables are as defined in above formulas.

In specific embodiments of formula ZX, n is 1 and B is aryl or heteroaryl. In specific embodiments of formula ZX, n is 1 and B is phenyl, R-substituted phenyl or pyridinyl. In specific embodiments of formula ZX, Y is Y2, Y3, or Y4. In specific embodiments of formula ZX, Y is Y5 or Y6. in specific embodiments, $R_5$ is CH or N. IN specific embodiments, $R_5$ is N. In specific embodiments, Y is Y1, n is 0 and B is $R_9$—O—OCO—. In specific embodiments, n is 0 and B is B is $R_9$—O—CO—. In specific embodiments $R^2X$ is OH. In specific embodiments, $R_2 X$ is —$NH_2$. In specific embodiments $R^2X$ is OH and $R_3$ is allyl. In specific embodiments, $R_2 X$ is —$NH_2$ and $R_3$ is allyl. In specific embodiments, at least one of R is a non-hydrogen substituent. In specific embodiments, $R_6$ is hydrogen or methyl. In specific embodiments, $R'_6$ is hydrogen.

In an embodiment, the invention provides compounds of formula GX:

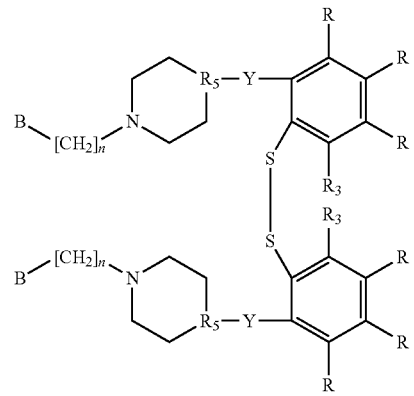

GX and salts thereof, where variables are as defined above. In specific embodiments Y is Y1. In other specific embodiments, Y is Y1 and B is aryl. In other specific embodiments $R_5$ is N. In other specific embodiments, R and $R_3$ are all hydrogens. In other specific embodiments, B is aryl. In other specific embodiments, n is 1 or 2. In other specific embodiments, B is phenyl and $R_4$ represents substitution with hydrogens on the phenyl ring. IN other embodiments, Y is Y1, A is O and $R_6$ is hydrogen. In other embodiments, Y is Y1, n is 1, B is optionally substituted phenyl. In other embodiments, B is $R_9$—OCO—. In other embodiments $R_9$ is C1-C6 alkyl and more specifically is t-butyl. In other specific embodiments, Y is Y1, $R_5$ is N, n is 0 and B is optionally substituted phenyl. In other specific embodiments, Y is Y1, $R_5$ is N, n is 0 and B is $R_9$—OCO—. In specific embodiments Y is Y2 or Y4. In other specific embodiments, Y is Y1 or Y3. In other specific embodiments, Y is Y5 or Y6.

In an embodiment, a compound is provided wherein B is a phenyl with at least one substituent other than hydrogen. In an embodiment, a compound is provided wherein the aromatic ring shown on the right side of compound ZY (or its analogous equivalent in other compounds described herein) has at least one substituent other than hydrogen. In an embodiment, a compound is provided wherein both rings have at least one substituent other than hydrogen.

In an embodiment, the method further comprises the step of assessing a procaspase-3 or caspase-3 parameter in a cancer cell; wherein said parameter is one or more of a semi-quantitative or quantitative amount, a functional amount, and an activity level of said procaspase-3 or caspase-3.

In an embodiment, the invention provides a method of direct in vitro screening for a compound capable of modifying a procaspase-3 molecule, comprising: (a) providing a test compound; (b) providing a purified procaspase-3; (c) exposing the test compound to the purified procaspase-3; (d) measuring a procaspase-3 activity following exposure to the test compound; (e) identifying a modifying compound by comparing a test activity upon the exposure to the test compound with an unmodified activity in the absence of exposure to the test compound; thereby screening for a compound capable of modifying a procaspase-3 molecule. In an embodiment, the method further comprises comparing said modified activity or said unmodified activity with a reference activity; wherein said reference activity is due to exposure of procaspase-3 to a compound selected from the group consisting of structural formula Z, ZA, ZB, ZC, ZD, ZZ, PAC-1 or Compound 5.

In an embodiment, the invention provides a method of screening for a compound capable of activating procaspase-3 comprising: a) providing procaspase-3; providing a test compound, preferably a small molecule; b) reacting the procaspase-3 with the test compound, thereby putatively generating caspase-3; and c) measuring caspase-3 activity. In a particular embodiment, the measuring caspase-3 activity employs a substrate, Ac-DEVD-pNA. In a particular embodiment, the measuring uses a wavelength readout parameter of about 410 nm. In a particular embodiment, the screening is carried out in parallel using multiple test compounds.

In an embodiment, the invention provides a method of screening which uses the detection of a subunit of pro-caspase-3 as an indicator that the full length (inactive) pro-caspase-3 is processed to caspase-3. In a particular embodiment, the subunit has a molecular weight of about 19 kD as measured by a protein gel migration technique, for example in a Western blot.

In an embodiment, the invention provides a method of in cellular screening for a compound capable of modifying a procaspase-3 molecule, comprising: (a) providing a test compound; (b) providing a cell, wherein the cell putatively expresses procaspase-3; (c) exposing the cell to the test compound; (d) measuring a cell parameter following exposure to the test compound; wherein said parameter comprises one or more of cell viability, apoptotic indicator, and other parameters; (e) identifying a modifying compound by comparing a tested cell parameter upon the exposure to the test compound with an unmodified cell parameter in the absence of exposure to the test compound; thereby screening for a compound capable of modifying a procaspase-3 molecule. In an embodiment, the method further comprises comparing said modified activity or said unmodified activity with a reference activity; wherein said reference activity is due to exposure to a compound selected from the group consisting of formula Z, ZA, ZB, ZC, ZD, or ZZ or subsets of compounds of such formula, PAC-1, and Compound 5.

In an embodiment, the invention provides a method of identifying or diagnosing a potential susceptibility to treatment for a cancer cell with a procaspase activator compound, comprising (a) assessing a procaspase parameter in said cancer cell; and (b) determining if said parameter allows an increased susceptibility to activation of a procaspase. In an embodiment, said procaspase parameter is a procaspase-3 level and said procaspase is procaspase-3. In an embodiment, said procaspase parameter is a procaspase-7 level and said procaspase is procaspase-7. A level can be a semi-quantitative or quantitative amount, or functional amount (e.g. an activity-based amount, e.g. a standardized unit or international unit).

In an embodiment, the invention provides a method of treating a cancer cell, comprising (a) identifying a potential susceptibility to treatment of a cancer cell with a procaspase activator compound; and (b) exposing said cancer cell to an effective amount of the procaspase activator compound. In an embodiment, the procaspase activator compound is selected from the group consisting of formula ZZ or subsets of compounds of such formula, PAC-1, and Structure 5. In an embodiment, the method of claim 16 wherein said procaspase activator compound is capable of activating procaspase-3, procaspase-7, or both procaspase-3 and procaspase-7.

In an embodiment, the invention provides a method of synthesizing PAC-1, comprising the steps of Scheme 1. In an embodiment, the invention provides a method of synthesizing Compound 5, comprising the steps of Scheme 1 with appropriate modification. In an embodiment, the invention provides a method of synthesizing compounds of the formula Z as disclosed herein and as would be understood in the art.

In an embodiment, the invention provides compounds of the formula Z1, ZA1, ZC1 or ZZ1:

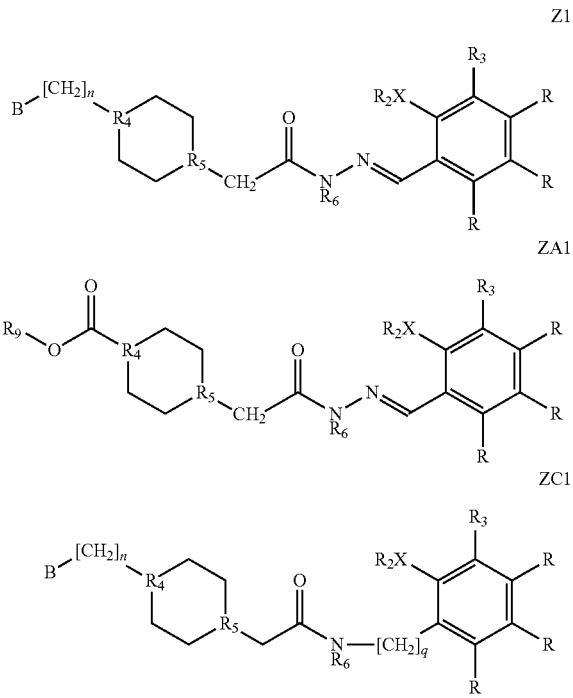

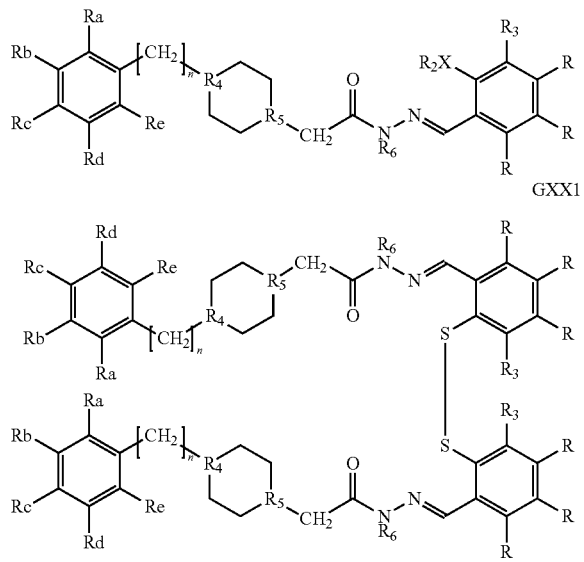

and salts thereof where variables are as defined above.

In specific embodiments of formulas Z1, ZA1, ZC1 and ZZ1, $R_2X$ is OH. In specific embodiments of formulas Z1 and ZA1, both $R_4$ and $R_5$ are N. In specific embodiments of formulas Z1, ZA1, ZC1 and ZZ1, $R_6$ is hydrogen. In specific embodiments of formulas Z1, ZA1, ZC1 and ZZ1, $R_3$ is allyl. In a specific embodiment of formulas Z1, ZA1, ZC1 and ZZ1, at least one R or $R_3$ is a substituent other than hydrogen. In a specific embodiment of formulas Z1, ZA1, ZC1 and ZZ1, at least one R is a substituent other than hydrogen. In a specific embodiment of formulas Z1, ZA1, ZC1 and ZZ1, $R_2X$ is OH and $R_3$ is allyl. In specific embodiments of formulas Z1, ZA1, ZC1 and ZZ1, one or two of Ra, Rb, Rc, Rd or Re are halogens, C1-C3 alkyl or C1-C3 alkoxy groups and the remaining groups are hydrogens. In specific embodiments of formulas Z1, ZA1, ZC1 and ZZ1, all of Ra, Rb, Rc, Rd, and Re are hydrogens.

In specific embodiments of GXX1, $R_3$ and R are all hydrogens. In specific embodiments of GXX1, $R_a$, Rb, Rc, Rd, and Re are all hydrogens. In specific embodiments of GXX1, n is 1. In specific embodiments of GXX1, $R_6$ is hydrogen.

In specific embodiments, the invention provides compounds of formula DX1, DX2, DX3, DX4, DX5, DX6, DX7, DX8, DX9, DX10, DX11, DX12, DX13, DX14, DX15, DX16, or DX17.

In specific embodiments, the invention provides compounds of formulas illustrated in FIG. 12.

In specific embodiments, the invention provides compounds of formulas FX1, FX2, FX3, FX4, FX5, FX6, FX7, FX8, and FX9.

In specific embodiments, the invention provides a compound of formula GX1.

In an embodiment, the invention provides a therapeutic composition comprising one or more compounds of any of the formulas herein and for each compound a pharmaceutically acceptable salt or ester thereof; wherein the compounds are present in the composition in an amount or in a combined amount effective for obtaining the desired therapeutic benefit. The therapeutic compositions of this invention optionally further comprise one or more pharmaceutically acceptable components, for example carriers and excipients as known in the art.

In an embodiment, the invention provides a method of screening a candidate cancer patient for possible treatment with a procaspase activator by identifying an elevated level of a procaspase in the candidate, comprising obtaining a cell or tissue test sample from the candidate, assessing the procaspase level in the test sample, and determining whether the procaspase level is elevated in the test sample relative to a reference level, thereby screening a candidate cancer patient for possible treatment with a procaspase activator. In an embodiment, the procaspase is selected from the group consisting of procaspase-2, -3, -6-, -7, -8, and -9. In a particular embodiment, the procaspase is procaspase-3.

In an embodiment, an elevated level of the test sample is at least about 2-fold greater than the reference level. In an embodiment, an elevated level of the test sample is at least about 4-fold greater than the reference level. In an embodiment, the reference level is from a second test sample from the same patient. In an embodiment, the reference level is from a normal cell or tissue sample. The reference level can be from a cell line, such as a cancer cell line or a normal cell line. In an embodiment, the reference level is an absolute threshold amount. See Svingen, P. A. et al., Clin. Cancer Res. 10:6807-6820 which describes various amounts of levels of procaspases including numbers of molecules per cell.

In an embodiment, the invention provides a method of inducing apoptosis in a cell, comprising administering to said cell a compound of the invention. In an embodiment, the cell is a cancer cell. In an embodiment, the compound has structural formula Z, ZA, ZB, ZC, ZD or ZZ.

In an embodiment, the invention provides a method of inducing death in a cancer cell, comprising administering to said cancer cell a compound capable of activating a procaspase molecule of said cancer cell. In an embodiment the procaspase is one or more of procasepas-3 and procaspase-7. In a preferred embodiment the procaspase is procaspase 3. In an embodiment, the compound has structural formula Z, ZA, ZB, ZC, ZD or ZZ.

In an embodiment, the invention provides a medicament comprising one or more compounds of formulas Z, ZA, ZB, ZC, ZD, or ZZ as well as a method for making a medicament comprising such compounds. More specifically, the medicament further comprising a pharmaceutically acceptable carrier suitable for a selected means of administration of the medicament. In a more specific method of making the medicament, one or more compounds of the recited formulas are combined with the selected pharmaceutically acceptable carrier.

In an embodiment, the invention provides compositions and methods where a compound of the composition or method is not a compound disclosed in: U.S. Provisional Application Ser. 60/684,807 filed May 26, 2005; U.S. Provisional Application Ser. 60/743,878 filed Mar. 28, 2006; U.S. patent application Ser. No. 11/420,425 filed May 25, 2006 (published as US 20070049602, Mar. 1, 2007); PCT International Application Serial PCT/US 06/020910 filed May 26, 2006 (published as WO2006/128173, 30 Nov. 2006). In an embodiment herein, said compound is not a compound of formula is of formula ZZX;

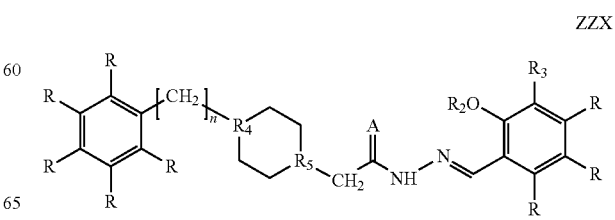

wherein n=1 or 2; R, independently of other R, is hydrogen, halogen, allyl, or short alkyl; R2=hydrogen, short alkyl, ester, or other moiety that is removable under physiological conditions; R3=hydrogen, halogen, alkyl, haloalkyl, allyl, alkenyl, alkenol, alkanol, or haloalkenyl; R4 and R5 are N; or R4=N and R5=C; or R4 and R5=C; and A=oxygen or sulfur.

BRIEF DESCRIPTION OF THE FIGURES

FIG. 3. PAC-1 induces apoptosis in HL-60 cells. A) Phosphatidylserine exposure (as measured by Annexin-V staining) after a 20 hour treatment with 100 μM PAC-1. B) Chromatin condensation as visualized by Hoescht staining after a 20 hour treatment with 100 μM PAC-1.

FIG. 5E illustrates results of progression of cancer in a lung cancer model for control, PAC-1, and gefitinib (Iressa™; AstraZeneca) treatment groups. Tumor cells were injected into mice by i.v. administration; Iressa and PAC-1 were given orally at 100 mg/kg.

FIG. 9 illustrates a nucleotide sequence for *Homo sapiens* caspase 3, apoptosis-related cysteine peptidase (CASP3), transcript variant alpha, mRNA (Accession No. NM_004346; 2689 bp mRNA linear; obtained from http://www.ncbi.nlm.nih.gov/entrez).

FIG. 10 illustrates a nucleotide sequence for *Homo sapiens* caspase 7, apoptosis-related cysteine peptidase (CASP7), transcript variant alpha, mRNA (Accession No. NM_001227; 2605 bp; mRNA linear; obtained from http://www.ncbi.nlm.nih.gov/entrez).

DETAILED DESCRIPTION OF THE INVENTION

Figure 1A:
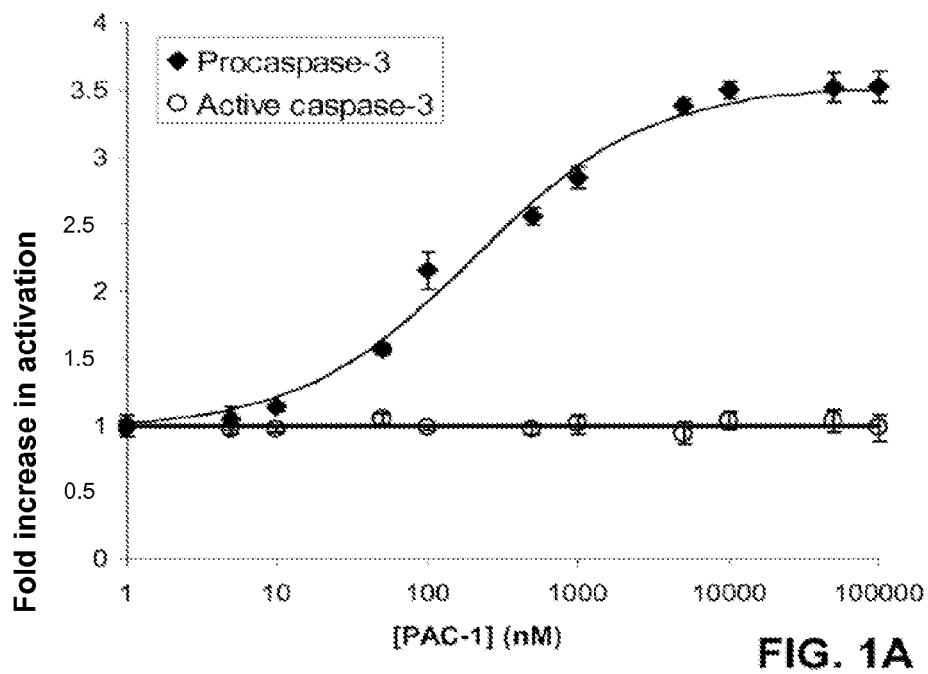
FIG. 1. A) In vitro activation of procaspase-3 and active caspase-3 by PAC-1. PAC-1 activates procaspase-3 with an $EC_{50}$=0.22 μM. Error bars represent standard deviations from the mean. B) Cleavage of procaspase-3 to active caspase-3 as induced by PAC-1. Procaspase-3 was recombinantly expressed in *E. coli* with an N-terminal His-6 tag and purified. Immunoblotting was performed with an anti-His-6 antibody. In the absence of PAC-1, no maturation of procaspase-3 is observed. In the presence of 100 μM PAC-1, cleavage to generate the p19 fragment is observed within 1 hour, and >50% cleavage is observed after 4 hours.

In general, the terms and phrases used herein have their art-recognized meaning, which can be found by reference to standard texts, journal references and contexts known to those skilled in the art.

The following abbreviations are applicable. IAP, inhibitor of apoptosis; PAC-1, procaspase activating compound 1; PARP, Poly(ADP-ribose) polymerase.

The following definitions are provided to clarify their specific use in the context of the invention.

When used herein, the term "chemotherapeutic agent" refers to any substance capable of reducing or preventing the growth, proliferation, or spread of a cancer cell, a population of cancer cells, tumor, or other malignant tissue. The term is intended also to encompass any antitumor or anticancer agent.

When used herein, the term "effective amount" is intended to encompass contexts such as a pharmaceutically effective amount or therapeutically effective amount. For example, in embodiments the amount is capable of achieving a beneficial state, beneficial outcome, functional activity in a screening assay, or improvement of a clinical condition.

When used herein, the term "cancer cell" is intended to encompass definitions as broadly understood in the art. In an embodiment, the term refers to an abnormally regulated cell that can contribute to a clinical condition of cancer in a human or animal. In an embodiment, the term can refer to a cultured cell line or a cell within or derived from a human or animal body. A cancer cell can be of a wide variety of differentiated cell, tissue, or organ types as is understood in the art.

The term "alkyl" refers to a monoradical branched or unbranched saturated hydrocarbon chain preferably having from 1 to 22 carbon atoms and to cycloalkyl groups having one or more rings having 3 to 22 carbon atoms. Short alkyl groups are those having 1 to 6 carbon atoms including methyl, ethyl, propyl, butyl, pentyl and hexyl groups, including all isomers thereof. Long alkyl groups are those having 8-22 carbon atoms and preferably those having 12-22 carbon atoms as well as those having 12-20 and those having 16-18 carbon atoms.

The term "cycloalkyl" refers to cyclic alkyl groups of from 3 to 22 carbon atoms having a single cyclic ring or multiple condensed rings. Cycloalkyl grouos include those having 3-8 member rings and those having 5 and 6 member rings. Cycloalkyl groups include, by way of example, single ring structures such as cyclopropyl, cyclobutyl, cyclopentyl, cyclohexyl, cyclooctyl, and the like, or multiple ring structures such as adamantanyl, and the like.

The term "alkenyl" refers to a monoradical of a branched or unbranched unsaturated hydrocarbon group preferably having from 2 to 22 carbon atoms and to cycloalkenyl groups having one or more rings having 3 to 22 carbon atoms wherein at least one ring contains a double bond. Alkenyl groups may contain one or more double bonds (C=C) which may be conjugated. Preferred alkenyl groups are those having 1 or 2 double bonds. Short alkenyl groups are those having 2 to 6 carbon atoms including ethylene (vinyl) propylene, butylene, pentylene and hexylene groups, including all isomers thereof. Long alkenyl groups are those having 8-22 carbon atoms and preferably those having 12-22 carbon atoms as well as those having 12-20 carbon atoms and those having 16-18 carbon atoms. The term "cycloalkenyl" refers to cyclic alkenyl groups of from 3 to 22 carbon atoms having a single cyclic ring or multiple condensed rings in which at least one ring contains a double bond (C=C). Cycloalkenyl groups include, by way of example, single ring structures such as cyclopropenyl, cyclobutenyl, cyclopentenyl, cyclooctenyl, cylcooctadienyl and cyclooctatrienyl. The term allyl refers to the alkenyl group —CH$_2$—CH=CH$_2$.

The term "alkynyl" refers to a monoradical of an unsaturated hydrocarbon preferably having from 2 to 22 carbon atoms and having one or more triple bonds (C C). Alkynyl groups include ethynyl, propargyl, and the like. Short alkynyl groups are those having 2 to 6 carbon atoms, including all isomers thereof. Long alkynyl groups are those having 8-22 carbon atoms and preferably those having 12-22 carbon atoms as well as those having 12-20 carbon atoms and those having 16-18 carbon atoms.

The term "aryl" refers to a group containing an unsaturated aromatic carbocyclic group of from 6 to 22 carbon atoms having a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Aryls include phenyl, naphthyl and the like. Aryl groups may contain portions that are alkyl, alkenyl or akynyl in addition to the unsaturated aromatic ring(s). The term "alkaryl" refers to the aryl groups containing alkyl portions, i.e., -alkylene-aryl and -substituted alkylene-aryl). Such alkaryl groups are exemplified by benzyl (—CH$_2$-phenyl), phenethyl and the like.

Alkyl, alkenyl, alkynyl and aryl groups are optionally substituted as described herein (the term(s) can include substituted variations) and may contain 1-8 non-hydrogen substituents dependent upon the number of carbon atoms in the group and the degree of unsaturation of the group. All such variable as described herein can be unsubstituted (in which any variables groups that can be hydrogen are hydrogen) or substituted with one or more non-hydrogen substituents selected from halogen, including fluorine, chlorine, bromine or iodine, C1-C3 haloalkyl, hydroxyl (OH), thiol (HS—), C1-C6 alkyl, C1-C3 alkyl, C1-C6 alkoxy, C1-C3 alkoxy, phenyl, benzyl, alkenyl, C2-C4 alkenyl, alkynyl, C2-C4 alkynyl, —NH$_2$, —NR'H, —NR'R", R'CO—, R'R"NCO—, R'CO—NH—, or R'CO—NR'—, where R' and R" are C1-C6 alkyl, C1-C3 alkyl or phenyl.

The term "amino" refers to the group —NH$_2$ or to the group —NR'R" where each R' and R" is independently selected from the group consisting of hydrogen, alkyl or aryl groups.

Haloalkyl" refers to alkyl as defined herein substituted by one or more halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" refers to an aromatic group of from 2 to 22-carbon atoms having 1 to 4 heteroatoms selected from oxygen, nitrogen and sulfur within at least one ring (if there is more than one ring). Heteroaryl groups may be optionally substituted. Heteroaryl grouos include among others those having 5 and 6-member rings and those having one or two nitrogens in the ring, those having one or two oxygens in the ring as well as those having one or two sulfurs in the ring.

The term "heterocycle" or "heterocyclic" refers to a monoradical saturated or unsaturated group having a single ring or multiple condensed rings, from 2-22 carbon atoms and from 1 to 6 hetero atoms, preferably 1 to 4 heteroatoms, selected from nitrogen, sulfur, phosphorus, and/or oxygen within at least one ring. Heterocyclic groups may be substituted. Rings preferably have 3-10 members and more specifically have 5 or 6 members.

The term "ester" refers to chemical entities as understood in the art and in particular can include groups of the form (RCO—).

As to any of the above groups which contain one or more substituents, it is understood, that such groups do not contain any substitution or substitution patterns which are sterically impractical and/or synthetically non-feasible. The compounds of this invention include all novel stereochemical isomers arising from the substitution of disclosed compounds.

In an embodiment, the invention provides compounds of the formula Z excluding PAC-1, wherein the structure of PAC-1 is:

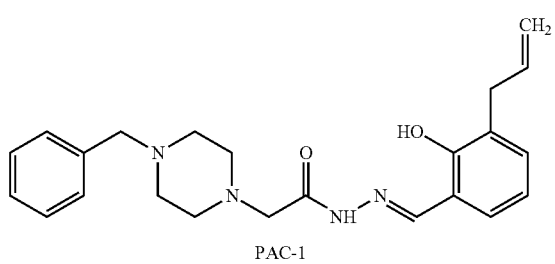 [SMILES: C=CCc1cccc(/C=N/NC(=O)CN2CCN(Cc3ccccc3)CC2)c1O]

PAC-1

In an embodiment, the invention provides a compound of compound 5, which is:

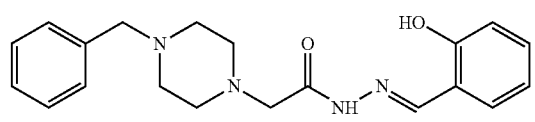 [SMILES: O=C(CN1CCN(Cc2ccccc2)CC1)N/N=C/c1ccccc1O]

In an embodiment, the invention provides a compound of formula Z other than compound 5.

In an embodiment, the invention provides a compound having the formula Z2:

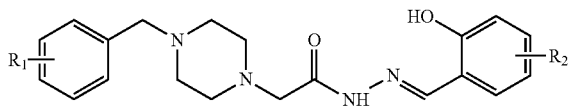

wherein $R_1$ and $R_2$ independently represent substitution on the indicated rings with one or more hydrogen, halogen, alkyl, allyl, haloalkyl, alkenyl, alkenol, alkanol, or haloalkenyl. In an embodiment, $R_1$ and $R_2$ independently represent substitution on the indicated rings with one or more hydrogen, halogen, allyl, or C1-C3 alkyl.

In an embodiment, the invention provides a compound selected from the group consisting of a PAC-1 derivative combinatorial library comprising a hydrazide compound combined with an aldehyde compound. In an embodiment, the hydrazide compound is selected from the group consisting of hydrazides generated from AX compounds described herein.

In an embodiment, the aldehyde compound is selected from the group consisting of BX compounds described herein. In an embodiment, the hydrazide compound is selected from the group consisting of AX compounds described herein and the aldehyde compound is selected from the group consisting of BX compounds described herein.

In an embodiment, the invention provides a method of synthesizing a PAC-1 derivative compound comprising providing a hydrazide compound, providing an aldehyde compound, and reacting the hydrazide compound with the aldehyde compound, thereby synthesizing a PAC-1 derivative compound.

In an embodiment, the hydrazide compound has the formula ZZ3:

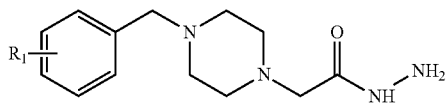

where $R_1$ represents substitution on the indicated ring of one or more R groups as defined in formula Z.

In an embodiment, the aldehyde compound has the formula ZZ4:

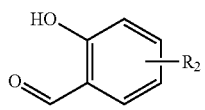

where $R_2$ represents substitution on the indicated ring of one or more $R_3$ or R groups as defined in formula Z.

In an embodiment, the hydrazide compound has the formula ZZ3 and the aldehyde compound has the formula ZZ4.

In an embodiment, the invention provides a compound selected from the group consisting of: L01R06, L02R03, L02R06, L08R06, L09R03, L09R06, and L09R08.

In an embodiment, a composition of the invention is a chemotherapeutic agent.

In an embodiment, the invention provides compounds and methods involving effective concentrations preferably from about 10 nM to about 100 μM of the disclosed structural formulas. In another preferred embodiment, the effective concentrations are from about 200 nM to about 5 μM. In an embodiment, the effective concentration is considered to be a value such as a 50% activity concentration in a direct procaspase activation assay, in a cell apoptosis induction assay, or in an animal clinical therapeutic assessment. In a preferred embodiment, such value is less than about 200 μM. In a preferred embodiment, the value is less than about 10 μM.

Compounds of the invention and compounds useful in the methods of this invention include those of the disclosed formulas and salts and esters of those compounds, including preferably pharmaceutically-acceptable salts and esters.

In an embodiment, the invention provides prodrug forms of compositions. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. A biomolecule such as a precursor protein or precursor nucleic acid can be a prodrug. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

In an embodiment, a composition of the invention is in a form that is isolated or purified.

It is recognized that regardless of the ultimate correctness of any mechanistic explanation or hypothesis believed or disclosed herein, an embodiment of the invention can nonetheless be operative and useful.

When a group of substituents is disclosed herein, it is understood that all individual members of that group and all subgroups, including any isomers and enantiomers of the group members, are disclosed separately. When a Markush group or other grouping is used herein, all individual members of the group and all combinations and subcombinations possible of the group are intended to be individually included in the disclosure. It is intended that any one or more members of any Makush group or listing provided in the specification can be excluded from the invention if desired. When a compound is described herein such that a particular isomer or enantiomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Specific names of compounds are intended to be exemplary, as it is known that one of ordinary skill in the art can name the same compounds differently.

Molecules disclosed herein may contain one or more ionizable groups [groups from which a proton can be removed (e.g., —OH, —COOH, etc.) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. For example, in general any anions can be employed in the formation of salts of compounds herein; e.g. halide, sulfate, carboxylate, acetate, phosphate, nitrate, trifluoroacetate, glycolate, pyruvate, oxalate, malate, succinate, fumarate, tartarate, citrate, benzoate, methanesulfonate, ethanesulfonate, p-toluenesulfonate, salicylate and others.

Compounds of the present invention, and salts or esters thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, the compounds may have trans and cis isomers and may contain one or more chiral centers, therefore existing in enantiomeric and diastereomeric forms. The invention can encompass all such isomers, individual enantiomers, as well as mixtures of cis and trans isomers, mixtures of diastereomers; non-racemic and racemic mixtures of enantiomers (optical isomers); and the foregoing mixtures enriched for one or more forms; except as stated otherwise herein. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

Every formulation or combination of components described or exemplified herein can be used to practice the invention, unless otherwise stated.

Whenever a range is described in the present application, for example, a temperature range, a time range, or a composition or concentration range, all intermediate ranges and subranges, as well as all individual values included in the ranges given are intended to be included in the disclosure.

Information in any references disclosed herein can in some cases indicate the state of the art, for example for patent documents as of their effective filing dates; it is intended that such information can be employed herein, if needed, to exclude specific embodiments that are actually found to be in the prior art. For example, when a compound is disclosed and/or claimed, it should be understood that compounds qualifying as prior art with regard to the present invention, including compounds for which an enabling disclosure is provided in the references, are not intended to be included in the composition of matter claims herein.

Some references provided herein are incorporated by reference to provide details concerning sources of starting materials, additional starting materials, additional reagents, additional methods of synthesis, additional methods of analysis, and additional uses of the invention. One of ordinary skill in the art will appreciate that starting materials, reagents, solid substrates, synthetic methods, purification methods, and analytical methods other than those specifically exemplified can be employed in the practice of the invention based on knowledge in the art and without resort to undue experimentation.

The invention may be further understood by the following non-limiting examples.

EXAMPLE 1

Procaspase Activating Compounds

Mutation or aberrant expression of proteins in the apoptotic cascade is a frequent hallmark of cancer. These changes can prevent proapoptotic signals from being transmitted to the executioner caspases, thus preventing apoptotic cell death and allowing cellular proliferation. Caspase-3 and caspase-7 are key executioner caspases, existing as inactive zymogens that are activated by upstream signals. Importantly, expression levels of procaspase-3 are significantly higher in certain cancerous cells relative to non-cancerous controls. Here we report the identification of small molecules that directly activate procaspase-3 to active caspase-3. A particular compound, PAC-1, effects activation in vitro with an $EC_{50}$ on the order of 220 nanomolar and induces apoptosis in a multitude of cancerous cell lines.

In contrast to many known anti-cancer drugs, cells treated with PAC-1 show an immediate activation of procaspase-3, and the toxicity of PAC-1 is shown to be directly proportional to the amount of procaspase-3 contained in a cell. Thus PAC-1 directly activates procaspase-3 to caspase-3 in vivo, allowing this compound to induce apoptosis even in cells that have defective apoptotic machinery. PAC-1 is the first small molecule known to directly activate procaspase-3; the direct activation of executioner caspases is a novel anti-cancer strategy that may prove beneficial in a variety of cancers, including the many cancers in which procaspase-3 is upregulated.

A collection of about 20,000 structurally diverse small molecules was screened for the ability to activate procaspase-3 in vitro. Procaspase-3 was expressed and purified in *E. coli* (Roy et al., 2001). Procaspase-3 (at a concentration of 50 ng/mL) was added to the wells of a 384-well plate, and the compounds were added to a final concentration of approximately 40 µM. Each plate was then incubated for two hours at 37° C., after which the caspase-3 peptidic substrate Ac-Asp-Glu-Val-Asp-p-nitroanilide (Ac-DEVD-pNa) was added to a concentration of 200 µM. The formation of the p-nitroaniline chromophore was followed at 405 nm over the course of two hours.

Of the compounds evaluated, four induced a significant increase over background in the hydrolysis of the peptidic caspase-3 substrate. Of those four, one showed a strong dose-dependent effect on in vitro procaspase-3 activation. As shown in FIG. 1A, this first procaspase activating compound (PAC-1) gives half-maximal activation of procaspase-3 at a concentration of 0.22 µM. This compound is not simply increasing the activity of caspase-3 itself, as it has no effect on the catalytic activity of the fully processed caspase-3 enzyme (FIG. 1A).

Procaspase-3 has an N-terminal pro domain (residues 1-28), followed by a large subunit (17 kDa) and a small subunit (12 kDa) that are separated by an intersubunit linker (Pop et al., 2003). In vivo, two procaspase-3 monomers assemble to form a catalytically inactive homodimer that can be activated by cleavage at D175 in the intersubunit linker. The precise role of the pro domain is unclear, and it has been shown that cleavage in the intersubunit region alone is sufficient for full catalytic activity (Stennicke, H. R. et al., 1998). Although procaspase-3 is catalytically competent, it is highly resistant to autoactivation due to the presence of the 12 amino acid safety catch; however, when the safety catch is mutated significant autoactivation of procaspase-3 is observed (Roy et al., 2001). Compounds that interact with this important regulatory region or at other positions can allow the autoactivation of procaspase-3.

To directly assess the ability of PAC-1 to catalyze the autoactivation of procaspase-3, the procaspase-3 protein was incubated with 100 μM of PAC-1 for time points ranging from one to five hours. As shown by the Western blot in FIG. 1B, PAC-1 induces the cleavage of procaspase-3 in a time-dependent fashion, with >50% processing observed after 4 hours. In contrast, procaspase-3 incubated in buffer shows virtually no autoactivation over that same time span. In an attempt to pinpoint the region of procaspase-3 with which PAC-1 is interacting, alanine substitutions were made in the key aspartic acid triad in the safety catch region, residues Asp179, Asp180 and Asp181. Mutations at these positions all dramatically decreased the ability of PAC-1 to activate procaspase-3, with certain mutations more detrimental to activation of procaspase-3 by PAC-1 (FIG. 2A).

Like caspase-3, caspase-7 also exists as an inactive zymogen that is activated by proteolysis. Caspase-3 and caspase-7 are both executioner caspases and have considerable sequence and structural homology (Denault, J.-B. et al., 2003). Procaspase-7 may also have a similar safety catch region, although it has only two aspartic acids in the key triad (Asp-Thr-Asp), instead of three. As indicated by the data in FIG. 2B, PAC-1 can also activate procaspase-7, although in a less efficient manner than its activation of procaspase-3 ($EC_{50}$ of 4.5 μM versus 0.22 μM for procaspase-3 activation). The potency of procaspase-7 activation by PAC-1 is similar to its effect on the Asp-Ala-Asp mutant of procaspase-3 ($EC_{50}$=2.77 μM). The effect of PAC-1 is abolished at low pH values where procaspase-3 undergoes rapid autoactivation (FIG. 2C).

The ability for a small molecule that activates procaspase-3 to induce apoptosis in human cell lines was tested, and PAC-1 was found to induce apoptosis in a variety of cancer cell lines. In HL-60 cells addition of PAC-1 leads to considerable phosphatidylserine exposure on the cell membrane accompanied by significant chromatin condensation (FIGS. 3A and B). In addition, the compound induces cleavage of PARP-1 (as assessed by an in vivo PARP activity assay; Putt K S et al., 2005) and causes mitochondrial membrane depolarization (see below). Significant cellular blebbing was also observed by microscopy. Furthermore, the toxicity of PAC-1 could be abolished in the presence of the caspase inhibitor z-VAD-fmk (data not shown; see Slee et al., 1996).

Figure 4A:
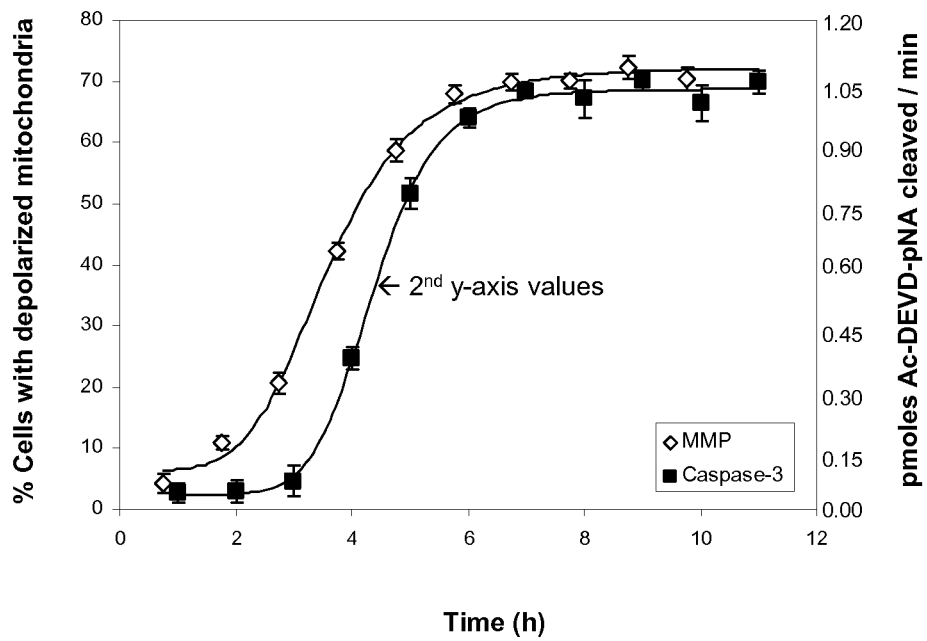
FIG. 4. A) Mitochondrial membrane depolarization (MMP) and caspase-3 like activity in HL-60 cells treated with 10 μM etoposide. B) Mitochondrial membrane depolarization (MMP) and caspase-3 like activity in HL-60 cells treated with 100 μM PAC-1. C) PAC-1 treatment (100 μM) induces a rapid decrease in cellular PARP activity in HL-60 cells, consistent with an immediate activation of cellular caspase-3/-7. In contrast, etoposide (10 μM) treated cells show a decrease in PARP activity at much later time points. D) PAC-1 induces cell death in a procaspase-3 dependent manner. For a number of diverse cancer cell lines, the procaspase-3 levels were determined (by flow cytometry) and the $IC_{50}$ of PAC-1 was measured (R2=0.9822). PAC-1 is quite potent ($IC_{50}$=0.35 μM) in the NCI-H226 lung cancer cell line known to have high levels of procaspase-3, but markedly less potent in normal white blood cells derived from the bone marrow of a healthy human donor. E) A graph showing the correlation between relative procaspase-3 concentration and $IC_{50}$ (μM).
Figure 4B:
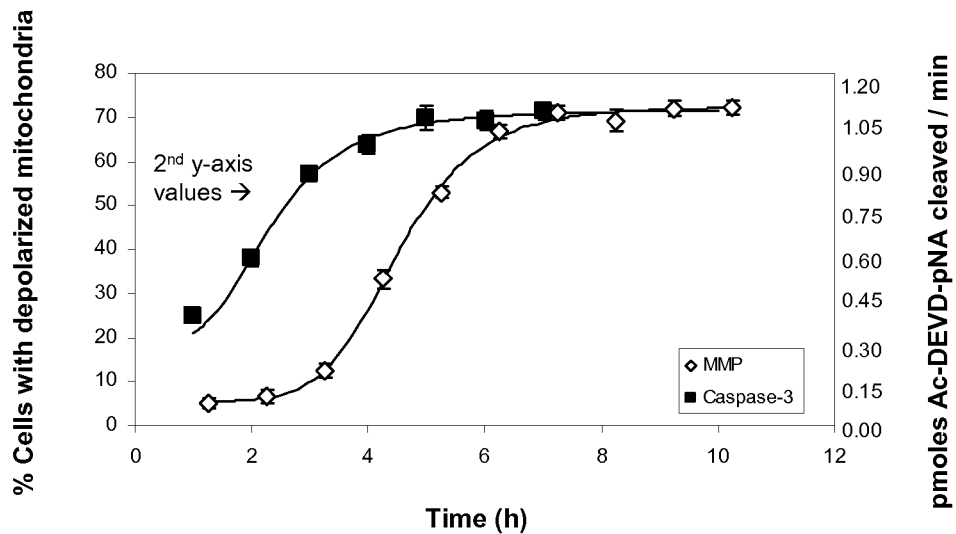
Figure 4C:
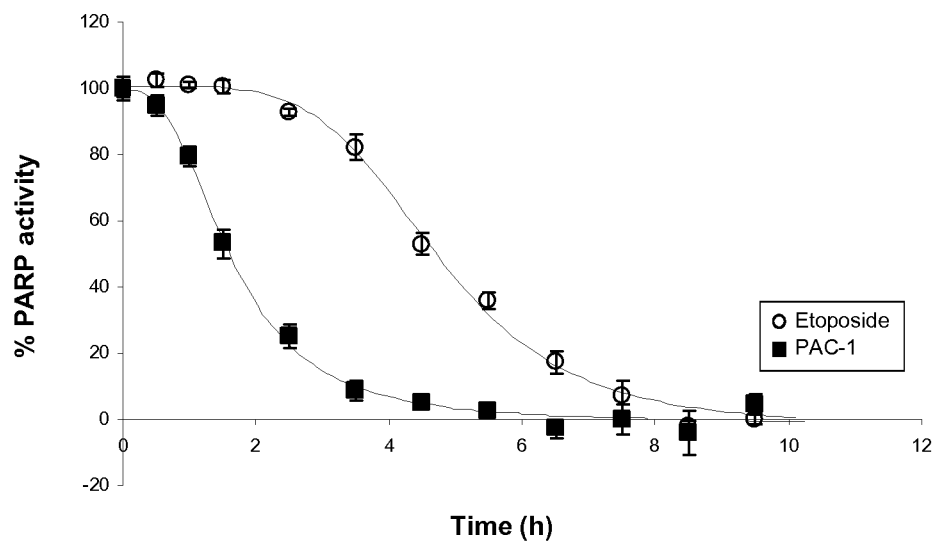

If PAC-1 is indeed inducing apoptosis via direct activation of procaspase-3, the time course of apoptotic events should be altered relative to that observed with standard proapoptotic agents. Etoposide is well known to induce apoptosis through the intrinsic pathway; thus, mitochondrial membrane depolarization is followed by procaspase-3 activation in etoposide-treated cells. Indeed, in HL-60 cells treated with 10 μM etoposide, mitochondrial membrane depolarization is observed, followed by detection of caspase-3-like activity (FIG. 4A). In contrast, treatment of cells with PAC-1 gives a markedly different result. With PAC-1, the first observed biochemical hallmark of apoptosis is caspase-3-like enzymatic activity. This activity is noted within minutes of compound addition, and 50% activation takes place in just over 2 hours and well before any significant mitochondrial membrane depolarization (FIG. 4B). In addition, PARP activity is rapidly reduced in cells treated with PAC-1, whereas this reduction is observed at later time points in etoposide treated cells (FIG. 4C). Control experiments show that PAC-1 does not directly inhibit enzymatic activity of PARP-1. In the typical sequence of apoptotic events, the mitochondrial membrane depolarizes, caspases are activated, and caspase substrates (such as PARP-1) are cleaved. The observation that cells treated with PAC-1 show a rapid activation of caspase-3/-7 (before mitochondrial membrane depolarization) and a rapid cleavage of a caspase substrate is indicative of this compound exerting its cellular toxicity through the direct activation of procaspase-3.

Figure 4D:
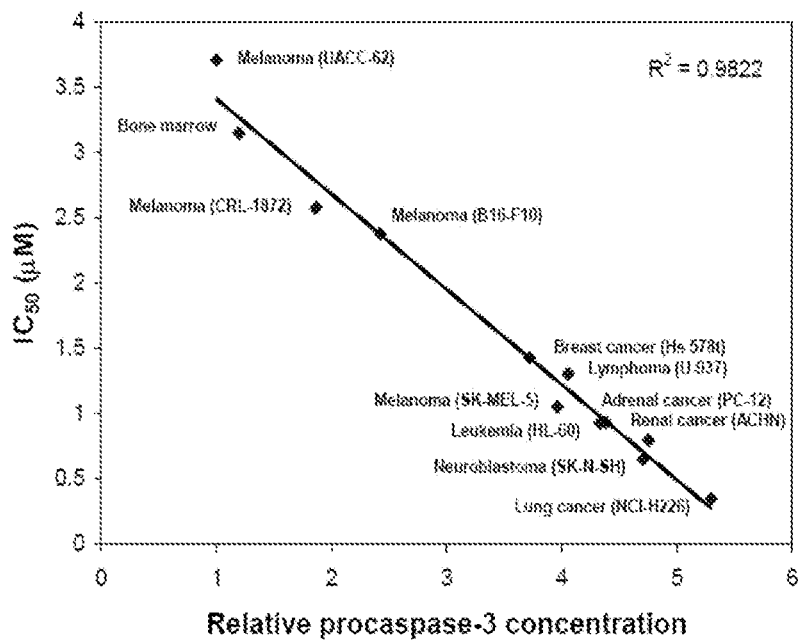

To further define the potency of PAC-1, the ability of this compound to induce cell death in cancer cell lines with varying levels of procaspase-3 was assessed. A determination was made of the amount of procaspase-3 present in multiple cancer cell lines (leukemia, lymphoma, melanoma, neuroblastoma, breast cancer, lung cancer and renal cancer) and in the white blood cells isolated from the bone marrow of a healthy donor. The $IC_{50}$ values for cell death induction were obtained for PAC-1 in these cell lines. The combined data shows a strong correlation between cellular concentration of procaspase-3 and sensitivity to PAC-1 (FIG. 4D). Notably, the white blood cells derived from the bone marrow of a healthy human donor are among those with the lowest amount of procaspase-3, and PAC-1 is comparatively less toxic to these cells. PAC-1 is most potent versus the lung cancer cell line NCI-H226, with an $IC_{50}$ of 0.35 μM. In accordance with data in the literature (Svingen et al., 2004), we found this cell line to have a concentration of procaspase-3 that is greater than five times that of the non-cancerous control.

In contrast to these experiments with PAC-1, etoposide showed no such correlation between potency in cell culture and cellular levels of procaspase-3. For instance, etoposide was ineffective ($IC_{50}$>50 μM) in inducing death in three of the melanoma cell lines (UACC-62, CRL-1872, and B16-F10), the breast cancer cell line (Hs 578t), and the lung cancer cell line (NCI-H226); these cell lines have procaspase-3 levels of 1.0, 2.4, 1.9, 3.7, and 5.3, respectively. Etoposide was effective ($IC_{50}$<1 μM) versus HL-60, U-937, SK-N-SH and PC-12, which have procaspase-3 levels of 4.3, 4.0, 4.7, and 4.4, respectively. Thus, overall there is no correlation between procaspase-3 levels and $IC_{50}$ for etoposide.

Cancerous cells typically have a reduced sensitivity to proapoptotic signals due to the mutation or aberrant expression of an assortment of proteins in the apoptotic cascade. As such, many types of cancer are notoriously resistant to not only the endogenous signals for apoptotic cell death, but also to chemotherapeutic agents that act through similar mechanisms. The paradoxical upregulation of procaspase-3 expression levels in certain cancers provides an opportunity to use this existing intracellular pool of protein to directly induce apoptosis, thus bypassing the often non-functional or compromised upstream portion of the cascade. Although procaspase-3 is notorious for its relative inability to undergo autoactivation, it is dependent upon a 12 amino acid safety catch to keep itself in the inactive state. PAC-1 induces the autoactivation of procaspase-3 in vitro, and this activation is greatly diminished by mutation of the key tri-aspartate region of the safety catch. This data is consistent with the notion that PAC-1 is directly interfering with the ability of the safety catch to maintain procaspase-3 dormancy.

In cell culture, PAC-1 treatment induces rapid caspase-3-like activity. It is likely that the caspase-3 mediated cleavage of anti-apoptotic proteins (Bcl-2, Bcl-XL, etc.) then induces depolarization of the mitochondrial membrane and amplifies apoptosis. Further, the potency of PAC-1 toward a variety of cancer cell lines is directly proportional to the concentration of procaspase-3 in the cell. It is worth noting that several of the cell lines that PAC-1 is effective against have faulty apoptotic pathways that make them resistant to apoptosis; for instance, Apaf-1 expression is dramatically decreased in SK-MEL-5 cells, and Bcl-2 is overexpressed in the NCI-H226 lung cancer cell line.

Data presented herein fully support the notion that procaspase-3 activating compounds can be exceedingly effective against common cancers. The effectiveness can be enhanced for situations in which procaspase-3 levels are aberrantly high.

Assessment of procaspase-3 levels in cancer biopsies can be simple and rapid; as such, the potential effectiveness of a compound such as PAC-1 can be assessed a priori with a high degree of accuracy. Procaspase-3 activators and methods herein thus provide personalized medicine strategies that can be preferential to therapies that rely on general cytotoxins in the realm of anti-cancer treatments.

Materials and Methods

Materials: Ni-NTA resin and anti-Penta His Alexa Fluor 647 antibody was purchased from Qiagen (Valencia, Calif.). Bradford dye was purchased from Bio-Rad (Hercules, Calif.). Pin transfer devices were purchased from V & P Scientific (San Diego, Calif.). The reagent z-vad-fmk was purchased from Calbiochem (San Diego, Calif.). Rosetta *E. coli* was purchased from Novagen (Madison, Wis.). Anti-caspase-3 antibody was purchased from Sigma (St. Louis, Mo.). Annexin V Alexa Fluor 488 conjugate, JC-9, and propidium iodide were purchased from Molecular Probes (Eugene, Oreg.). IPTG and MTS/PMS CellTiter 96 Cell Proliferation Assay reagent were purchased from Promega (Madison, Wis.). Fetal Bovine Serum was purchased from Biomeda (Foster City, Calif.). 96 and 384-well microtiter plates, microscope slides, microscope coverslips, horse serum and all other reagents were purchased from Fisher (Chicago, Ill.).

Methods: Cell Culture Conditions. U-937, HL-60, CRL-1872, ACHN, NCI-H226, SK-MEL-5 and UACC-62 cells were grown in RPMI 1640 media supplemented with 10% FBS. SK-N-SH, B16-F10 and Hs 578t cells were grown in Eagle's minimal essential medium with Earle's BSS, 1.5 g/L sodium bicarbonate and supplemented with 10% FBS. PC-12 cells were grown in RPMI 1640 media supplemented with 5% FBS and 10% horse serum. Human bone marrow was grown in IDMEM supplemented with 40% FBS. All cell lines were incubated at 37° C. in a 5% $CO_2$, 95% air atmosphere. U-937 and HL-60 cells were split every two to three days as needed. Human bone marrow was thawed from frozen stock and immediately diluted and used for experiments. All other cells were split when they reached approximately 80% confluency.

Protein Expression and Purification. 1 mL of an overnight culture of Rosetta *E. coli* containing the procaspase-3 or procaspase-7 expression plasmid was seeded into 1 L of LB media containing proper antibiotic. Cells were induced with 1 mM IPTG for 30 minutes. Cells were then spun down and re-suspended in NTA binding buffer (150 mM NaCl, 50 mM Tris, 10 mM Imidazole, pH 7.9). The cells were lysed by passing twice through a French press. The cell lysate was then spun at 14,000×g for 30 min. The supernatant was decanted and 1 mL of nickel-NTA resin was added. The cell lysate was incubated for 1 hour at 4° C. The resin was loaded on a column, washed with 10 mL NTA binding buffer followed by 10 mL NTA wash buffer (150 mM NaCl, 50 mM Tris, 20 mM Imidazole, pH 7.9). The proteins were eluted in 1 mL fractions with 10 mL of NTA elution buffer (150 mM NaCl, 50 mM Tris, 250 mM Imidazole, pH 7.9). Fractions containing protein were pooled and the amount of protein was determined using the Bradford assay.

Library Screen. Isolated procaspase-3 was diluted to 50 ng/mL in caspase assay buffer (50 mM HEPES, 100 mM NaCl, 10 mM DTT, 0.1 mM EDTA, 0.1% CHAPS and 10% glycerol, pH 7.4). 45 µL of the procaspase-3 solution was added to each well of a Nunc 384-well flat bottom microtiter plate. Approximately 20,000 compounds were screened. About 6,000 of the compounds were collected from various sources within the department of chemistry at the University of Illinois; their structures are available at: http://www.scs.uiuc.edu/~phgroup/comcollections.html. The other approximately 14,000 compounds were purchased from Chembridge Corporation (San Diego, Calif.). PAC-1 was a member of the compounds purchased from Chembridge Corporation.

The compounds, made up as 10 mM stock solutions in DMSO, were transferred into the wells using a 384-pin transfer apparatus that transfers 0.2 µL of compound. This yielded a final compound concentration of about 40 µM. Controls were performed in which only DMSO (containing no compound) was pin-transferred. The plates were then incubated for 2 hours at 37° C. 5 µL of a 2 mM solution of Ac-DEVD-pNA (N-acetyl-ASP-Glu-Val-Asp-p-nitroanilide) in caspase assay buffer was added to each well. The plate was then read every 2 minutes at 405 nm for 2 hours in a Spectra Max Plus 384 plate reader (Molecular Devices, Sunnyvale Calif.). The slope of the linear portion for each well was used to determine the activity of caspase-3.

Activation curves. The dose dependence of procaspase-3 activators was determined by adding various concentrations of compound to 90 µL of a 50 ng/mL procaspase-3, active caspase-3, procaspase-7 or active caspase-7 in caspase assay buffer in a 96-well plate. The plate was then incubated for 12 hours at 37° C. 10 µL of a 2 mM solution of Ac-DEVD-pNA in caspase assay buffer was then added to each well. The plate was read every 2 minutes at 405 nm for 2 hours in a Spectra Max Plus 384 well plate reader. The slope of the linear portion for each well was determined and the fold increase in activation from non-treated control wells was calculated.

PAC-1 activation gel. Procaspase-3 was expressed and isolated exactly as above. Procaspase-3 was diluted to about 50 µg/mL in caspase assay buffer. The procaspase-3 was then incubated in the presence or absence of 100 µM PAC-1 for varying times at 37° C. After this incubation, an equal volume of load buffer (150 mM NaCl, 50 mM Tris, 2% SDS, 20% glycerol, pH 8.0) was added to each procaspase-3 sample. All samples were then stored at −80° C. until the time-course was completed. All samples were then incubated at 95° C. for 5 minutes and run on a 12% SDS-PAGE gel. Proteins were then transferred to nitrocellulose paper overnight. Blots were washed in TTBS (150 mM NaCl, 50 mM Tris, 0.1% Tween-20, pH 7.4) and blocked with a 10% milk solution for 2 hours. Blots were then incubated in a 1:5000 dilution of anti-Penta His Alexa Fluor 647 antibody for 2 hours. The blot was then washed with TTBS and scanned on a Typhoon fluorescence scanner (Amersham Biosciences, SunnyVale Calif.).

Safety catch mutations. The DDD procaspase-3 safety catch (SEQ ID NO:1; SEQ ID NO:2; SEQ ID NO:9) was mutated to ADD (SEQ ID NO:3, SEQ ID NO:4, SEQ ID NO:10), DAD (SEQ ID NO:5, SEQ ID NO:6, SEQ ID NO:11) and DDA (SEQ ID NO:7, SEQ ID NO:8, SEQ ID NO:12) using the quickchange strategy with the following primers, gacagacagtggtgttgCGgatgacatggcgtgtcataaaatacc (SEQ ID NO:13), gacagacagtggtgttgatg Ctgacatggcgtgtcataaaatacc (SEQ ID NO:14) and gacagacagtggtgttgatgatgCcatggcgtgtcataaaatacc (SEQ ID NO:15) respectively. See also FIG. 9 and FIG. 10. Mutated bases are underlined and capitalized. All mutant plasmids were sequenced to ensure proper sequence throughout the gene. All mutant plasmids were expressed exactly as wild-type procaspase-3 as described above. The ability of PAC-1 to activate each procaspase-3 mutant was determined by adding various concentrations of PAC-1 to 90 µL of a 50 ng/mL wild-type procaspase-3 and mutant procaspase-3 in caspase assay buffer in a 96-well plate. The plate was then incubated for 12 hours at 37° C. 10 µL of a 2 mM solution of Ac-DEVD-pNA in caspase assay buffer was then added to each well. The plate was read every 2 minutes at 405 nm for 2 hours in a Spectra Max Plus 384 well plate reader. The slope of the linear portion for each well was determined and the fold increase in activity for each mutant was calculated.

Effect of pH on PAC-1 activation of procaspase-3. The effect of pH on procaspase-3 activation by PAC-1 was determined by diluting procaspase-3 in pH caspase assay buffer (25 mM MES, 25 mM Tris, 25 mM HEPES, 25 mM PIPES, 100 mM NaCl, 10 mM DTT, 0.1 mM EDTA, 0.1% CHAPS and 10% glycerol) to a concentration of 50 ng/mL. The buffer was then changed to various pH values and 90 µL was added to each well of a 96-well plate. PAC-1 was added to a concentration of 100 µM or DMSO was added as a control for each pH value. The plate was then incubated for 12 hours at 37° C. 10 µL of a 2 mM solution of Ac-DEVD-pNA in caspase assay buffer was then added to each well. The plate was read every 2 minutes at 405 nm for 2 hours in a Spectra Max Plus 384 plate reader (Molecular Devices, Sunnyvale Calif.). The slope of the linear portion for each well was determined and the fold increase in activation for each pH value was calculated.

Annexin V staining. 500 µL of media containing 200 µM PAC-1 or only DMSO as a control was added to the wells of a 24-well plate. 500 µL HL-60 cells at a concentration of $2 \times 10^6$ cells/mL were then added to the 24-well plate. The plate was incubated for 20 hours at 37° C. Cells were harvested by centrifugation and washed twice in PBS. The cells were then washed in AnnexinV binding buffer (10 mM HEPES, 140 mM NaCl, 2.5 mM CaCl2, pH 7.4) and resuspended in 100 µL of Annexin V binding buffer. 5 µL of annexin V, Alexa Fluor 488 conjugate was added and the tubes were incubated at room temperature for 15 minutes protected from light. 400 µL of Annexin V binding buffer was then added, followed by the addition of 1 µL of a 1 mg/mL solution of propidium iodide. The fluorescent intensity of each cell was determined by flow cytometry at 525 nm (green channel) and 675 nm (red channel). At least 50,000 cells were analyzed in each experiment.

Condensed chromatin staining. 500 µL of media containing 200 µM PAC-1 or only DMSO as a control was added to the wells of a 24-well plate. 500 µL HL-60 cells at a concentration of $2 \times 10^6$ cells/mL were then added to the 24-well plate. The cells were incubated for 20 hours and harvested by centrifugation. The cells were then washed in PBS buffer followed by the addition of ice-cold 100% ethanol. The cells were fixed overnight at 4° C. Fixed cells were incubated with 2 µg/mL Hoechst-33258 for 30 minutes at room temperature. A drop of cells was then added to a microscope slide and covered with a No. 1 thickness coverslip. Condensed chromatin was observed at 400× magnification on a Zeiss Axiovert 100 microscope.

Cell death inhibition by z-vad-fmk. 100 µL HL-60 cells at a concentration of $5 \times 10^5$ cells/mL were added to the wells of a 96-well plate. The cells were then incubated for 1 hour in the presence or absence of 100 µM z-vad-fmk, a cell-permeable pan caspase inhibitor. PAC-1 was then added at various concentrations, and the cells were incubated for an additional 24 hours. Cell death was quantitated by the addition of 20 µL of the MTS/PMS CellTiter 96 Cell Proliferation Assay reagent to each well. The plates were incubated at 37° C. for approximately 45 minutes until the colored product formed. The absorbance was then measured at 490 nm in a Spectra Max Plus 384 plate reader (Molecular Devices, Sunnyvale Calif.).

In vivo determination of mitochondrial membrane potential. 1 mL of HL-60 cells at a concentration of $1 \times 10^6$ cells/mL were added to the wells of a 24-well plate. PAC-1 was then added to a concentration of 100 µM or only DMSO was added as a control. The cells were incubated for various times, and the cells then were harvested by centrifugation. The cells were washed in PBS and resuspended in 1 mL of PBS. 10 µg of the JC-9 dye was added and the cells were incubated at room temperature for 10 minutes protected from light. The cells were then washed two times with PBS and brought up in 500 µL PBS. The fluorescent intensity of each cell was determined by flow cytometry at 525 nm (green channel) and 675 nm (red channel). 50,000 cells were analyzed in each experiment. The shift in the red channel was then used to determine the amount of mitochondrial membrane depolarization.

In vivo determination of caspase-3 like activity. The amount of caspase-3 like protease activity was determined by the amount of Ac-DEVD-pNA (N-acetyl-ASP-Glu-Val-Asp-p-nitroanilide) cleaved per minute by cell lysates. To accomplish this, 50 µL of media containing varying concentrations of PAC-1 was added to the wells of a 96-well plate. 50 µL of HL-60 cells at a concentration of $5 \times 10^6$ cells/mL were added to the plate and incubated for various times. After the incubation period, the plate was spun at 1000×g for 5 minutes to pellet the cells. The cells were then washed with 100 µL of PBS and resuspended in 150 µL of ice cold Caspase Assay Buffer. Each well was then sonicated to lyse the cells. 90 µL of cell lysate was transferred from each well into a new plate. Ac-DEVD-pNA was added into each well to give a final concentration of 200 µM. The plate was then read every 2 minutes at 405 nm for 2 hours in a Spectra Max Plus 384 plate reader (Molecular Devices, Sunnyvale Calif.). The slope of the linear portion for each well was determined and the amount of Ac-DEVD-pNA cleaved per minute was calculated.

In vivo determination of PARP cleavage. The amount of PARP cleavage was determined by using an in vivo PARP activity assay. To accomplish this, 50 µL of media containing 200 µM $NAD^+$ was added to the control wells of a 96-well plate. 50 µL of media containing 200 µM PAC-1 and 200 µM $NAD^+$ was then added to the experimental wells. 25 µL of HL-60 cells at a concentration of $5 \times 10^6$ cells/mL were then added to each well. The cells were incubated for various times and then spun at 1000×g for 5 minutes. The cell media was removed and replaced with 50 µL Lysing PARP Buffer (50 mM Tris, 10 mM MgCl2, pH 8.0, 1% Triton X-100) containing 25 mM $H_2O_2$. The plate was then incubated for 60 minutes at 37° C. To determine the amount of $NAD^+$ still present, 20 µL of 2 M KOH and 20 µL of a 20% (v/v) acetophenone (in ethanol) solution was added to each well of the 96-well plate. The plate was then incubated for 10 minutes at 4° C. 90 µL of an 88% (v/v) formic acid solution was added to each well of the 96-well plate. The plate was then incubated for 5 min. in an oven set to 110° C. The plate was allowed to cool and then read on a Criterion Analyst AD (Molecular Devices, Sunnyvale, Calif.) with an excitation of 360 nm, an emission of 445 nm and a 400 nm cutoff dichroic mirror. The fluorophore was excited using a 1000 W continuous lamp for $1.6 \times 10^5$ µs with 5 reads performed per well. The number of moles of $NAD^+$ cleaved per minute was then calculated and the remaining PARP activity as compared to control wells was determined.

Relative concentration of procaspase-3 in various cell lines. U-937, HL-60 and human bone marrow cells were harvested by centrifugation while all other cell lines were first trypsinized to release the cells and then harvested by centrifugation. All cells were washed in PBS and resupended in 1 mL of ice-cold 100% ethanol. Cells were fixed overnight at 4°

C. The cells were spun at 1000×g for 5 minutes, washed with PBS and 100 μL of a 1:100 dilution of anti-caspase-3 antibody in PBS was then added. The cells were incubated for 2 hours at room temperature followed by five PBS washes. The cells were then resuspended in 1 mL of a 1:10,000 dilution of anti-mouse Ab Cy3 labeled antibody for 2 hours at room temperature protected from light. The cells were washed five times with PBS and resuspended in 500 μL of PBS. The fluorescent intensity of each cell was determined by flow cytometry at 675 nm (red channel). At least 20,000 cells were analyzed in each experiment. The median of the population was used to determine the relative concentration of procaspase-3 in each cell line.

Determination of $IC_{50}$ values in various cell lines. 50 μL of media containing various concentrations of PAC-1 or etoposide was added to each well of a 96-well plate except control wells, which contained only DMSO. U-937, HL-60 and human bone marrow cells were harvested by centrifugation, while all other cell lines were first trypsinized before centrifugation. Cells were then resuspended in media and diluted to either $1×10^6$ cells/mL for U-937, HL-60 and human bone marrow cells or 50,000 cells/mL for all other cell lines. 50 μL of the cell solutions were then added to each well and the plates were incubated for either 24 or 72 hours for etoposide and PAC-1 respectively. Cell death was quantitated by the addition of 20 μL of the MTS/PMS CellTiter 96 Cell Proliferation Assay reagent to each well. The plates were then incubated at 37° C. for approximately one hour until the colored product formed. The absorbance was measured at 490 nm in a Spectra Max Plus 384 plate reader (Molecular Devices, Sunnyvale Calif.).

Data Analysis: The data from all flow cytometry experiments was analyzed using Summit Software (Cytomation, Fort Collins Colo.). All graphs were analyzed using Table Curve 2D.

Professor Ronald Hoffman (University of Illinois-Chicago Cancer Center) provided human bone marrow. Professor Guy Salvesen (Burnham Institute) provided the procaspase-3 and procaspase-7 expression vectors.

REFERENCE TO SEQUENCE LISTING—Appendix A. The separately accompanying sequence listing information, designated Appendix A, is to be considered and incorporated as part of the specification herewith.

TABLE 1

Overview of Sequence Listing information.

| SEQ ID NO: | Brief Description | Type |
|---|---|---|
| 1 | Procaspase-3; with amino acid DDD wild-type safety catch sequence (ACCESSION Number NM_004346) | DNA/RNA |
| 2 | automatic translation | PRT |
| 3 | procaspase-3 mutant ADD | DNA/RNA |
| 4 | automatic translation | PRT |
| 5 | procaspase-3 mutant DAD | DNA/RNA |
| 6 | automatic translation | PRT |
| 7 | procaspase-3 mutant DDA | DNA/RNA |
| 8 | automatic translation | PRT |
| 9 | procaspase-3 wild-type DDD | PRT |
| 10 | procaspase-3 mutant ADD | PRT |
| 11 | procaspase-3 mutant DAD | PRT |
| 12 | procaspase-3 mutant DDA | PRT |
| 13 | PCR primer1 | DNA |
| 14 | PCR primer2 | DNA |
| 15 | PCR primer3 | DNA |
| 16 | Procaspase-7 with amino acid DTD wild-type safety catch sequence (Accession Number NM_001227) | DNA/RNA |

TABLE 1-continued

Overview of Sequence Listing information.

| SEQ ID NO: | Brief Description | Type |
|---|---|---|
| 17 | automatic translation | PRT |
| 18 | Procaspase-7 DDD wild-type safety catch sequence | DNA/RNA |
| 19 | automatic translation | PRT |
| 20 | Procaspase-7 DTD wild-type safety catch, active site C to A mutant sequence | DNA/RNA |
| 21 | automatic translation | PRT |
| 22 | Procaspase-7 DDD wild-type safety catch, active site C to A mutant sequence | DNA/RNA |
| 23 | automatic translation | PRT |
| 24 | Procaspase-7 with amino acid DTD | PRT |
| 25 | Procaspase-7 DDD wild-type safety catch sequence | PRT |
| 26 | Procaspase-7 DTD wild-type safety catch, active site C to A mutant sequence | PRT |
| 27 | Procaspase-7 DDD wild-type safety catch, active site C to A mutant sequence | PRT |

EXAMPLE 2

Synthesis of Procaspase Activating Compounds

PAC-1 and other compounds are prepared according to the following schemes, e.g., Scheme 1 and/or Scheme 2. Further variations are prepared according to methods known in the art.

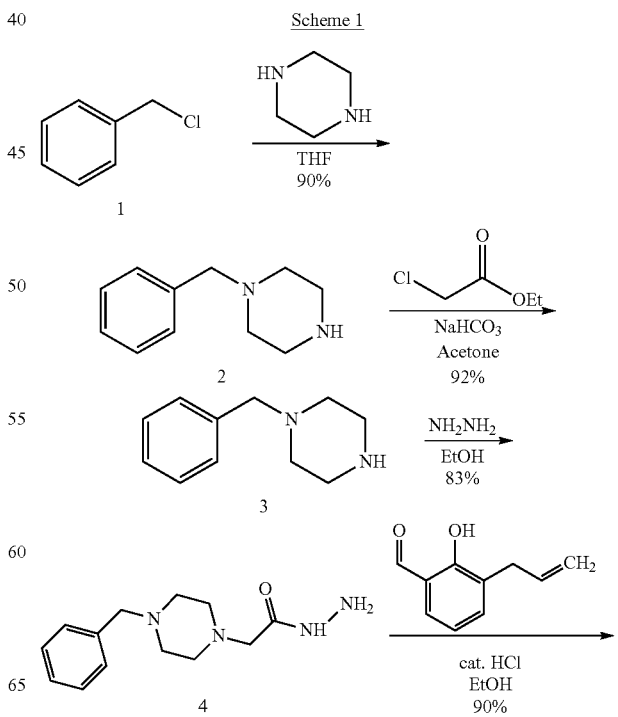

Scheme 1

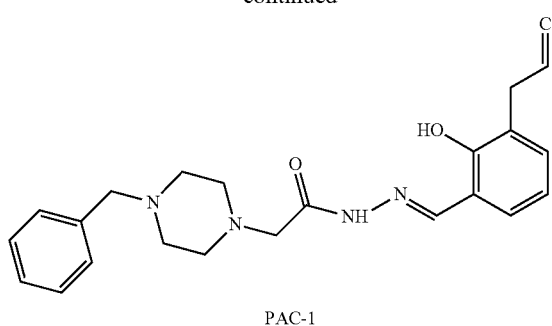
PAC-1
In a particular example, PAC-1 is prepared according to Scheme 2:
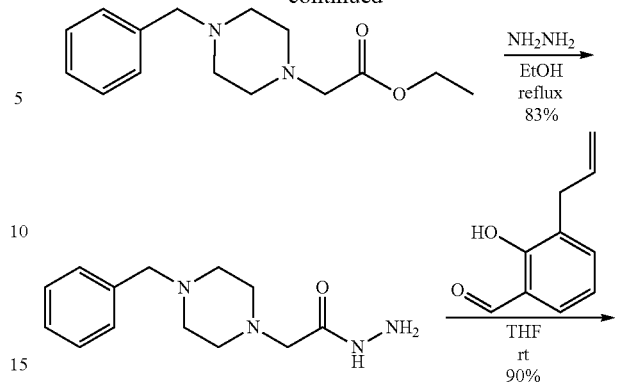
PAC-1 ~10 g
EXAMPLE 3
Analogs of PAC-1
Analog compounds of PAC-1 were prepared and assessed for the capability to directly activate purified procaspase-3 in vitro.
TABLE 2
Activity of PAC-1 and analog compounds.
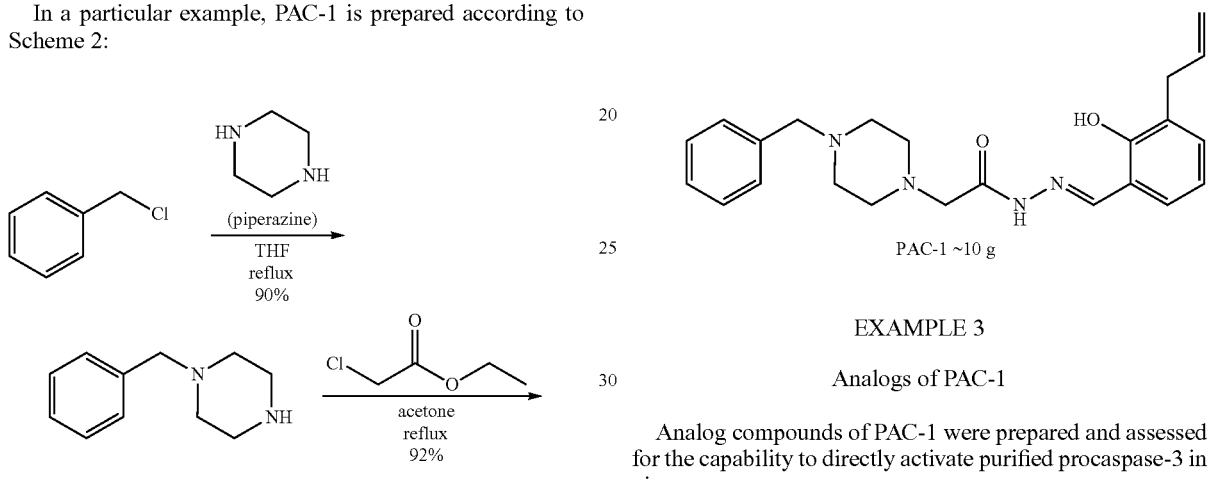

TABLE 2-continued

Activity of PAC-1 and analog compounds.

| Compound/Structure designation | Structure | Activity |
|---|---|---|
| 7 | [structure] | Inactive |
| 2 | [structure] | Inactive |
| 4 | [structure] | Inactive |

EXAMPLE 4

Pharmaceutical Embodiments

The following describes information relevant to pharmaceutical and pharmacological embodiments and is further supplemented by information in the art available to one of ordinary skill. The exact formulation, route of administration and dosage can be chosen by an individual physician in view of a patient's condition (see e.g. Fingl et. al., in The Pharmacological Basis of Therapeutics, 1975, Ch. 1 p. 1).

It should be noted that the attending physician would know how to and when to terminate, interrupt, or adjust administration due to toxicity, or to organ dysfunctions, etc. Conversely, the attending physician would also know to adjust treatment to higher levels if the clinical response were not adequate (in light of or precluding toxicity aspects). The magnitude of an administered dose in the management of the disorder of interest can vary with the severity of the condition to be treated and to the route of administration. The severity of the condition may, for example, be evaluated, in part, by standard prognostic evaluation methods. Further, the dose and perhaps dose frequency, can also vary according to circumstances, e.g. the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995) and elsewhere in the art. Suitable routes may include, for example, oral, rectal, transdermal, vaginal, transmucosal, or intestinal administration; parenteral delivery, including intramuscular, subcutaneous, or intramedullary injections, as well as intraocular, intrathecal, intravenous, or intraperitoneal administration.

For injection or other routes, agents of the invention may be formulated in aqueous solutions, preferably in physiologically compatible buffers such as Hanks' solution, Ringer's solution, water for injection, physiological saline buffer, or other solution. For transmucosal administration, penetrants appropriate to the barrier to be permeated can be used in the formulation. Such penetrants are generally known in the art.

Use of pharmaceutically acceptable carriers to formulate the compounds herein disclosed for the practice of the invention into dosages suitable for systemic or other administration is within the scope of the invention. With proper choice of carrier and suitable manufacturing practice, the compositions of the present invention, in particular those formulated as solutions, may be administered parenterally, such as by intravenous injection, or other routes. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, elixirs, solutions, suspensions and the like, e.g. for oral ingestion by a patient to be treated. For other routes, formulations can be prepared for creams, ointments, lotions, and the like.

Agents intended to be administered intracellularly may be administered using techniques well known to those of ordinary skill in the art. For example, such agents may be encapsulated into liposomes, other membrane translocation facilitating moieties, or other targeting moieties; then administered as described above. Liposomes can include spherical lipid bilayers with aqueous interiors. All molecules present in an aqueous solution at the time of liposome formation can be incorporated into the aqueous interior. The liposomal contents are both protected from the external microenvironment and, because liposomes fuse with cell membranes, are efficiently delivered into the cell cytoplasm. Additionally, due to hydrophobicity attributes, small organic molecules may be directly administered intracellularly.

Pharmaceutical compositions suitable for use in the present invention include compositions wherein the active ingredients are contained in an effective amount to achieve the intended purpose. Determination of the effective amounts is well within the capability of those skilled in the art, especially in light of the disclosure provided herein and other information in the art.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present invention may be manufactured in a manner that is itself known, e.g., by means of conventional mixing, dissolving, suspending, granulating, dragee-making, levitating, emulsifying, encapsulating, entrapping, lyophilizing, and other processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are optionally provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

EXAMPLE 5

Direct Induction of Apoptosis in Cancer Cells with a Small Molecule Activator of Procaspase-3

ABSTRACT: Mutation or aberrant expression of proteins in the apoptotic cascade is a hallmark of cancer. These changes prevent proapoptotic signals from being transmitted to the executioner caspases, thus preventing apoptotic cell death and allowing cellular proliferation. Caspase-3 and caspase-7 are the key executioner caspases, existing as inactive zymogens that are activated by upstream signals. Importantly, levels of procaspase-3 are significantly higher in certain cancerous cells relative to non-cancerous controls. Here we report the identification of a small molecule (PAC-1) that directly activates procaspase-3 to active caspase-3 in vitro with an $EC_{50}$ of 220 nanomolar, and induces apoptosis in a variety of cancer cell lines. In contrast to many known anticancer drugs, cells treated with PAC-1 show an immediate activation of procaspase-3, and the efficacy of PAC-1 is shown to be proportional to the amount of procaspase-3 contained in a cell. Derivatives of PAC-1 that do not activate procaspase-3 in vitro also have no proapoptotic activity. Cancerous cells isolated from primary colon tumors are considerably more sensitive to apoptotic induction by PAC-1 than the cells from adjacent non-cancerous tissue from the same patient; these cancerous cells contain on average about 7-fold more procaspase-3 than the cells from the adjacent non-cancerous primary tissue. In addition, the sensitivity to PAC-1 of the primary cells from the colon cancer tumors strongly correlates with the level of the procaspase-3 target. Finally, PAC-1 as a single entity was shown as active to retard the growth of tumors in three different mouse models, including two models where PAC-1 was administered orally. Thus PAC-1 directly activates procaspase-3 to caspase-3 in vivo, thereby allowing this compound to induce apoptosis even in cells that have defective apoptotic machinery. PAC-1 is the first small molecule known to directly activate procaspase-3; the direct activation of executioner caspases is an anti-cancer strategy that may prove beneficial in the many cancers in which procaspase-3 levels are elevated.

INTRODUCTION. A hallmark of cancer is its resistance to natural apoptotic signals. Depending on the cancer type, this resistance is typically due to either up- or down-regulation of key proteins in the apoptotic cascade, or to mutations in genes encoding these proteins. Such changes occur in both the intrinsic apoptotic pathway, which funnels through the mitochondria and caspase-9, and the extrinsic apoptotic pathway, which involves the action of death receptors and caspase-8. For example, alterations in proper levels of p53, Bim, Bax, Apaf-1, FLIP and many others have been observed in cancers and lead to a defective apoptotic cascade, one in which the upstream pro-apoptotic signal is not properly transmitted to activate the executioner caspases, caspase-3 and caspase-7. As most apoptotic pathways ultimately involve the activation of procaspase-3, these genetic abnormalities are effectively "breaks" in the apoptotic circuitry, and as a result such cells proliferate uncontrolled.

Given the central role of apoptosis in cancer, efforts have been made to develop therapeutics that target specific proteins in the apoptotic cascade. For instance, peptidic or small molecule binders to p53, proteins in the Bcl family, or to the IAPs have pro-apoptotic activity, as do compounds that promote the oligomerization of Apaf-1. However, because many of these compounds target early or intermediate positions on the apoptotic cascade, cancers with mutations in downstream proteins will likely be resistant to their effects. For therapeutic purposes it would be ideal to identify a small molecule that directly activates a proapoptotic protein far downstream in the apoptotic cascade. In addition, such a therapeutic strategy would have a higher likelihood of success if levels of that proapoptotic protein were elevated in cancer cells.

The conversion of procaspase-3 to caspase-3 results in the generation of the active "executioner" caspase that subsequently catalyzes the hydrolysis of a multitude of protein substrates. Active caspase-3 is a homodimer of heterodimers and is produced by proteolysis of procaspase-3. In vivo, this proteolytic activation typically occurs through the action of caspase-8 or caspase-9. To ensure that this zymogen is not prematurely activated, procaspase-3 has a tri-aspartic acid "safety catch" that blocks access to the IETD site of proteolysis. This safety catch enables procaspase-3 to resist autocatalytic activation and proteolysis by caspase-9. The position of the safety catch is sensitive to pH; thus, upon cellular acidification (as occurs during apoptosis) the safety catch is thought to allow access to the site of proteolysis, and active caspase-3 can be produced either by the action of caspase-9 or through an autoactivation mechanism.

Cells from certain types of cancerous tissue have elevated levels of procaspase-3. A study of primary isolates from 20 colon cancer patients revealed that on average procaspase-3 was elevated six-fold in such isolates relative to adjacent non-cancerous tissue. In addition, procaspase-3 levels are elevated in certain neuroblastomas, lymphomas, and liver cancers. In fact, a systematic evaluation of procaspase-3 levels in the 60 cell-line panel used by the NCI revealed that particular lung, melanoma, renal, and breast cancers show greatly enhanced levels of procaspase-3. Given the central importance of active caspase-3 to successful apoptosis, the high levels of procaspase-3 in certain cancerous cell types, and the intriguing safety catch-mediated suppression of its autoactivation, we reasoned that small molecules that directly activate procaspase-3 could be identified and that such molecules could have great potential in targeted cancer therapy. In this manuscript we report the in vitro identification of a small molecule activator of procaspase-3, PAC-1. PAC-1 is powerfully proapoptotic in cancer cell lines in a manner proportional to procaspase-3 levels, its proapoptotic effect is due to its direct and immediate activation of procaspase-3, and it is effective against primary colon cancer isolates and in three different mouse models of cancer.

Approximately 20,500 structurally diverse small molecules were screened for the ability to activate procaspase-3 in vitro. Procaspase-3 was expressed and purified in *E. coli* according to standard procedures. Procaspase-3 was added to the wells of a 384-well plate, and the compounds were added to a final concentration of about 40 µM (the final concentration of procaspase-3 was 50 ng/mL). Each plate was then incubated for two hours at 37° C., after which the caspase-3 peptidic substrate Ac-Asp-Glu-Val-Asp-p-nitroanilide (Ac-DEVD-pNa) was added to a concentration of 200 µM. The formation of the p-nitroaniline chromophore was followed at 405 nm over the course of two hours. Of the ~20,500 compounds evaluated, four induced a significant increase over background in the hydrolysis of the peptidic caspase-3 substrate. Of those four, one showed a strong dose dependent effect on in vitro procaspase-3 activation. As shown in FIG. 1A, this first procaspase-activating compound (PAC-1) gives half-maximal activation of procaspase-3 at a concentration of 0.22 µM. This compound is not simply increasing the activity of caspase-3 itself, as it has no effect on the catalytic activity of the fully processed caspase-3 enzyme (FIG. 1A).

Procaspase-3 consists of a N-terminal pro domain (residues 1-28), followed by a large subunit (17 kDa) and a small subunit (12 kDa) that are separated by an intersubunit linker.[22] In vivo, two procaspase-3 monomers assemble to form a homodimer that can be activated by cleavage at D175 in the intersubunit linker. The precise role of the pro domain is unclear, and it has been shown that cleavage in the intersubunit region alone is sufficient for full catalytic activity. Although procaspase-3 has enough catalytic activity to drive its own proteolytic maturation, it is highly resistant to this autoactivation due to the presence of the three amino acid safety catch. However, when the safety catch is mutated significant autoactivation of procaspase-3 is observed. To directly assess the ability of PAC-1 to catalyze the maturation of procaspase-3 to the active caspase-3, the procaspase-3 protein was incubated with 100 µM of PAC-1 for time points ranging from one to five hours. As shown by the Western blot in FIG. 1B, PAC-1 induces the cleavage of procaspase-3 in a time-dependant fashion, with >50% processing observed after 4 hours. In contrast, procaspase-3 incubated in buffer shows virtually no autoactivation over that same time span. PAC-1 was also effective in this assay at a concentration of 5 µM.

Alanine substitutions were then made in the key aspartic acid triad in the safety catch region of procaspase-3, residues Asp179, Asp180 and Asp181. Mutations at these positions all dramatically decreased the ability of PAC-1 to activate procaspase-3, with certain mutations more detrimental to activation of procaspase-3 by PAC-1 (FIG. 2A). Like caspase-3, caspase-7 also exists as an inactive zymogen that is activated by proteolysis. Caspase-3 and caspase-7 are both executioner caspases and have considerable structural homology. Procaspase-7 is also predicted to have a similar safety catch region, although it has only two aspartic acids in the key triad (Asp-Thr-Asp), instead of three. As indicated by the data in FIG. 2B, PAC-1 can also activate procaspase-7, although in a less efficient manner than its activation of procaspase-3 ($EC_{50}$ of 4.5 µM versus 0.22 µM for procaspase-3 activation). The potency of procaspase-7 activation by PAC-1 is similar to its effect on the Asp-Ala-Asp mutant of procaspase-3 ($EC_{50}$=2.77 µM). As expected, the effect of PAC-1 is abolished at low pH values where procaspase-3 undergoes rapid autoactivation (FIG. 2C).

PAC-1 was found to induce apoptosis in a variety of cancer cell lines. In HL-60 cells addition of PAC-1 leads to considerable phosphatidylserine exposure on the cell membrane accompanied by significant chromatin condensation (FIGS. 3A, 3B). In addition, the compound induces cleavage of the caspase substrate PARP-1 (as assessed by an in vivo PARP activity assay) and causes mitochondrial membrane depolarization (see below). Significant cellular blebbing of PAC-1 treated cells was also observed by microscopy. Furthermore, the toxicity of PAC-1 could be abolished in the presence of the caspase inhibitor z-VAD-fmk.

If PAC-1 is indeed inducing apoptosis via direct activation of procaspase-3, then the time course of apoptotic events should be altered relative to that observed with standard proapoptotic agents. Etoposide is well known to induce apoptosis through the intrinsic pathway; thus, mitochondrial membrane depolarization is followed by procaspase-3 activation in etoposide-treated cells. Indeed, in HL-60 cells treated with 10 µM etoposide, mitochondrial membrane depolarization is observed, followed by detection of caspase-3-like activity (FIG. 4A). In contrast, treatment of cells with PAC-1 gives a markedly different result. With this compound, the first observed biochemical hallmark of apoptosis is caspase-3-like enzymatic activity, with activity noted within minutes of PAC-1 addition and 50% activation taking place in just over 2 hours and well before any significant mitochondrial membrane depolarization (FIG. 4B). In addition, PARP-1 activity is rapidly reduced in cells treated with PAC-1, whereas this reduction is observed at later time points in etoposide treated cells (FIG. 4C); control experiments show that PAC-1 does not directly inhibit enzymatic activity of PARP-1. In the typical sequence of apoptotic events the mitochondrial membrane depolarizes, caspases are activated, and caspase substrates (such as PARP-1) are cleaved. The observation that cells treated with PAC-1 show a rapid activation of caspase-3/-7 (before mitochondrial membrane depolarization) and a rapid cleavage of a caspase substrate (PARP-1) is indicative of PAC-1 exerting its cellular toxicity through the direct activation of procaspase-3.

Figure 4E:
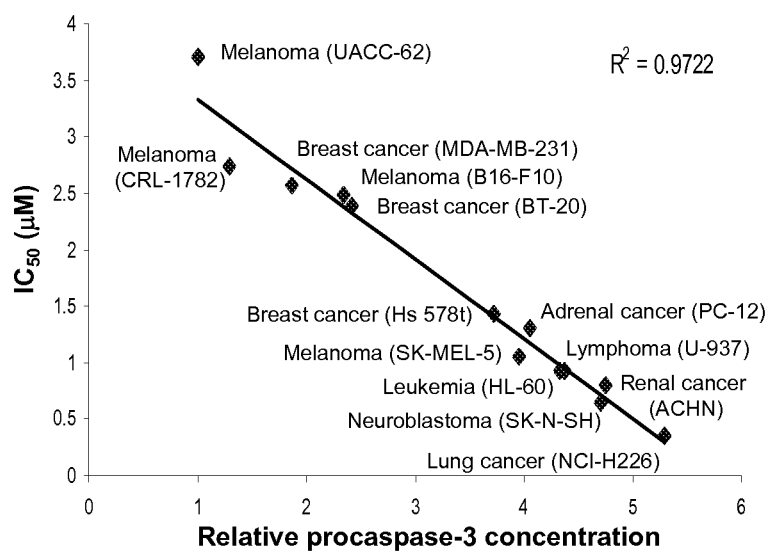

To further define the potency of PAC-1, the ability of this compound to induce cell death in cancer cell lines with varying levels of procaspase-3 was assessed. A determination was first made of the levels of procaspase-3 present in multiple cancer cell lines (leukemia, lymphoma, melanoma, neuroblastoma, breast cancer, lung cancer, adrenal cancer and renal cancer). The $IC_{50}$ values for cell death induction were obtained for PAC-1 versus these cell lines. The combined data shows a strong correlation between cellular concentration of procaspase-3 and sensitivity to PAC-1 (FIG. 4D, FIG. 4E). PAC-1 is most potent versus the lung cancer cell line NCI-H226, with an $IC_{50}$ of 0.35 µM. We found this cell line to have a concentration of procaspase-3 that is greater than five times that of baseline levels. Importantly, there is one cancer cell line (MCF-7, breast cancer cells) that is known to have no expression of procaspase-3. PAC-1 has virtually no effect on MCF-7 cells, inducing death with an $IC_{50}$>75 µM.

In contrast, etoposide showed no such correlation between potency in cell culture and cellular levels of procaspase-3. For instance, etoposide was ineffective ($IC_{50}$>50 µM) in inducing death in three of the melanoma cell lines (UACC-62, CRL-1872, and B16-F10), the breast cancer cell line (Hs 578t), and the lung cancer cell line (NCI-H226); these cell lines have procaspase-3 levels of 1.0, 2.4, 1.9, 3.7, and 5.3, respectively. Etoposide was effective ($IC_{50}$<1 µM) versus HL-60, U-937, SK-N-SH and PC-12, which have procaspase-3 levels of 4.3, 4.0, 4.7, and 4.4, respectively. Thus, overall there is no correlation between procaspase-3 levels and $IC_{50}$ for etoposide.

Several derivatives of PAC-1 were synthesized and evaluated for both their procaspase-3 activating properties and their effects on cancer cells in cell culture (Table 3). The PAC-1 derivative that lacks the allyl group (de-allyl PAC-1) is able to induce procaspase-3 activation and cell death at levels similar to PAC-1. However, all other derivatives showed no activity in either assay. Thus, while it appears the allyl group is dispensable for biological activity, the phenolic hydroxyl and aromatic rings are all critical for PAC-1 activity. This data is also consistent with the proposed mechanism of action of PAC-1; compounds that do not activate procaspase-3 in vitro have no proapoptotic effect on cancer cells in culture.

Figure 5A:
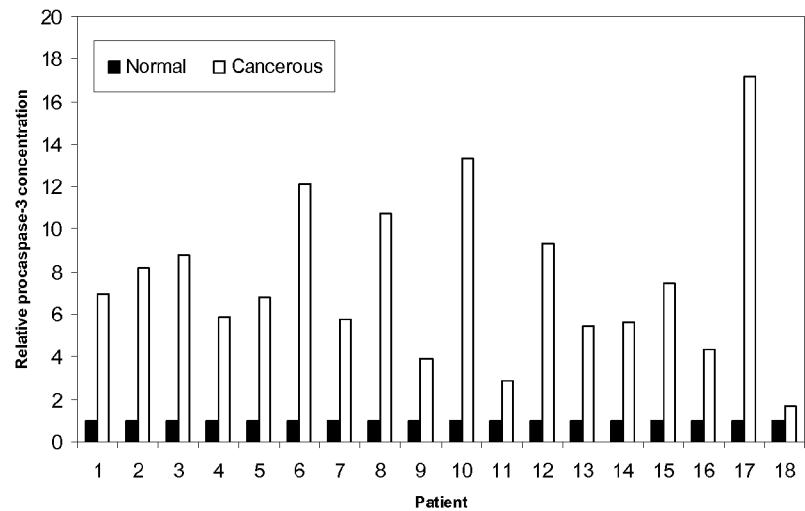
FIG. 5A illustrates relative procaspase-3 levels in normal and cancerous cells from several patients.
Figure 5B:
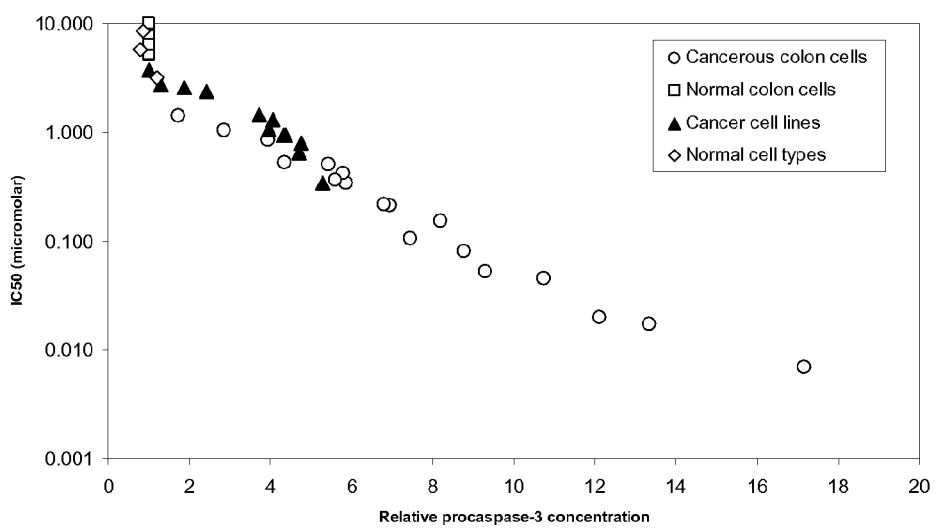
FIG. 5B illustrates $IC_{50}$ levels for PAC-1 in a variety of cell types having a range of relative procaspase-3 levels.
Figure 6A:
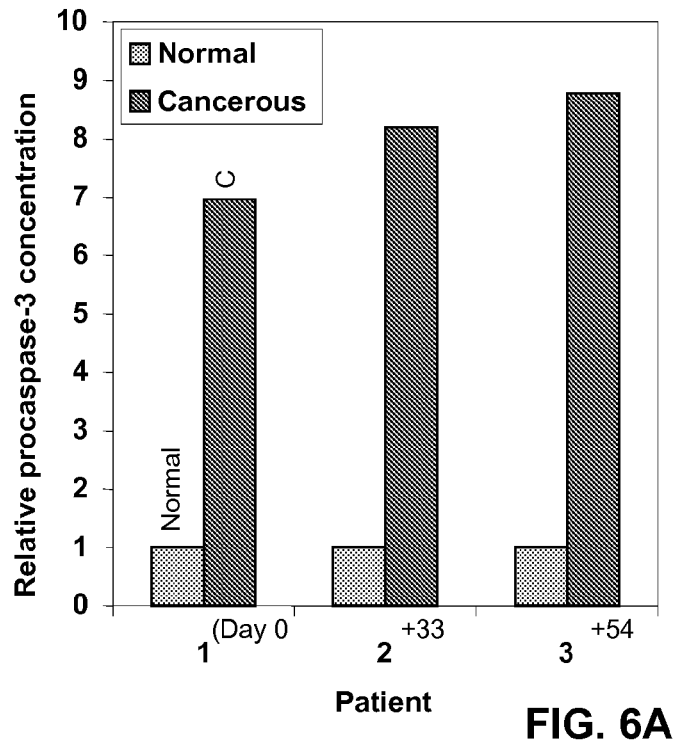
FIG. 6A illustrates relative procaspase-3 levels in normal and cancerous cells of three patients.
Figure 6B:
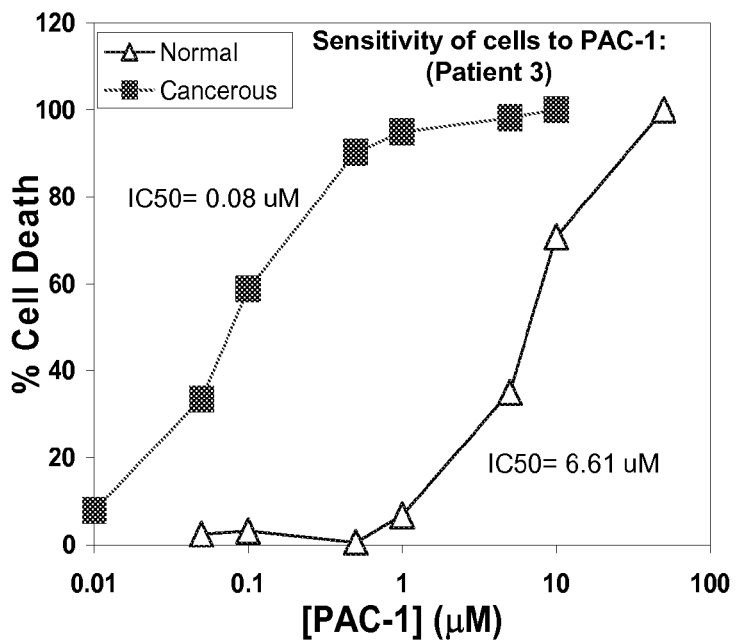
FIG. 6B illustrates the sensitivity of normal and cancerous cells from Patient 3 to treatment with PAC-1.

To test this direct, small molecule-mediated procaspase-3 activation strategy in clinical isolates of cancer, we obtained freshly resected colon tumors (together with adjacent non-cancerous tissue) from 18 patients from Carle Foundation Hospital (Urbana, Ill.). The cancerous and non-cancerous tissue was separated, and the cells derived from these were evaluated for their levels of procaspase-3 and their sensitivity to PAC-1. As shown in FIG. 5A, in all cases the cancerous cells had elevated levels (1.7- to 17.2-fold, with an average of 7.6-fold elevation) of procaspase-3 relative to the cells from the adjacent non-cancerous tissue from the same patient. Further, these cancerous cells were quite susceptible to death induction by PAC-1. PAC-1 induced cell death in the primary cancerous cells with $IC_{50}$ values from 0.007-1.41 µM, while PAC-1 induced cell death in the adjacent non-cancerous tissue with $IC_{50}$ values from 5.02-9.98 µM (FIG. 5B and Table 4). The cancerous tissue that had elevated levels of procaspase-3 was extremely sensitive to PAC-1. For example, PAC-1 induced death in the cancer cells from patient 17 with an $IC_{50}$ of 7 nM, and these cells were over 700-fold more sensitive to PAC-1 than cells from the adjacent normal tissue. See also FIG. 6A showing relative procaspase-3 concentrations in normal and cancerous samples from Patients 1, 2, and 3 over a period of time of about 54 days; FIG. 6B illustrates that cells in cancerous tissue can be greater than about 80-fold more sensitive to PAC-1 in comparison with normal tissue.

In addition to cells from the non-cancerous tissue of the 18 patients, PAC-1 was also evaluated against four other non-cancerous cell types: white blood cells isolated from the bone marrow of a healthy donor, Hs888Lu (lung fibroblast cells), MCF-10A (breast fibroblast cells), and Hs578Bst (breast epithelial cells). Notably, the non-cancerous cell types are among those with the lowest amount of procaspase-3, and PAC-1 is comparatively less able to induce death in these cells, with $IC_{50}$ values of 3.2-8.5 µM (FIG. 5B, green diamonds). As is apparent from FIG. 5B, PAC-1 induces death in a wide variety of cell types (non-cancerous cell lines, non-cancerous primary cells, cancerous cell lines, primary cancerous cells) in a manner directly related to the level of procaspase-3. The elevation of procaspase-3 in cancerous cells allows PAC-1 to selectively induce death in these cell types.

Figure 5C:
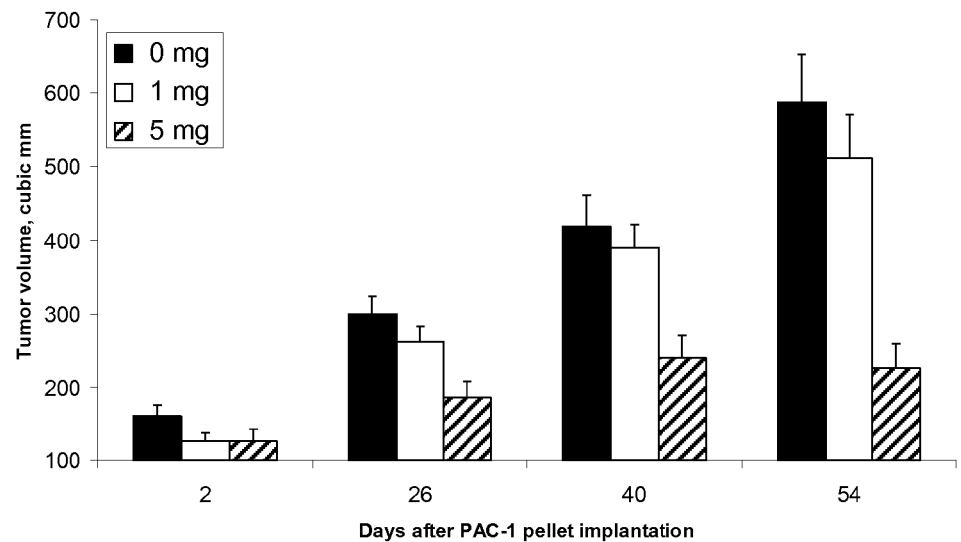
FIG. 5C illustrates the effect of treating animals with PAC-1 on outcomes of tumor growth.

PAC-1 was evaluated in a mouse xenograft model using a slow release mode of drug delivery. In this model, subcutaneous tumors were formed in ovariectomized female athymic BALB/c (nude) mice using the ACHN (renal cancer) cell line. Once the tumors were measured to be greater than about 30 mm$^2$, drug was administered via the implantation of a pellet of PAC-1 and cholesterol, providing for slow and steady levels of compound release. Three groups of mice were used, with pellets containing 0 mg, 1 mg, and 5 mg of PAC-1, six mice per group, with four tumors per mouse. Tumor sizes were monitored for about 8 weeks. As shown in FIG. 5C, tumor growth is significantly retarded in the mice that were implanted with the pellet containing 5 mg of PAC-1. Food intake evaluation in the last week of the experiment showed no difference in food consumption between the three groups of mice. After the mice were sacrificed, plasma samples were taken from each mouse, and the PAC-1 content of each was analyzed. For mice that received a 5 mg pellet of PAC-1, this analysis revealed PAC-1 to be present at a concentration of 5 nM in the plasma after the 54 day experiment.

Figure 5D:
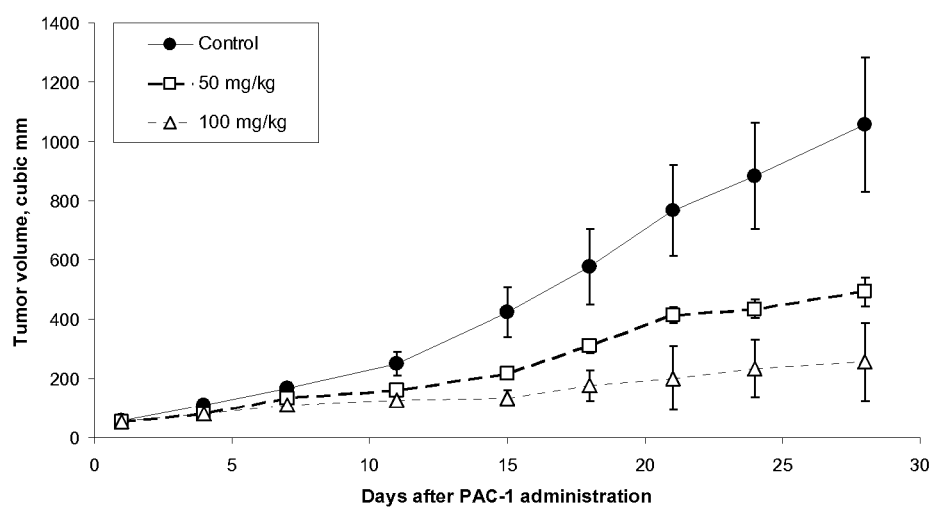
FIG. 5D illustrates the effect of oral treatment of animals with PAC-1 on outcomes of tumor growth.

PAC-1 was evaluated in a second mouse xenograft model, this one using oral administration as the drug delivery mode. In this model, subcutaneous xenograft tumors were formed in male athymic BALB/c-nu/nu mice (5 weeks old, SLC, Hamamaysu, Japan) using the NCI-H226 (lung cancer) cell line, eight mice per group, three tumors per mouse. After formation of the tumors in the mice, the mice were treated with PAC-1 via oral gavage once a day for 21 days at a concentration of 0, 50, or 100 mg/kg and sacrificed 1 week later. As clearly indicated by the graph in FIG. 5D, oral administration of PAC-1 significantly retards tumor growth in a dose-dependent manner.

Finally, PAC-1 was evaluated in a mouse model where the NCI-H226 cells were injected into male athymic BALB/c-nu/nu mice via tail vein injection. The total experiment lasted 28 days; the mice were treated once a day with PAC-1 (100 mg/kg) via oral gavage on days 1-4 and 7-11. On other days the mice did not receive PAC-1. A second group of mice received only vehicle. After 28 days the mice were sacrificed, and their lungs were examined. As shown in FIG. 5E, there is a clear difference between the lung of the control mouse (with obvious gray tumor mass) and the lung of the PAC-1 treated mouse. Results are also shown in a panel from an animal treated with gefitinib (Iressa™; AstraZeneca).

Cancerous cells typically have a reduced sensitivity to proapoptotic signals due to the mutation or aberrant expression of an assortment of proteins in the apoptotic cascade. As such, many types of cancer are notoriously resistant to not only the endogenous signals for apoptotic cell death, but also to chemotherapeutic agents that act through similar mechanisms. The paradoxical elevation of procaspase-3 levels in certain cancers provides an opportunity to use this existing intracellular pool of protein to directly induce apoptosis, thus bypassing the often non-functional upstream portion of the cascade. PAC-1 induces the autoactivation of procaspase-3 in vitro. In cell culture, PAC-1 treatment induces rapid caspase-3-like activity. It is likely that the caspase-3 mediated cleavage of anti-apoptotic proteins (Bcl-2, Bcl-XL, etc.) then induces depolarization of the mitochondrial membrane and amplifies apoptosis. Further, the potency of PAC-1 toward a variety of cancerous and non-cancerous cell types is proportional to the concentration of procaspase-3 in the cell. As the primary cancerous cells isolated from resected colon tumors have elevated levels of procaspase-3, these cells are considerably more sensitive to PAC-1 than cells from adjacent non-cancerous tissue. It is worth noting that several of the cell lines against which PAC-1 is effective have faulty apoptotic pathways that make them resistant to apoptosis; for instance, Apaf-1 expression is dramatically decreased in SK-MEL-5 cells, and Bcl-2 is overexpressed in the NCI-H226 lung cancer cell line. Finally, PAC-1 is effective in three different mouse models of cancer, including two where PAC-1 is administered orally.

Data presented herein support the notion that procaspase-3 activating compounds can be exceedingly effective against a variety of common cancers in which procaspase-3 levels are aberrantly high. Assessment of procaspase-3 levels in cancer biopsies is simple and rapid; as such, the potential effectiveness of a compound such as PAC-1 can be assessed a priori with a high degree of accuracy. Such personalized medicine strategies can be preferential to therapies that rely on general cytotoxins and can be valuable in anti-cancer therapy.

Professor Guy Salvesen (Burnham Institute) provided the procaspase-3 and procaspase-7 expression vectors.

Figure Legends

Figure 1B:
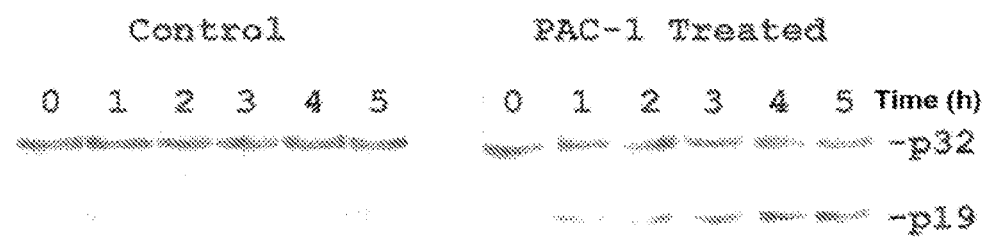
Figure 2A:
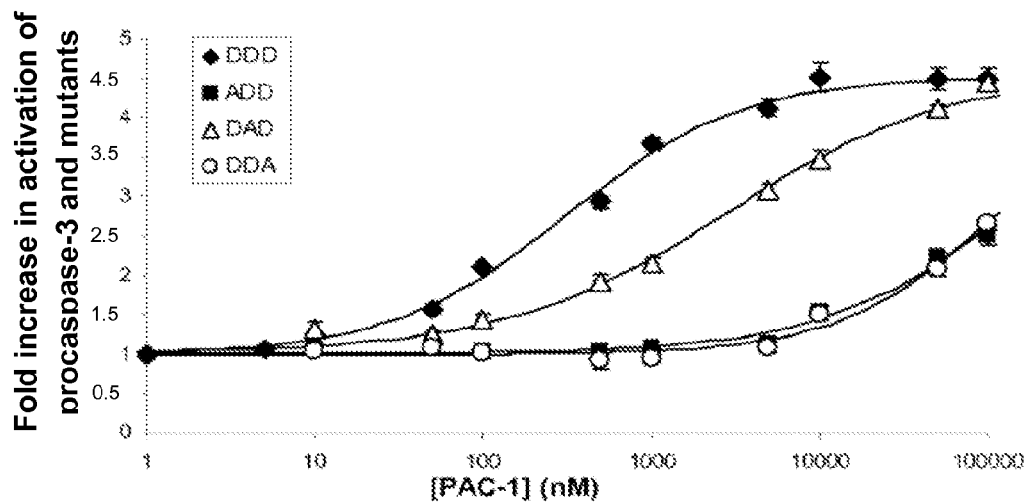
FIG. 2. A) Activation of mutants in the "safety catch" region of procaspase-3 by PAC-1. PAC-1 has an $EC_{50}$ for activation of 0.22 μM on wild type procaspase-3 (DDD), and corresponding $EC_{50}$ values of 2.77 μM (DAD), 113 μM (DDA), and 131 μM (ADD) for certain mutants. B) PAC-1 activates procaspase-7 with an $EC_{50}$ of 4.5 μM. C) Dependence of PAC-1 activation of procaspase-3 on pH. At low pH the safety catch is "off", and procaspase-3 is essentially maximally activated. Error bars represent standard deviations from the mean.
Figure 2B:
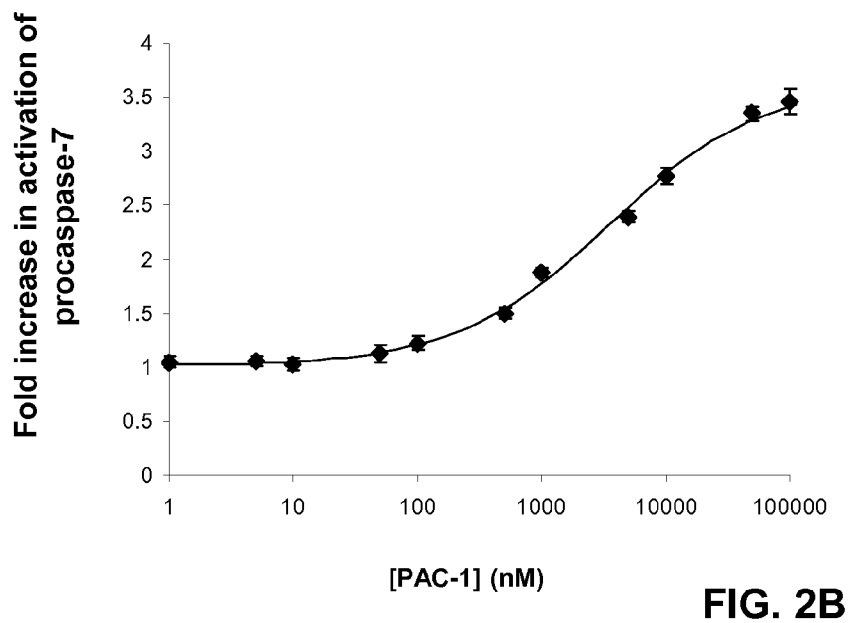
Figure 2C:
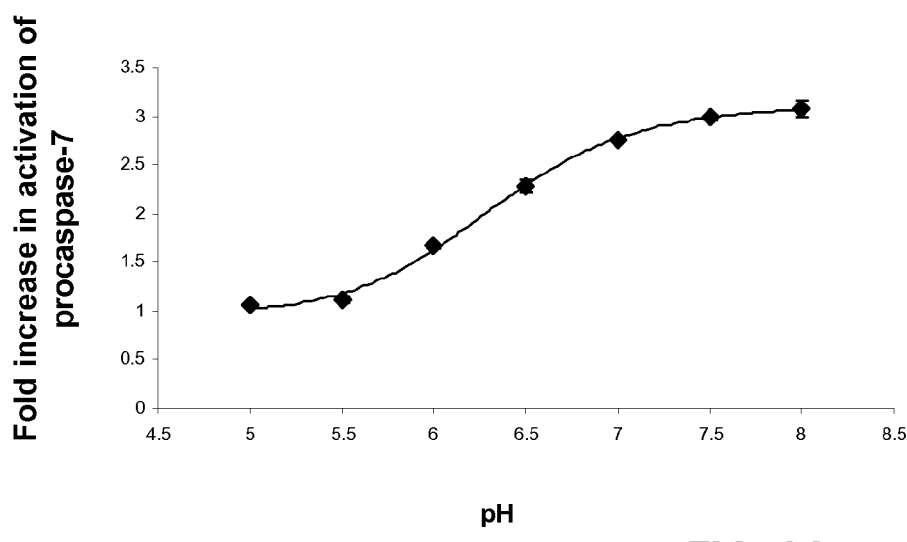

FIGS. 1 and 2. The structure of PAC-1 is shown elsewhere in the specification. FIG. 1A) In vitro activation of procaspase-3 and active caspase-3 by PAC-1. PAC-1 activates procaspase-3 with an $EC_{50}=0.22$ μM. FIG. 1B) Cleavage of procaspase-3 to active caspase-3 as induced by PAC-1. Procaspase-3 was recombinantly expressed in *E. coli* with an N-terminal His-6 tag and purified. Immunoblotting was performed with an anti-His-6 antibody. In the absence of PAC-1 no maturation of procaspase-3 is observed. In the presence of 100 μM PAC-1, cleavage to generate the p19 fragment is observed within 1 h, and >50% cleavage is observed after 4 h. PAC-1 is also effective at 5 μM in this assay. FIG. 2A) Activation of mutants in the "safety catch" region of procaspase-3 by PAC-1. PAC-1 has an $EC_{50}$ for activation of 0.22 μM on wild type procaspase-3 (DDD), and corresponding $EC_{50}$ values of 2.77 μM (DAD), 113 μM (DDA), and 131 μM (ADD) for the mutants. FIG. 2B) PAC-1 activates procaspase-7 with an $EC_{50}$ of 4.5 μM. FIG. 2C) Dependence of PAC-1 activation of procaspase-3 on pH. At low pH the safety catch is off and procaspase-3 is essentially maximally activated. Error bars represent standard deviations from the mean.

FIGS. 3 and 4. PAC-1 induces apoptosis in HL-60 cells. FIG. 3A) Phosphatidylserine exposure (as measured by Annexin-V staining) after a 20 h treatment with 100 μM PAC-1. PAC-1 is also effective at 5 μM in this assay (see Supporting FIG. 2). FIG. 3B) Chromatin condensation as visualized by Hoescht staining after a 20 h treatment with 100 μM PAC-1. FIG. 4A) Mitochondrial membrane depolarization (MMP) and caspase-3 like activity in HL-60 cells treated with 10 μM etoposide. FIG. 4B) Mitochondrial membrane depolarization (MMP) and caspase-3 like activity in HL-60 cells treated with 100 μM PAC-1. FIG. 4C) PAC-1 treatment (100 μM) induces a rapid decrease in cellular PARP activity in HL-60 cells, consistent with an immediate activation of cellular caspase-3/-7. In contrast, etoposide (10 μM) treated cells show a decrease in PARP activity at much later time points. FIG. 4D and FIG. 4E) PAC-1 induces cell death in a procaspase-3 dependant manner. For a number of diverse cancerous cell lines, the procaspase-3 levels were determined (by flow cytometry with an antibody to procaspase-3) and the $IC_{50}$ of PAC-1 was measured (through a 72 h treatment with a range of PAC-1 concentrations and quantitation using the MTS assay). PAC-1 is quite potent ($IC_{50}=0.35$ μM) in the NCI-H226 lung cancer cell line known to have high levels of procaspase-3. Error bars represent standard deviations from the mean.

Table 3. PAC-1 and de-allyl PAC-1 activate procaspase-3 in vitro and induce death in cancer cells in cell culture, but other structural analogues have no procaspase-3 activating effect in vitro and give no induction of death in cell culture.

FIG. 5. FIG. 5A) Procaspase-3 levels are elevated in cells derived from freshly resected colon cancer tissue. Freshly resected primary colon tumors (together with adjacent non-cancerous tissue) were obtained from 18 different patients, the cancerous and non-cancerous tissue were separated, and the procaspase-3 levels were measured for each using an antibody to procaspase-3 and flow cytometry. On average, cells from the cancerous tissue have a 7.6-fold elevation in procaspase-3 as compared to the cells derived from the adjacent non-cancerous tissue from the same patient. FIG. 5B) PAC-1 induces cell death in a manner proportional to the cellular level of procaspase-3. The red circles represent the primary cancerous cells from the 18 colon tumors. The black triangles represent the same cancer cell lines depicted in FIG. 4D. The green diamonds are four non-cancerous cell types: Hs888Lu (lung fibroblast cells), MCF-10A (breast fibroblast cells), Hs578Bst (breast epithelial cells), and white blood cells isolated from the bone marrow of a healthy donor. The blue squares are the primary non-cancerous cells isolated from the tumor margins of the 18 patients. Table 4) Cells derived from primary colon cancer tissue are considerably more sensitive to death induction by PAC-1 than are cells derived from adjacent non-cancerous tissue from the same patient. FIG. 5C) PAC-1 reduces the growth of tumors in a xenograft model of cancer. Tumors were formed with the ACHN (renal cancer) cell line by subcutaneous injection, with six mice in each group, and four tumors per mouse. Once the tumors grew to about 30 mm$^2$, PAC-1 was implanted as a cholesterol pellet. Error bars represent standard error from the mean. FIG. 5D) Oral administration of PAC-1 significantly retards tumor growth in a mouse xenograft model. Tumors were formed using the NCI-H226 (lung cancer) cell line by subcutaneous injection, eight mice in each group, and three tumors per mouse. PAC-1 or vehicle was administered once a day by oral gavage on days 1-21. Error bars represent standard error from the mean. FIG. 5E) Oral administration of PAC-1 significantly retards tumor growth in an i.v. injection model. Mice were injected i.v. with the NCI-H226 (lung cancer) cell line. The mice were treated with PAC-1 (100 mg/kg) via oral gavage following the protocol as described in the text. Images show the lungs of the mice that did not receive PAC-1 and have a large amount of gray tumor mass on the lung. In contrast, the mice that did receive PAC-1 have almost no visible gray matter.

TABLE 3
Selected compounds indicating activity levels.
| Compound | EC$_{50}$ (μM) for procaspase-3 activation | IC$_{50}$ (μM) for death induction in HL-60 cells |
|---|---|---|
| 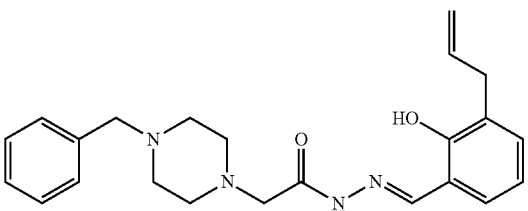<br>PAC-1 | 0.22 | 0.92 |
| 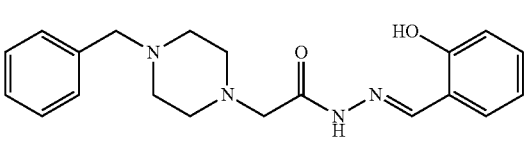<br>de-allyl PAC-1 | 0.43 | 1.74 |
| 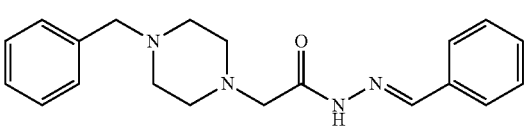 [SMILES: O=C(CN1CCN(Cc2ccccc2)CC1)N/N=C/c1ccccc1] | >50 | >100 |
| 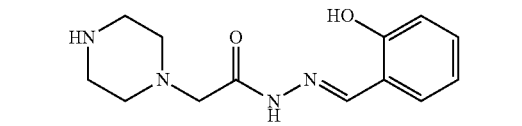 [SMILES: O=C(CN1CCNCC1)N/N=C/c1ccccc1O] | >50 | >100 |
| 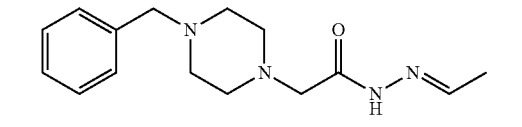 [SMILES: C/C=N/NC(=O)CN1CCN(Cc2ccccc2)CC1] | >50 | >100 |
| 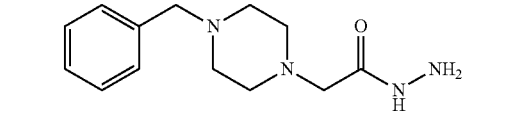 [SMILES: NNC(=O)CN1CCN(Cc2ccccc2)CC1] | >50 | >100 |
| 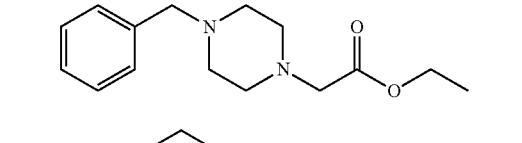 | >50 | >100 |
| 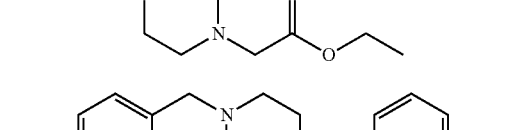 | >50 | >100 |
| 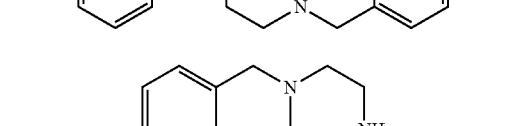 | >50 | >100 |
|  | >50 | >100 |

TABLE 4

Concentration levels of PAC-1 activity in patients.

| Patient | PAC-1, IC$_{50}$ μM | |
|---|---|---|
| | Normal | Cancerous |
| 1 | 6.78 | 0.212 |
| 2 | 9.79 | 0.154 |
| 3 | 6.61 | 0.080 |
| 4 | 9.50 | 0.340 |
| 5 | 6.88 | 0.216 |
| 6 | 6.28 | 0.020 |
| 7 | 7.34 | 0.422 |
| 8 | 5.67 | 0.045 |
| 9 | 6.54 | 0.844 |
| 10 | 9.98 | 0.017 |
| 11 | 5.94 | 1.030 |
| 12 | 5.63 | 0.052 |
| 13 | 5.50 | 0.499 |
| 14 | 7.58 | 0.366 |
| 15 | 5.96 | 0.106 |
| 16 | 5.02 | 0.527 |
| 17 | 5.17 | 0.007 |
| 18 | 6.39 | 1.410 |

EXAMPLE 6

Testing of PAC-1 in Mouse Model of Lung Cancer

Figure 7:
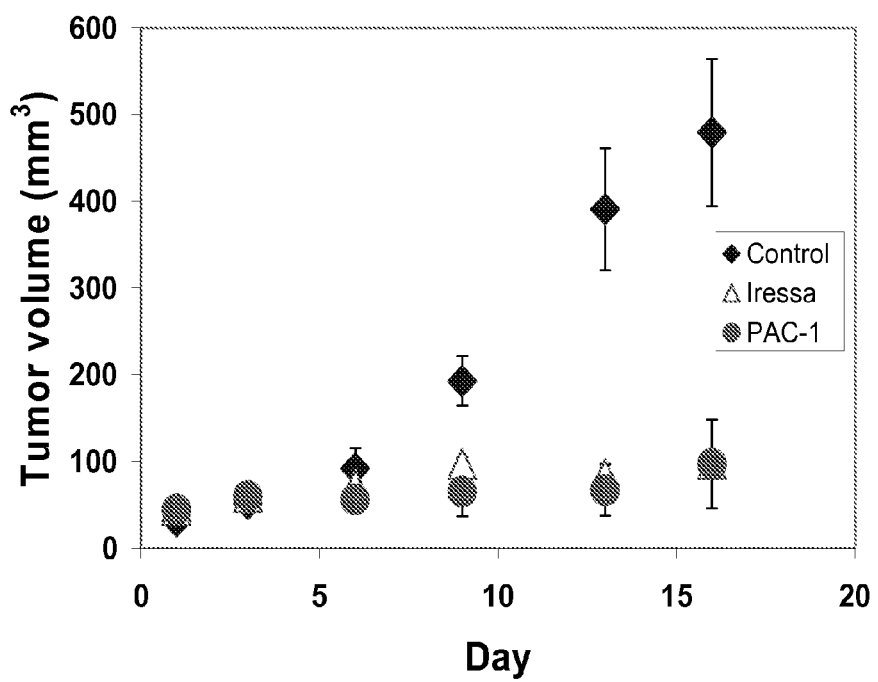
FIG. 7 illustrates results of administering PAC-1 intraperitoneally in the context of a mouse model of lung cancer.

A xenograft model was employed using NCI-H226 (lung cancer) cells. PAC-1 was given intraperitoneally (i.p.) at 10 mg/kg. A comparison of efficacy was performed with gefitinib (Iressa™; AstraZeneca, Wilmington, Del.) at 40 mg/kg using 5 mice per group. Results are shown in FIG. 7, indicating that PAC-1 was associated with reducing growth in tumor volume.

EXAMPLE 7

Combinatorial Derivatives, Synthesis, and Therapeutic Use

A number of compounds are prepared as derivatives of the PAC-1 structure. A hydrazide group is reacted with an aldehyde group to yield a combinatorial library of derivative compounds.

Figure 8A:
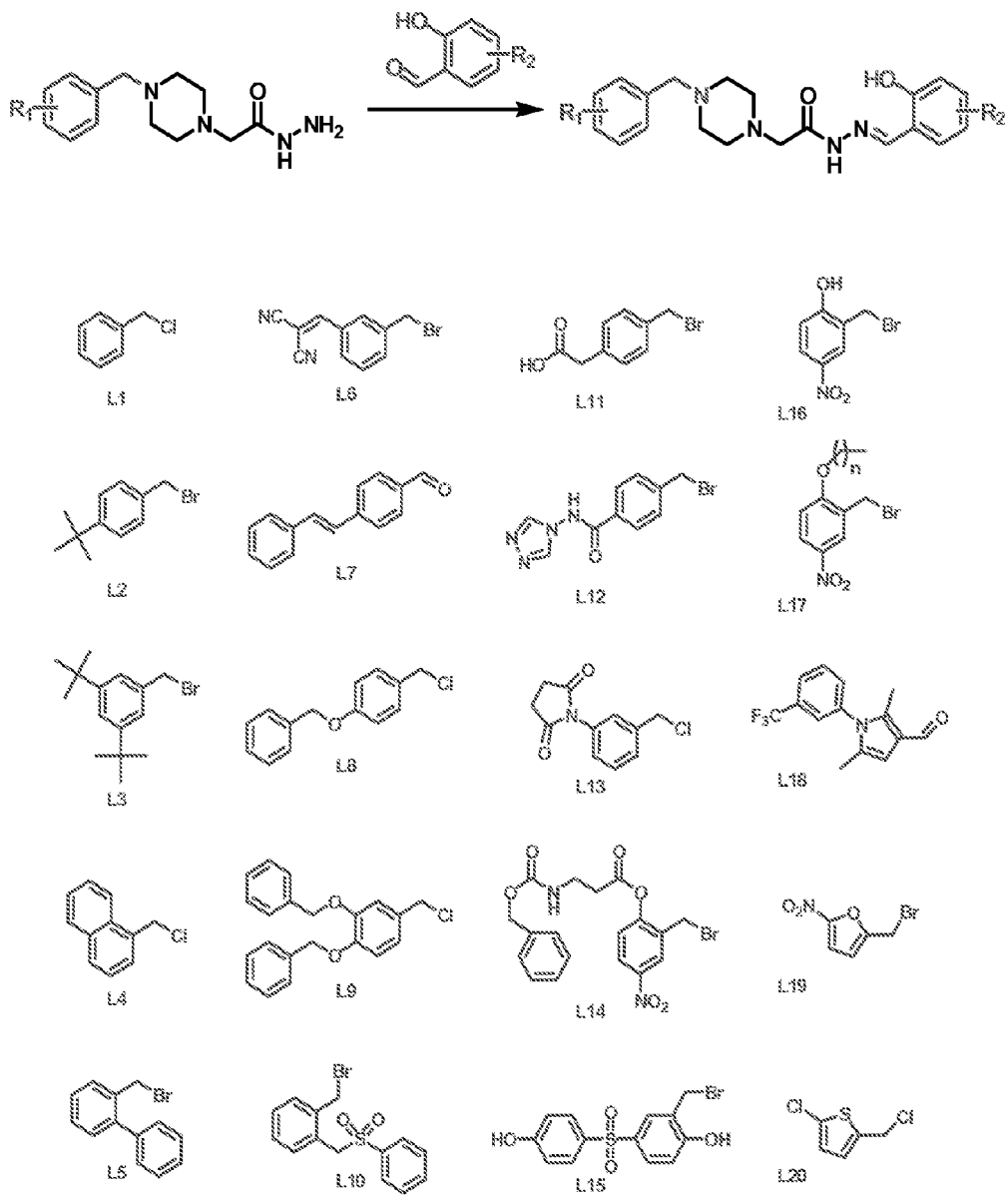
FIGS. 8A and 8B illustrate structures for compounds of PAC-1 derivatives and a combinatorial library.
Figure 8B:
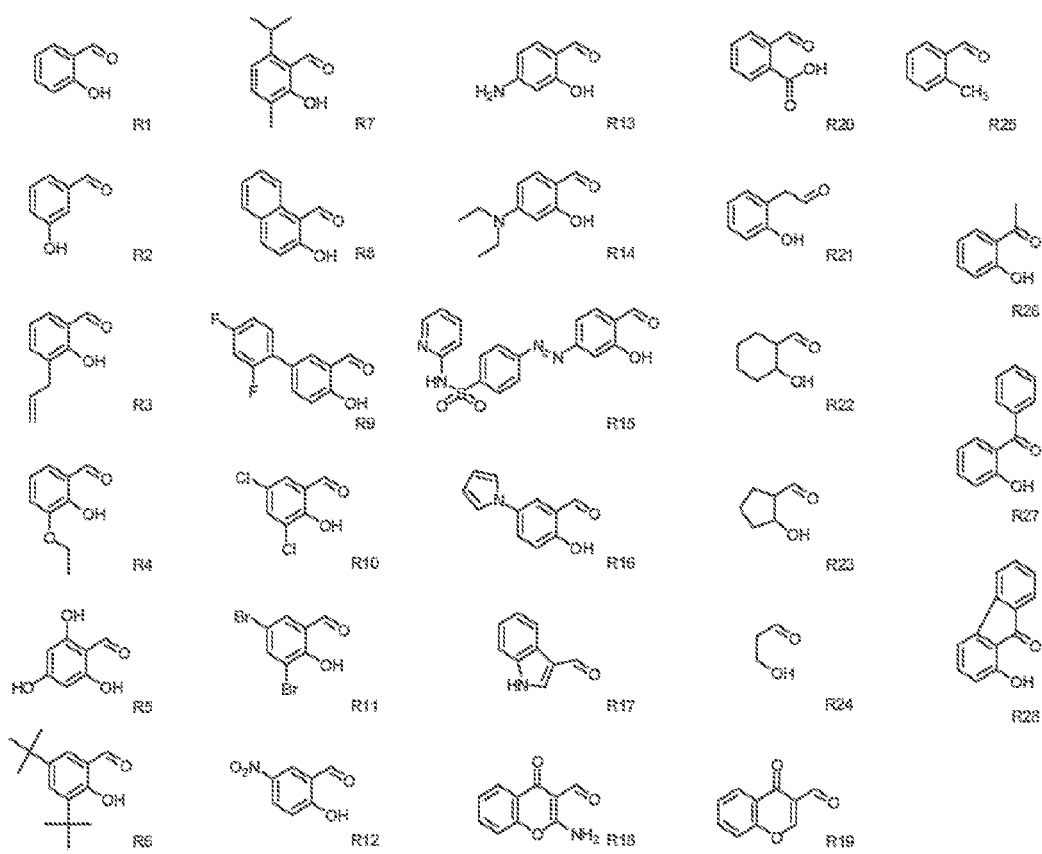

Any one of hydrazide precursor groups (AX) designated L1-L20 are used to generate hydrazides which are reacted with any one of aldehyde groups (BX) designated 1-28, thus yielding 560 PAC-1 derivative compounds. A derivative compound is synthesized using methods as described herein and according to knowledge available in the art. See the scheme and component structures below in addition to FIGS. 8A and 8B.

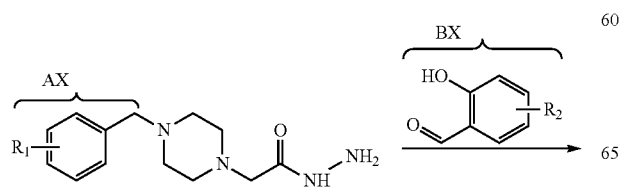

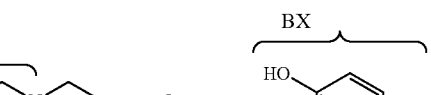

AX

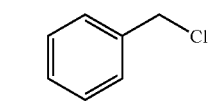
L1

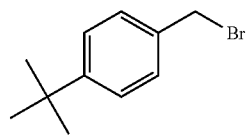
L2

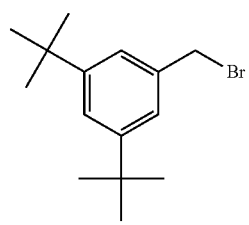
L3

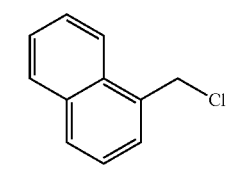
L4

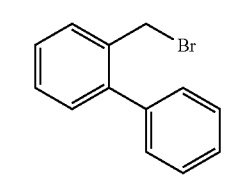
L5

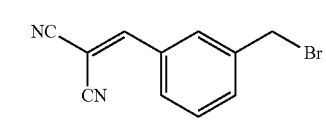
L6

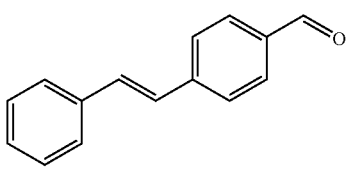
L7

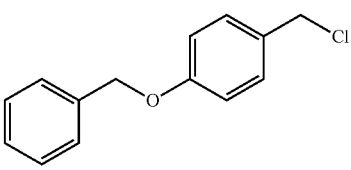
L8

L9 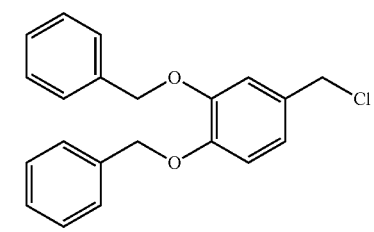
L10 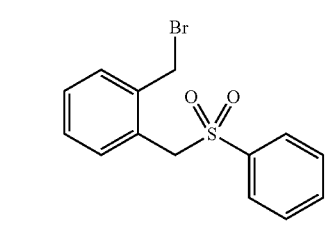
L11 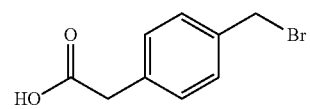
L12 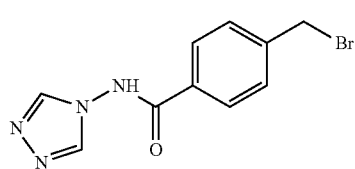
L13 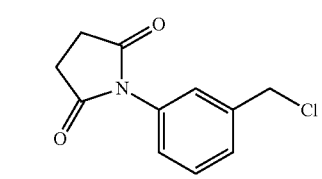
L14 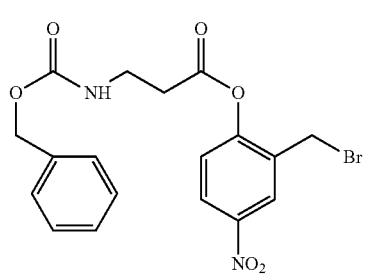
L15 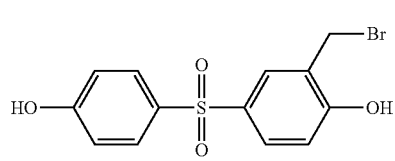
L16 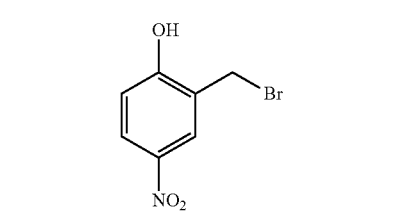
L17 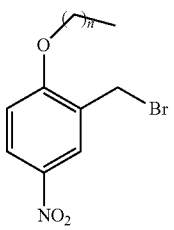
L18 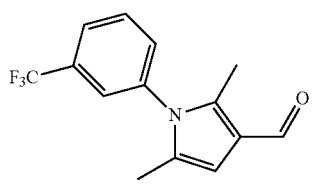
L19 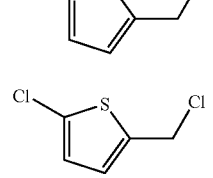
L20 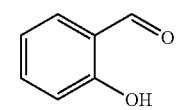
BX
1 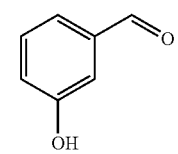
2 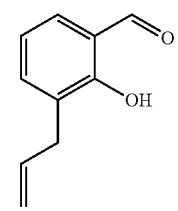
3 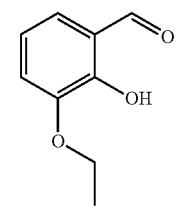
4 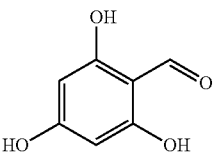
5 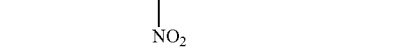

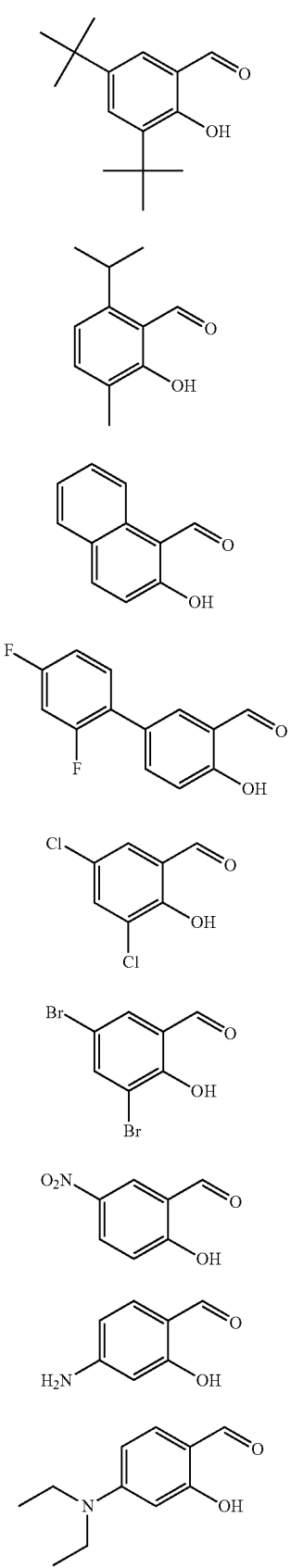
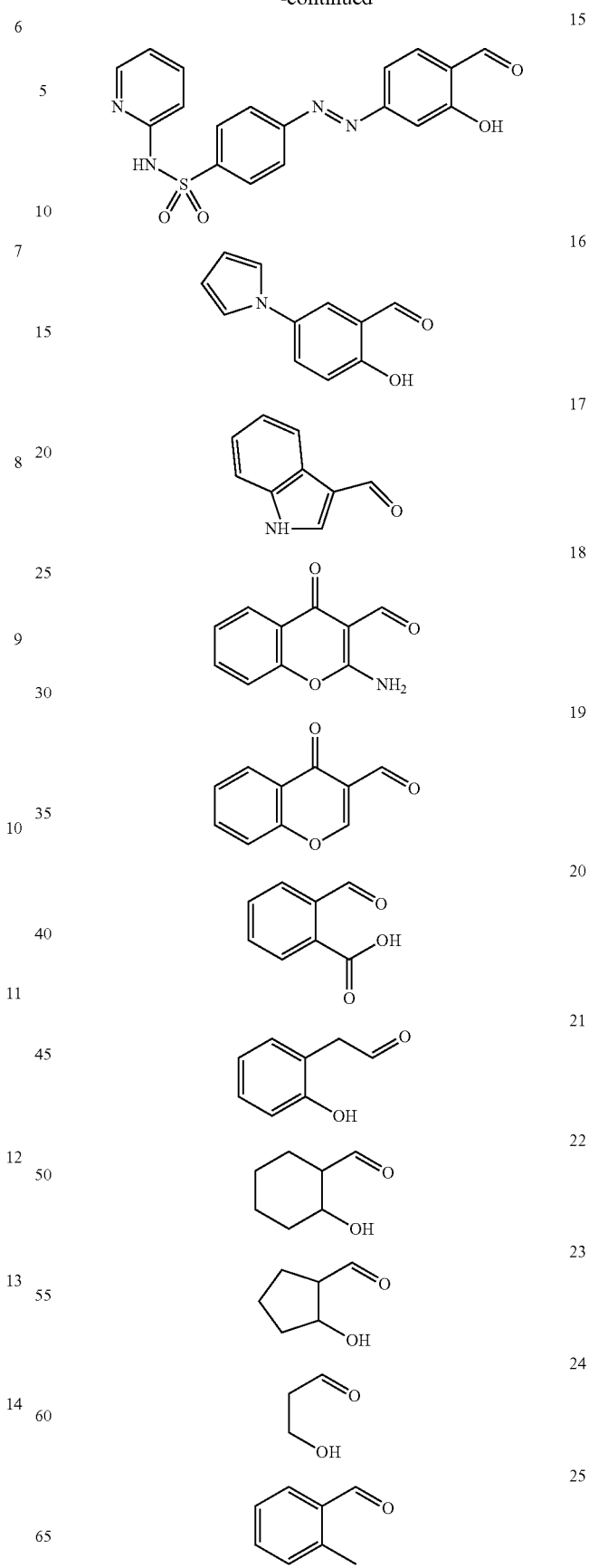

-continued

26 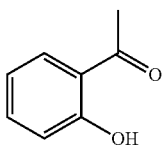

27 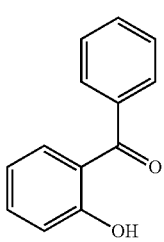

28 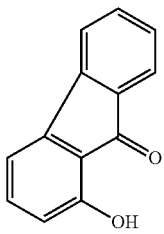

In an embodiment, such derivative compounds are further modified, e.g. to alter a property such as activity, solubility, toxicity, stability, and/or other properties in connection with pharmaceutical applications.

The derivative compounds are used as anti-cancer agents. Compounds are validated as capable of having antineoplastic activity, apoptosis regulation, and/or procaspase-3 activation. For example, primary isolates of freshly removed colon cancer are used to assess procaspase-3 levels and sensitivity of cells to test compound levels, where a test compound is PAC-1 or a derivative compound. Compounds are classified regarding a propensity to induce cell death in cancerous cells versus normal cells.

In further assessing a derivative compound, in vitro and in vivo testing is performed. Stability in connection with exposure to liver microsomes is evaluated.

EXAMPLE 8

Activity of Certain Derivatives Relative to PAC-1

PAC-1 and certain derivatives were tested in the HL-60 cell line and IC50 values were determined. The results are indicated in Table 5 (where L- and R-designations refer to structures shown in the AX and BX series above, respectively). Several of the PAC-1 derivatives exhibited an activity level that was generally about one order of magnitude greater than that of the PAC-1 compound.

TABLE 5

| NAME | STRUCTURE | $IC_{50}$ vs. HL-60 | Fold better than PAC-1 |
|---|---|---|---|
| PAC-1 L01R03 | 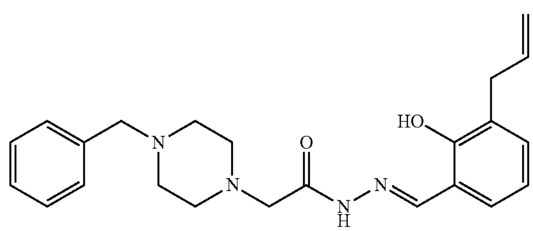 [SMILES: C=CCc1cccc(/C=N/NC(=O)CN2CCN(Cc3ccccc3)CC2)c1O] | 54.6 uM | 1.0 |
| L01R06 | 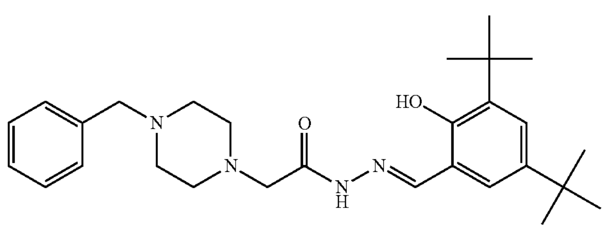 [SMILES: CC(C)(C)c1cc(/C=N/NC(=O)CN2CCN(Cc3ccccc3)CC2)c(O)c(C(C)(C)C)c1] | 5.63 uM | 9.7-fold |
| L02R03 | 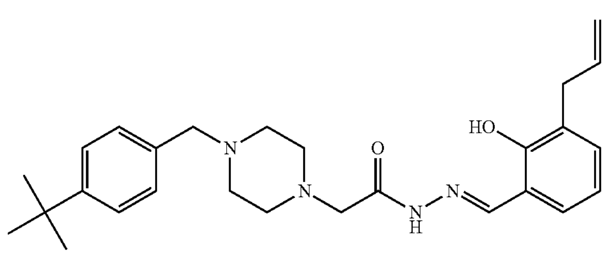 [SMILES: C=CCc1cccc(/C=N/NC(=O)CN2CCN(Cc3ccc(C(C)(C)C)cc3)CC2)c1O] | 4.34 uM | 12.6-fold |

TABLE 5-continued

| NAME | STRUCTURE | IC$_{50}$ vs. HL-60 | Fold better than PAC-1 |
|---|---|---|---|
| L02R06 | 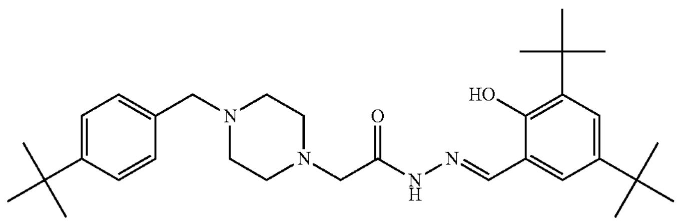 [SMILES: CC(C)(C)c1ccc(CN2CCN(CC(=O)N/N=C/c3cc(C(C)(C)C)cc(C(C)(C)C)c3O)CC2)cc1] | 6.53 uM | 8.4-fold |
| L08R06 | 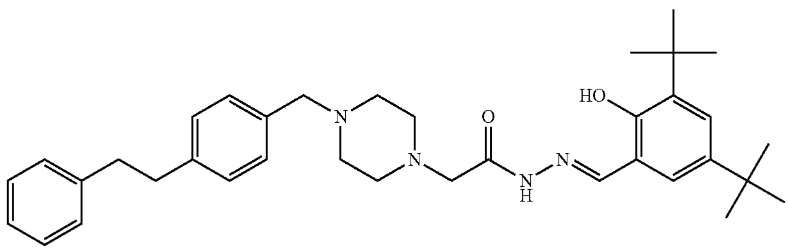 [SMILES: CC(C)(C)c1cc(/C=N/NC(=O)CN2CCN(Cc3ccc(CCc4ccccc4)cc3)CC2)c(O)c(C(C)(C)C)c1] | 5.31 uM | 10.3-fold |
| L09R03 | 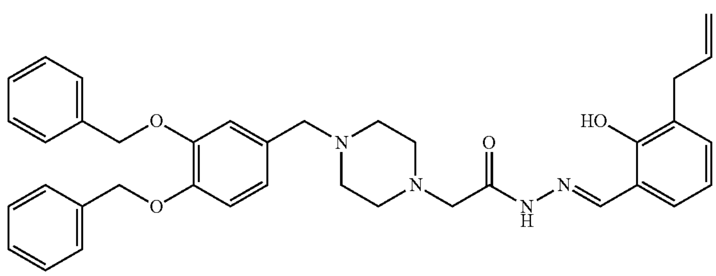 [SMILES: C=CCc1cccc(/C=N/NC(=O)CN2CCN(Cc3ccc(OCc4ccccc4)c(OCc4ccccc4)c3)CC2)c1O] | 4.82 uM | 11.3-fold |
| L09R06 | 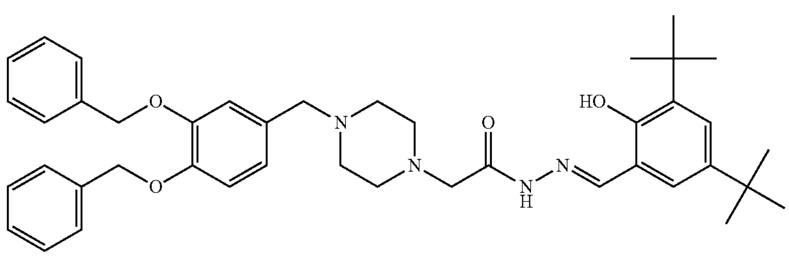 [SMILES: CC(C)(C)c1cc(/C=N/NC(=O)CN2CCN(Cc3ccc(OCc4ccccc4)c(OCc4ccccc4)c3)CC2)c(O)c(C(C)(C)C)c1] | 4.17 uM | 13.1-fold |
| L09R08 | 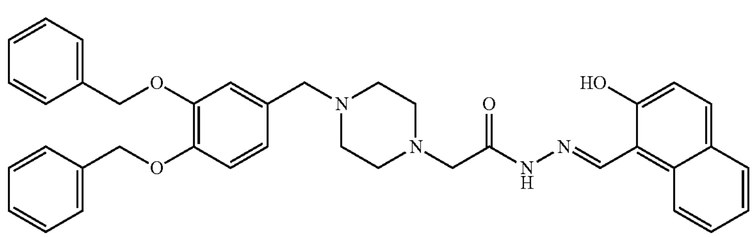 [SMILES: O=C(CN1CCN(Cc2ccc(OCc3ccccc3)c(OCc3ccccc3)c2)CC1)N/N=C/c1c(O)ccc2ccccc12] | 2.42 uM | 22.6-fold |

EXAMPLE 9

Further Compounds and Methods

Figure 11:
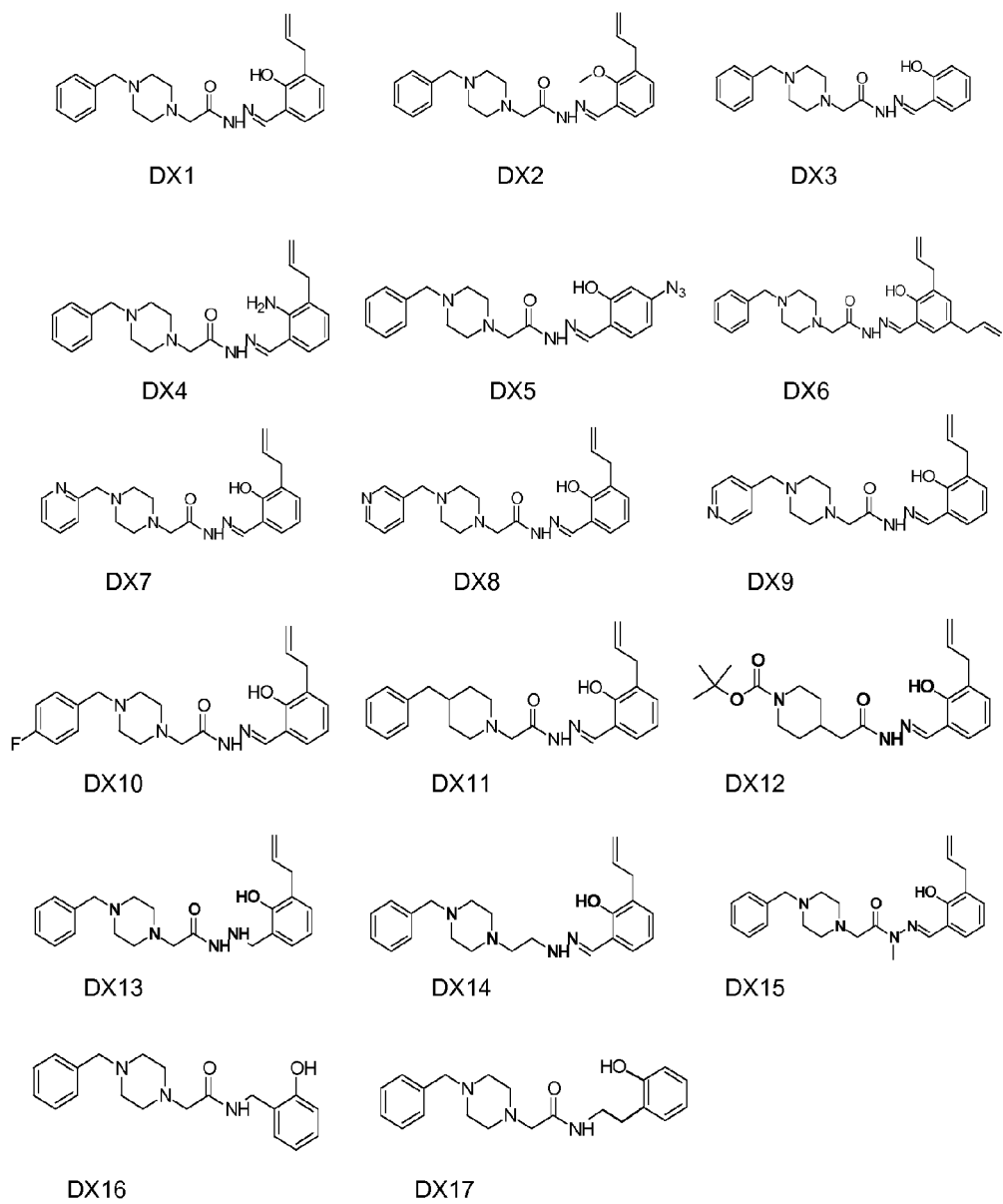
FIG. 11 illustrates structures for compounds designated DX1-DX17 (see, e.g., Examples 9 and 10).

Additional compounds were synthesized and tested for activity. These compounds are designated DX1-17 herein. Structures for these compounds are shown in FIG. 11. It is noted that compound DX1 is PAC-1 and that compound DX3 is de-allyl PAC-1.

Figure 12:
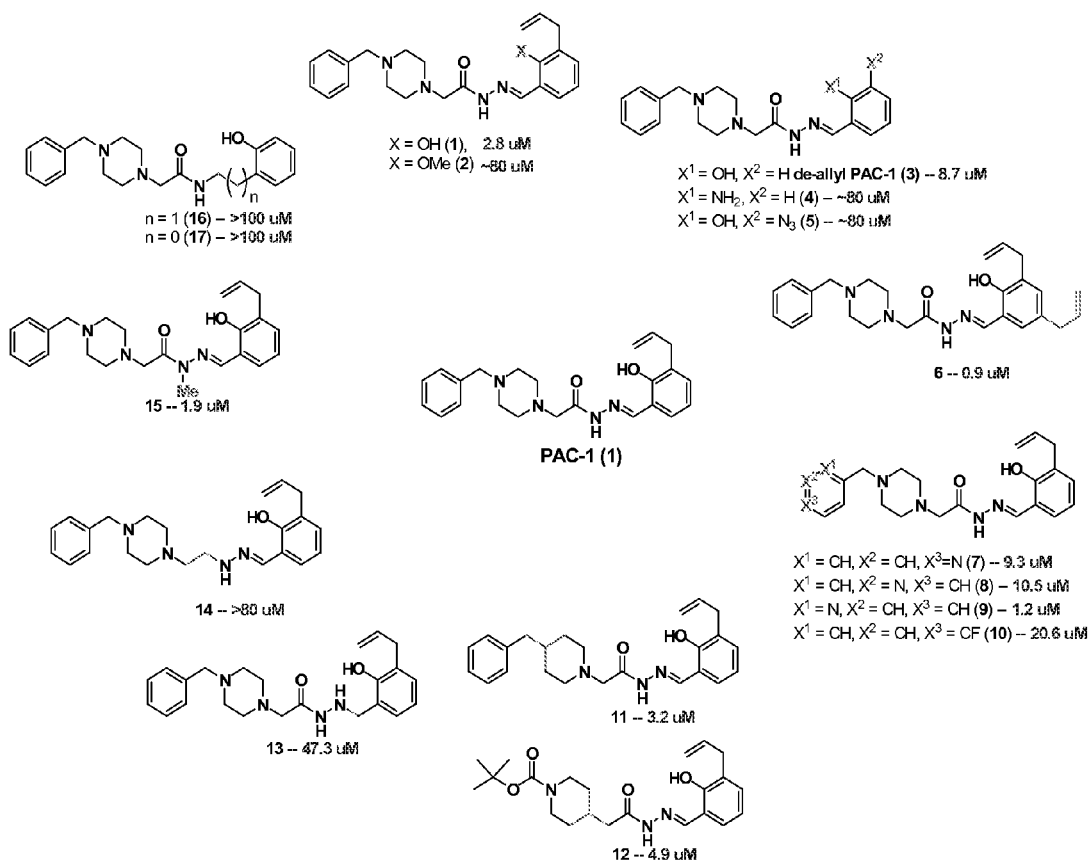
FIG. 12 illustrates activity levels ($IC_{50}$ values) next to structures of compounds DX1-17 from apoptosis induction assays using HL-60 cells.

Compounds DX1-DX17 were tested using the HL-60 cell line for the ability to effect apoptosis, and IC$_{50}$ values were determined. Activity levels of compounds from assays of 72 hrs duration with HL-60 cells are shown in Table 6 and along with structures in FIG. 12.

TABLE 6

Results for compounds DX1-17 in HL-60 cells.

| Compound (DX) | IC$_{50}$ value, micromolar |
|---|---|
| 1 | 2.8 |
| 2 | >80 |

TABLE 6-continued

Results for compounds DX1-17 in HL-60 cells.

| Compound (DX) | IC$_{50}$ value, micromolar |
|---|---|
| 3 | 8.7 |
| 4 | >80 |
| 5 | >80 |
| 6 | 0.9 |
| 7 | 9.3 |
| 8 | 10.5 |
| 9 | 1.2 |
| 10 | 20.6 |
| 11 | 3.2 |
| 12 | 4.9 |
| 13 | 47.3 |
| 14 | >80 |
| 15 | 1.9 |
| 16 | >100 |
| 17 | >100 |

Figure 13:
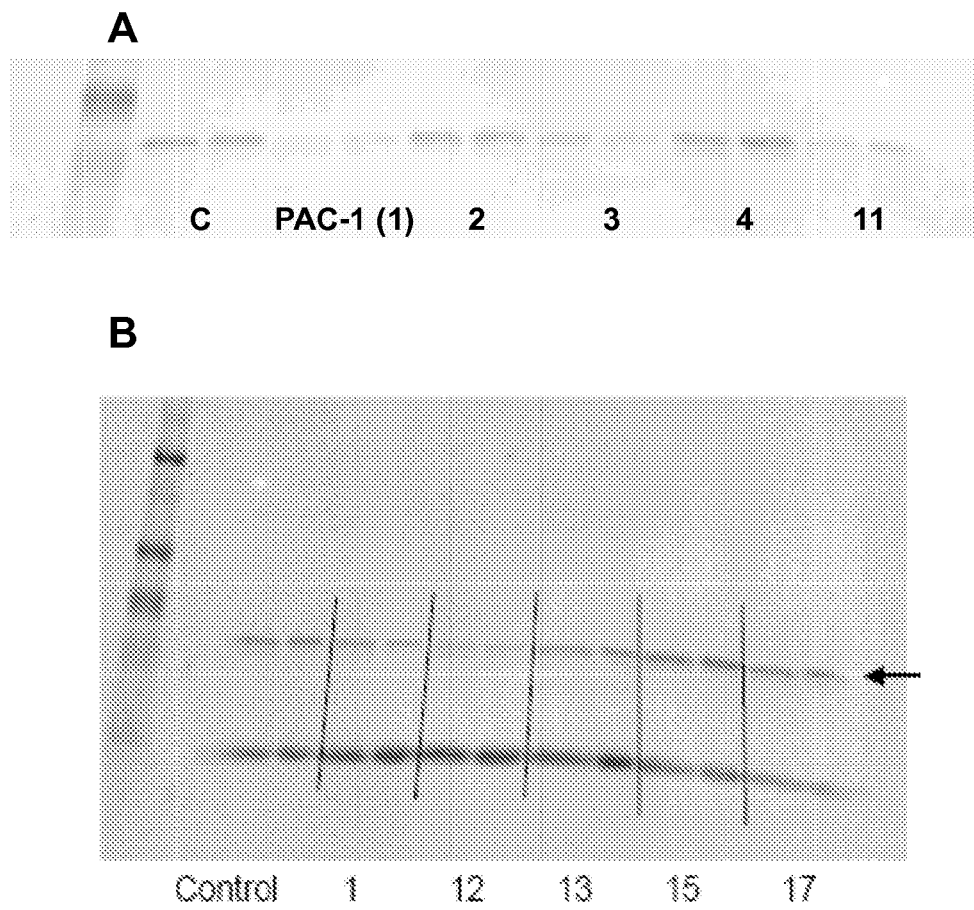
FIG. 13 illustrates results of testing certain compounds for the ability to effect activation of procaspase-3.
Figure 14:
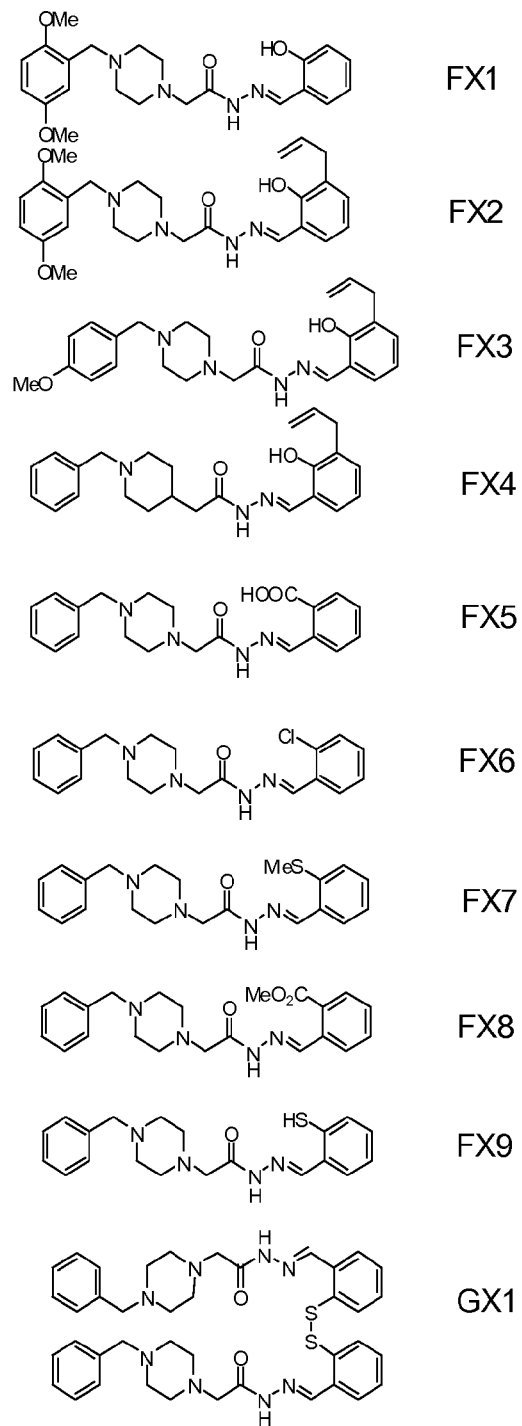
FIG. 14 illustrates the structures of certain compounds including FX1-FX9 and GX1.

Certain compounds were also tested for the ability to effect in vitro activation of procaspase-3. Results of Western blots are shown in FIG. 13. FIG. 13A indicates substantial activity levels for compounds PAC-1 (alias DX1), DX3, and DX11 relative to the control levels (for lanes indicated with letter "C"). FIG. 13B also illustrates results of testing for activity of compounds DX1, DX12, DX13, DX15, and DX17; the arrow indicates the location of procaspase-3. Experimental conditions included compound concentrations of 50 micromolar, procaspase-3 levels of about 35 nanomolar, and treatment periods of 8 hr.

In an embodiment, a DX compound herein is capable of inducing or selectively inducing apoptosis in a cancer cell. In an embodiment, a compound is used as an anti-cancer drug. In an embodiment, a compound is used as a pro-apoptotic agent. In an embodiment, a preferred DX compound is DX6, DX7, DX8, DX9, DX10, DX11, DX12, or DX15.

EXAMPLE 10

Synthetic Schemes for Certain Compounds and Methods

Schemes for synthesis of compounds including DX1-DX17 are shown herein.

Scheme for DX1

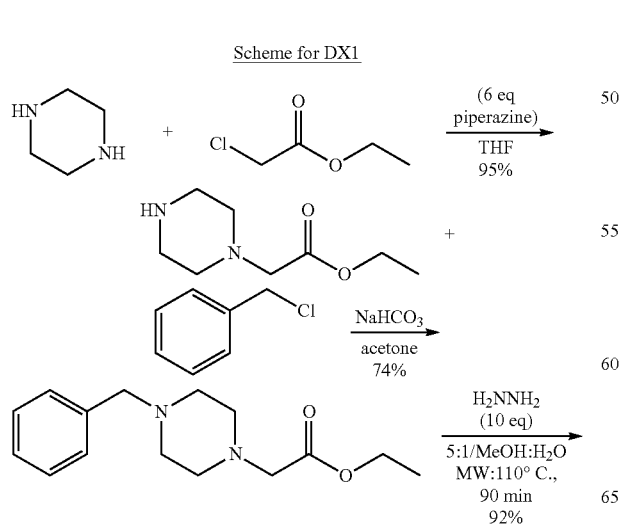

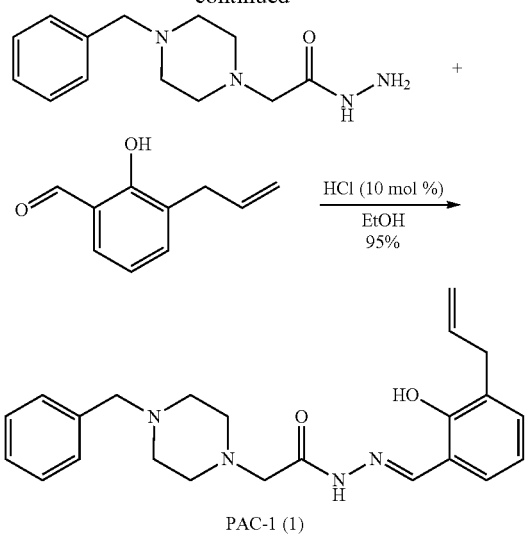

PAC-1 (1)

Scheme for DX2

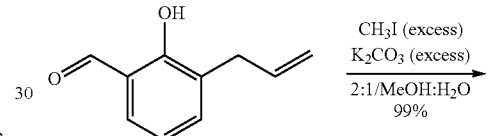

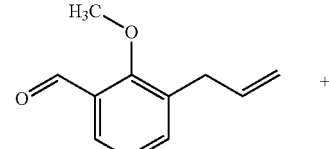

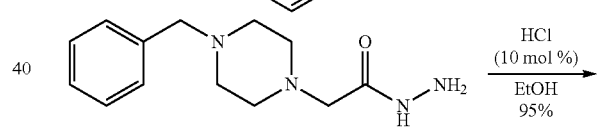

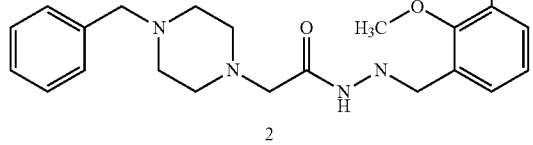

2

Scheme for DX3

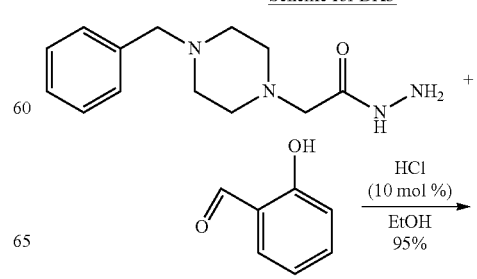

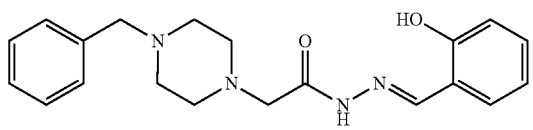
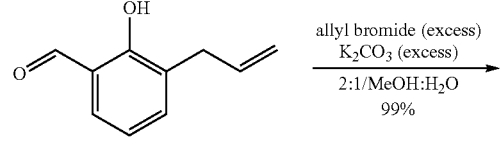
Scheme for DX6
Scheme for DX4
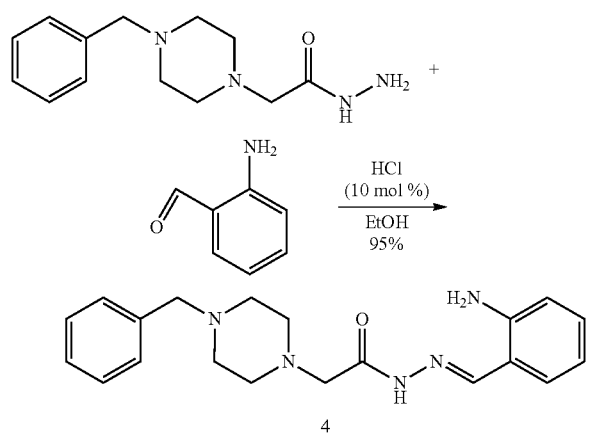
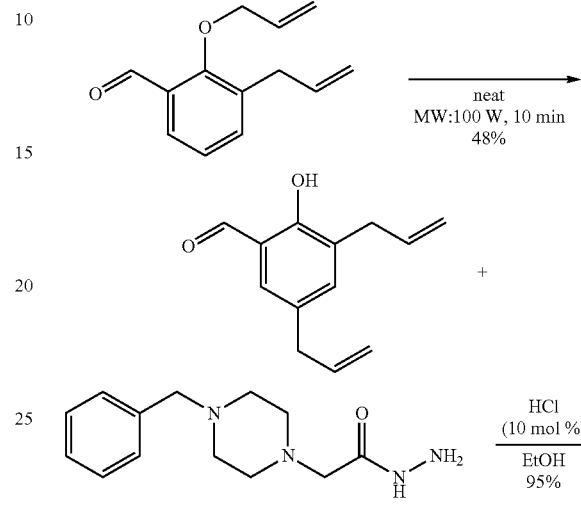
Scheme for DX5
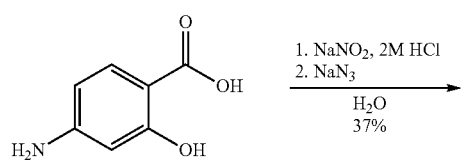
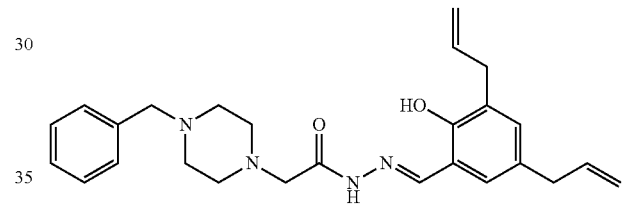
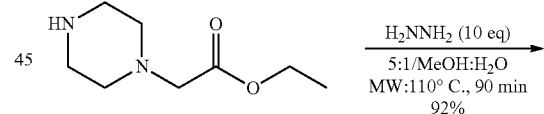
Scheme for DX7
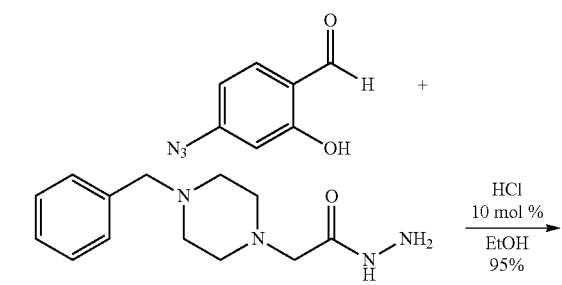
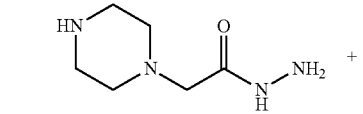
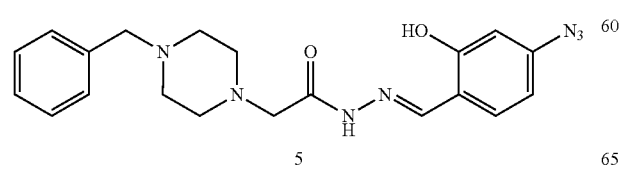
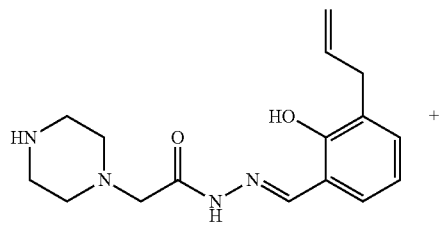

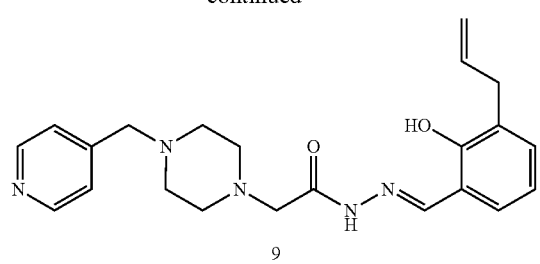
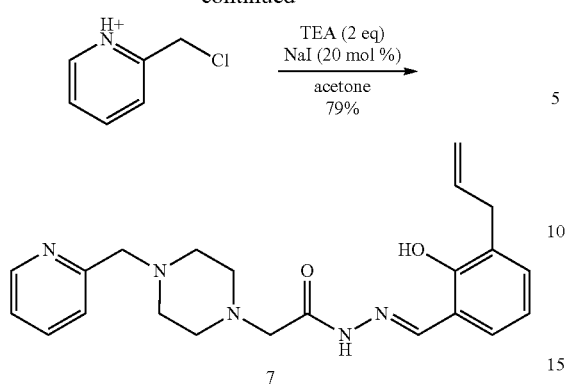
Scheme for DX8
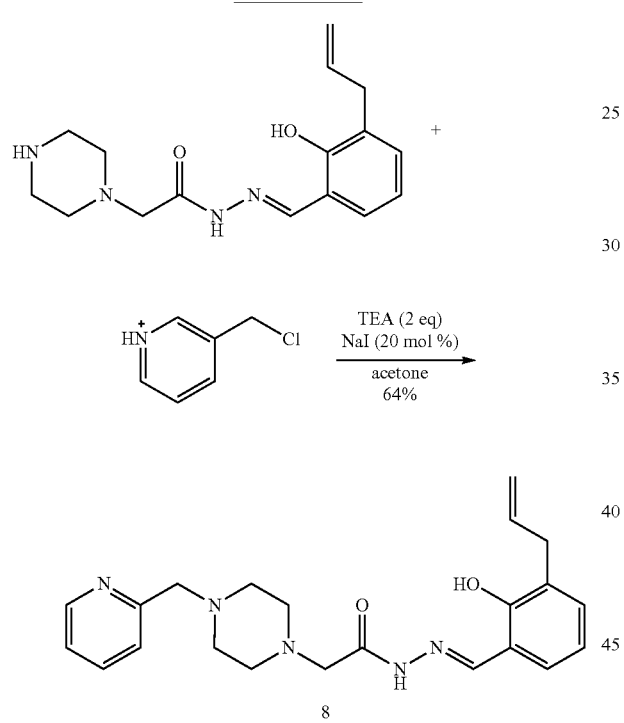
Scheme for DX9
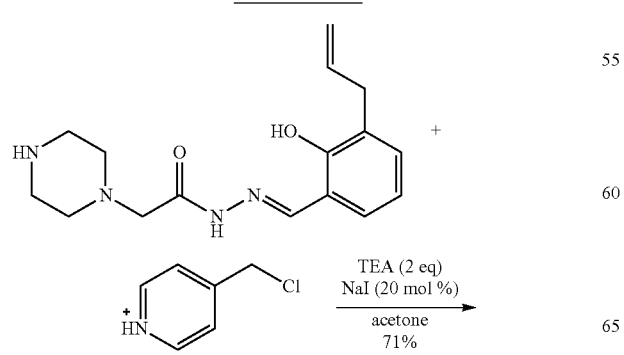
Scheme for DX10
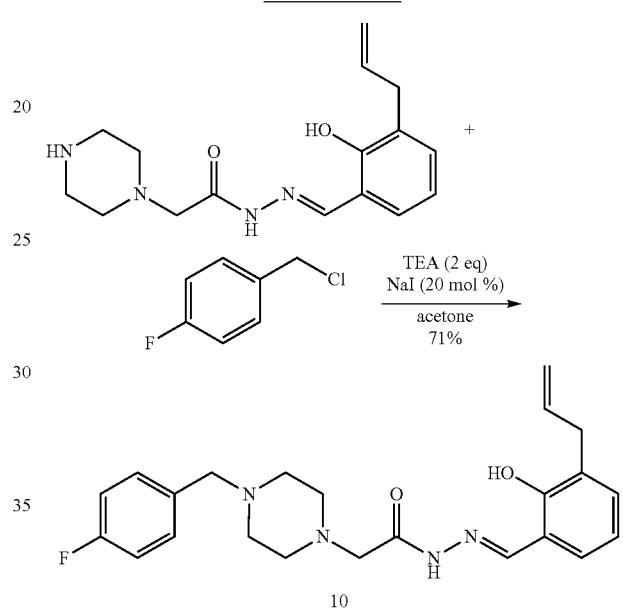
Scheme for DX11
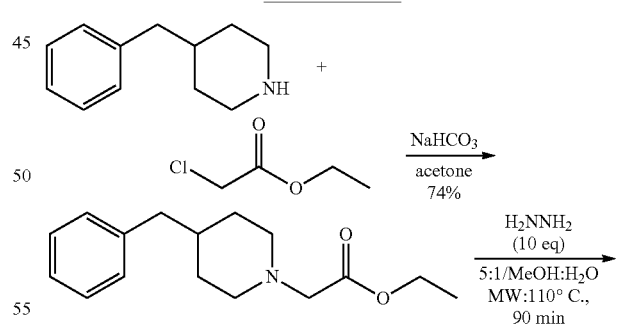
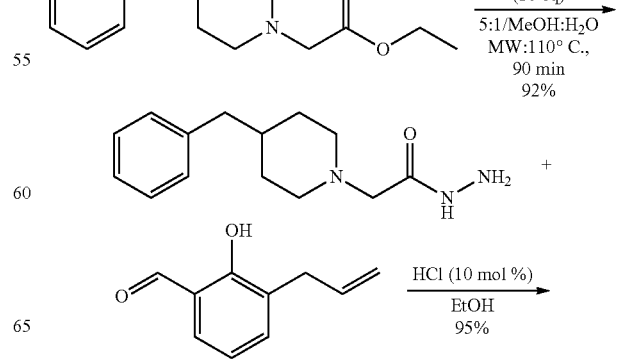

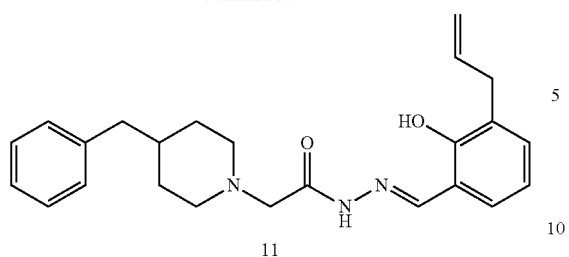
11
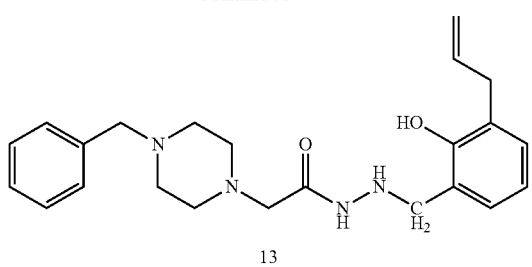
13
Scheme for DX12
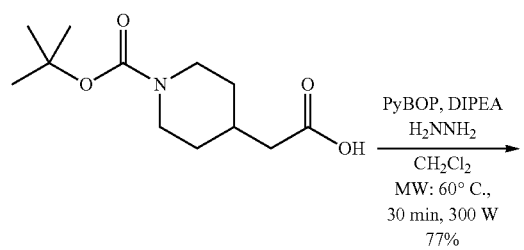
Scheme for DX14
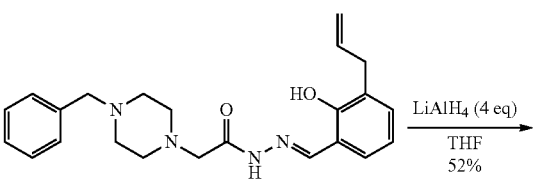
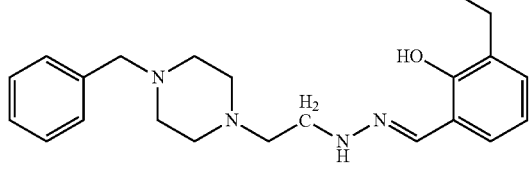
14
12
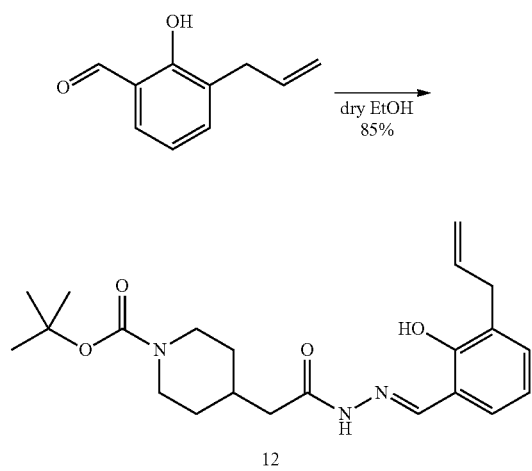
Scheme for DX15
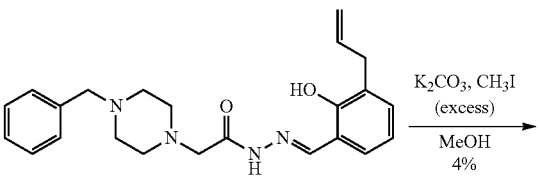
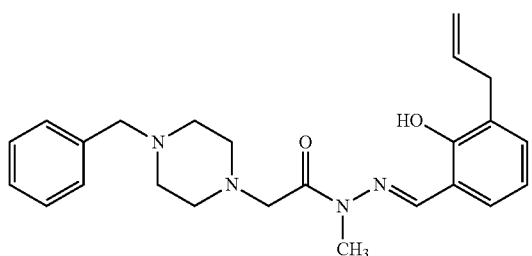
15
Scheme for DX13
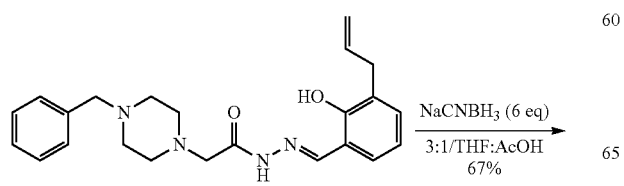

Scheme for DX16
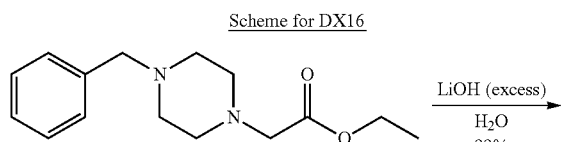
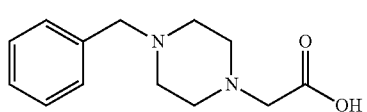
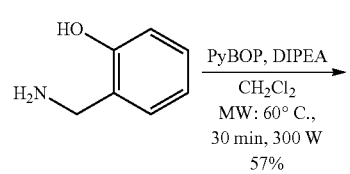
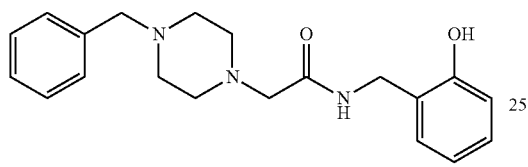
16
Scheme for DX17
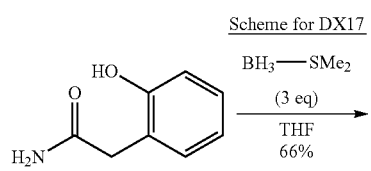
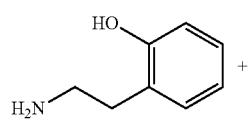
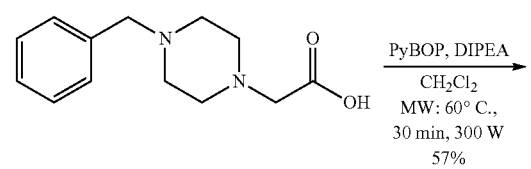
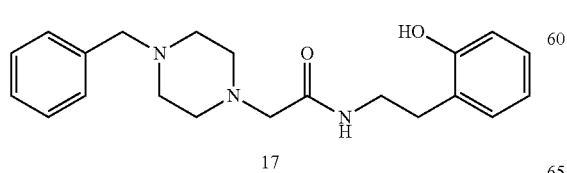
17
EXAMPLE 11
Synthetic Schemes for Certain Compounds and Methods
Schemes for synthesis of further compounds including FX1-FX9 and GX1 are shown herein.
Scheme for FX1:
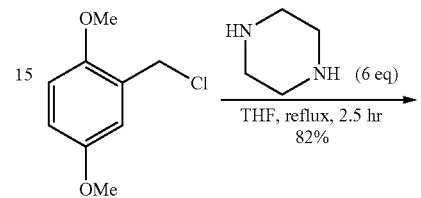
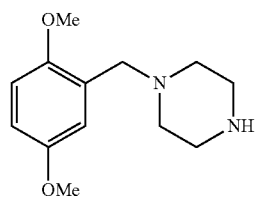
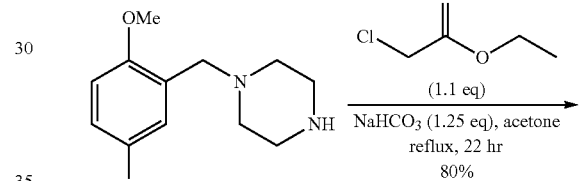
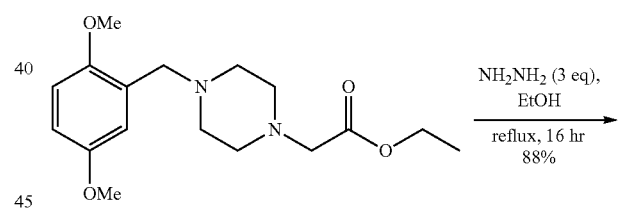
100
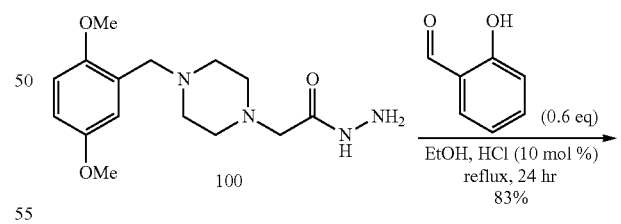
FX1

Scheme for FX2:
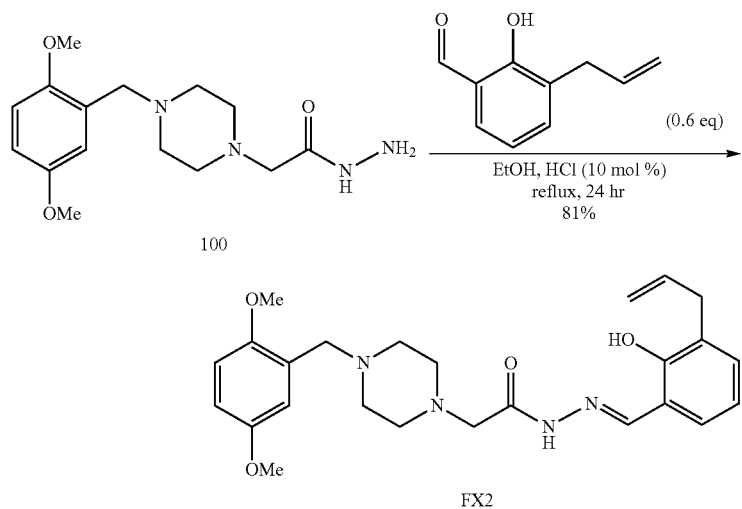
Scheme for FX3:
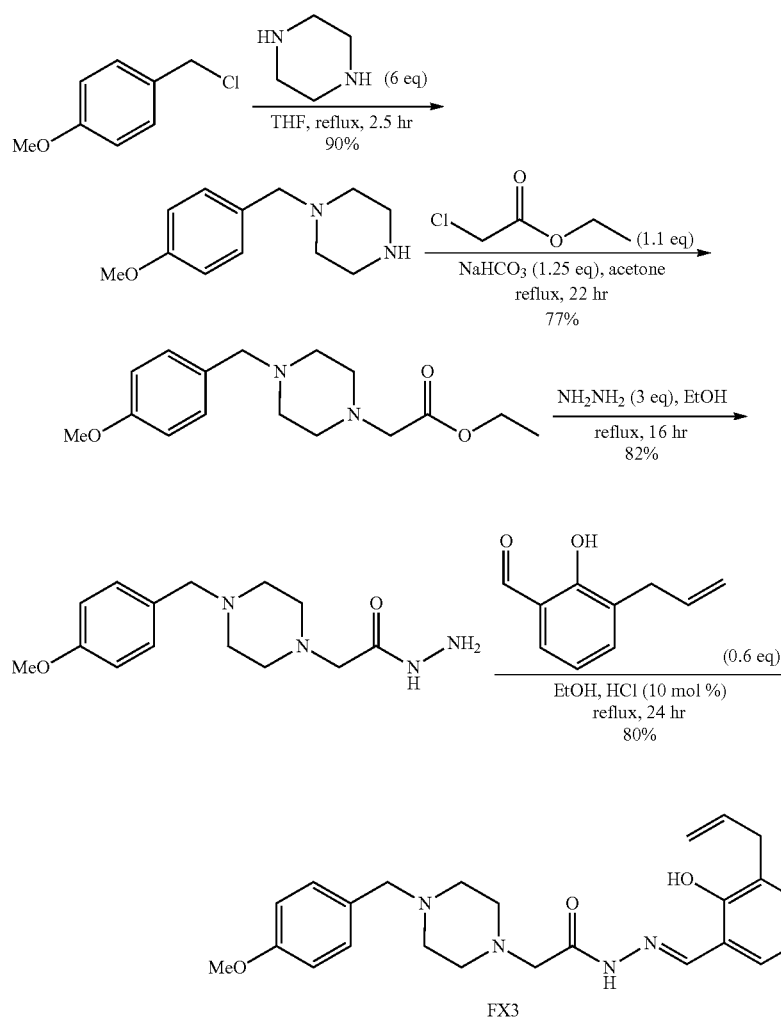

Scheme for FX4:
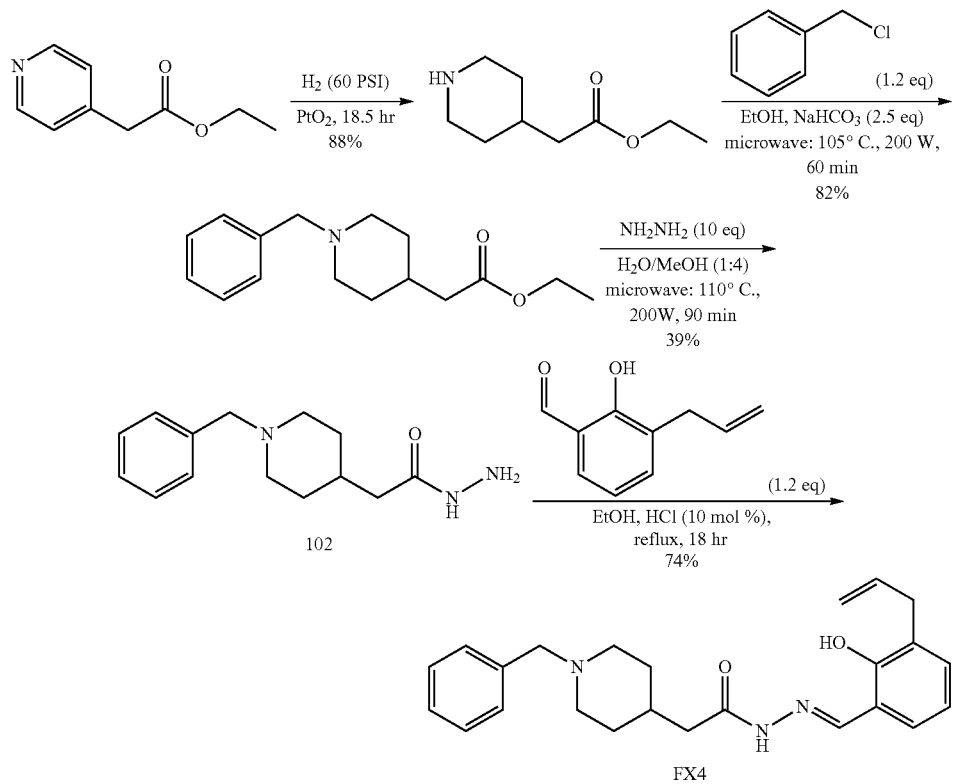
Scheme for FX5:
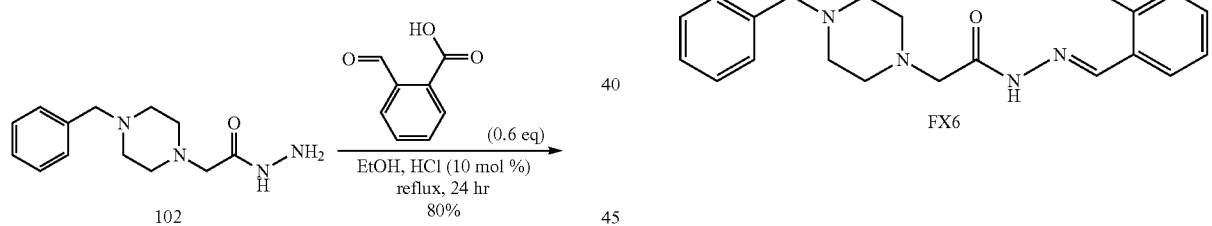
Scheme for FX6:
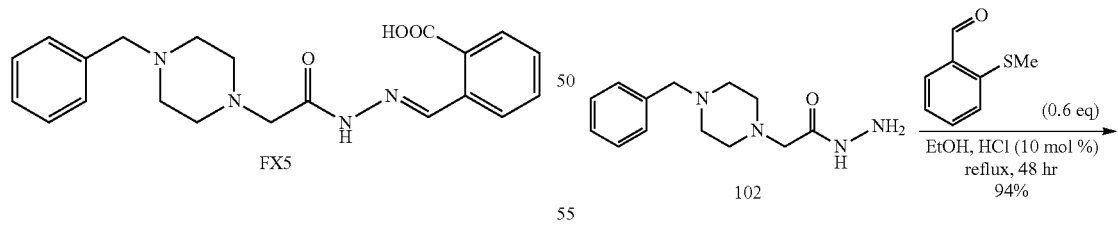
-continued
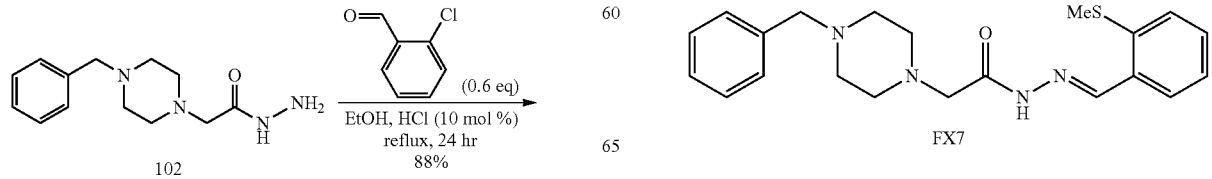
Scheme for FX7:

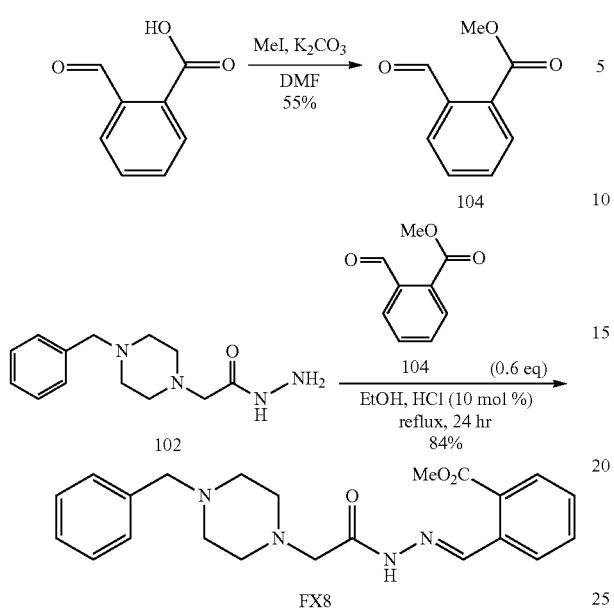

Scheme for FX8:

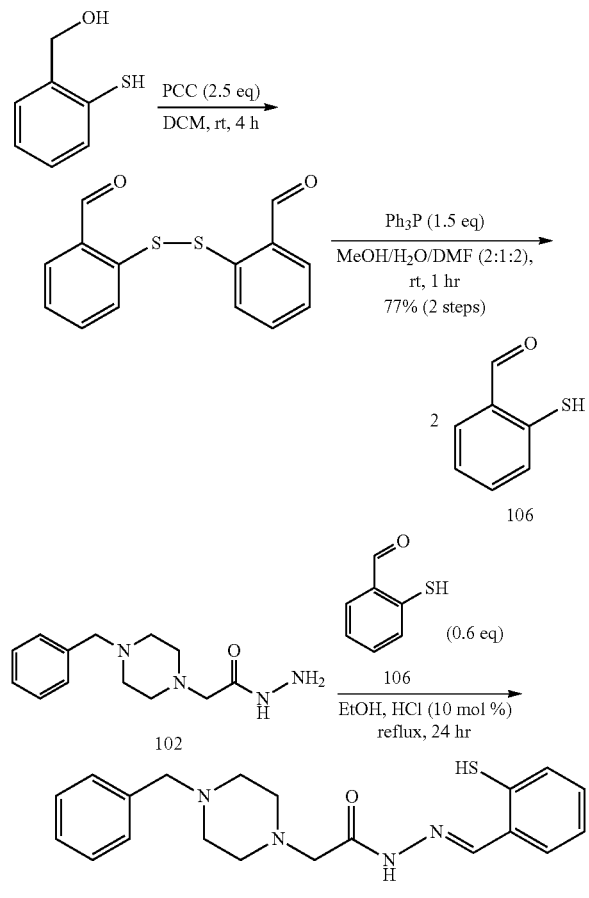

Scheme for FX9 and GX1:

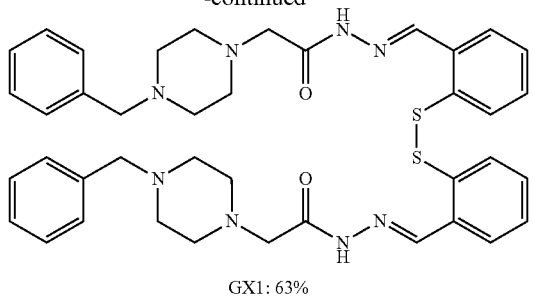

GX1: 63%

EXAMPLE 12

Activity of Certain Compounds

Figure 15:
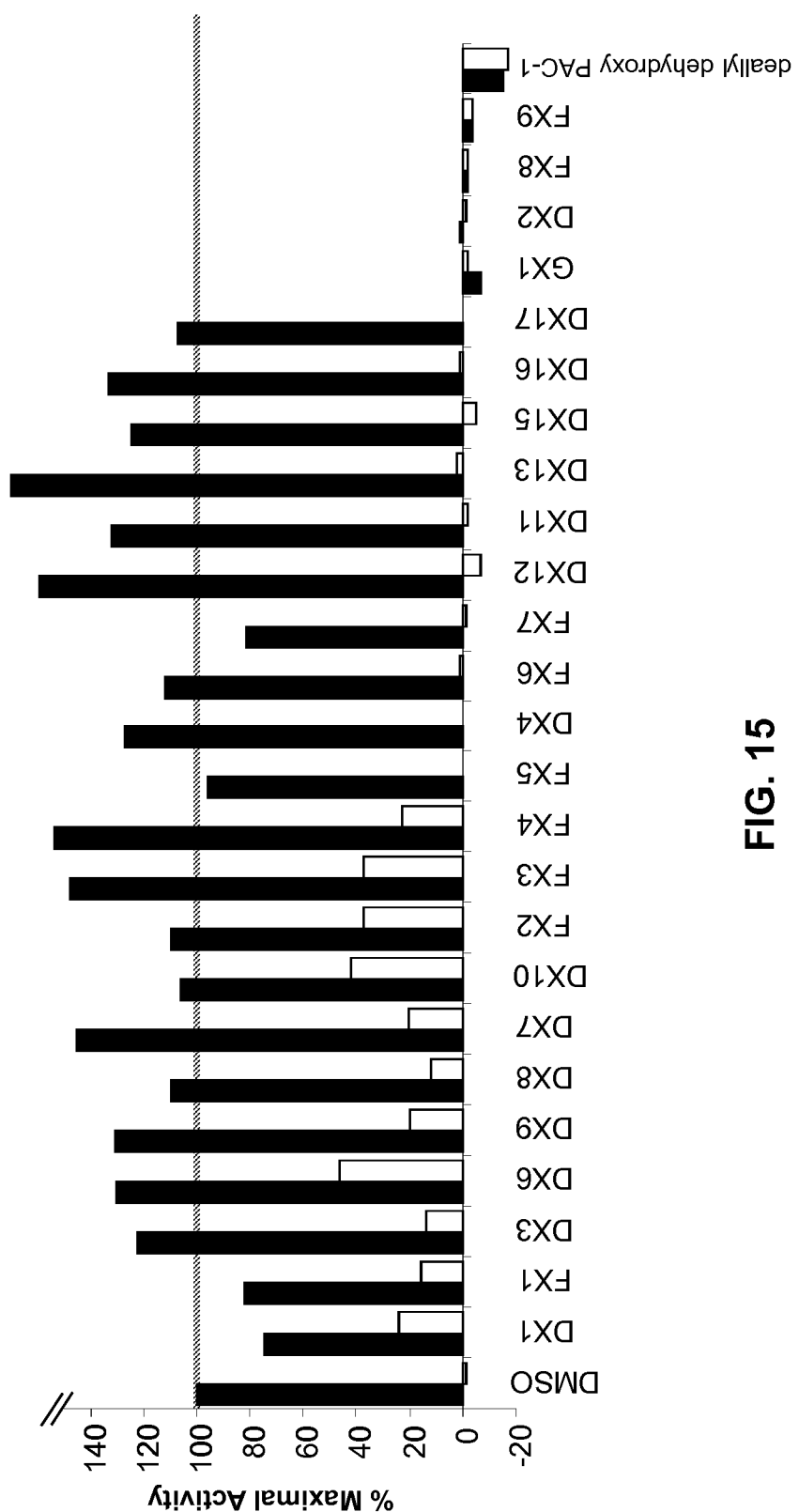
FIG. 15 illustrates results from activity testing of compounds including such in the series DX, FX, and GX. Test conditions used 2.5 μM procaspase-3 ($D_3A$) with the indicated test compound at 100 μM (filled columns); and further with 10 μM zinc (open columns).
Figure 16:
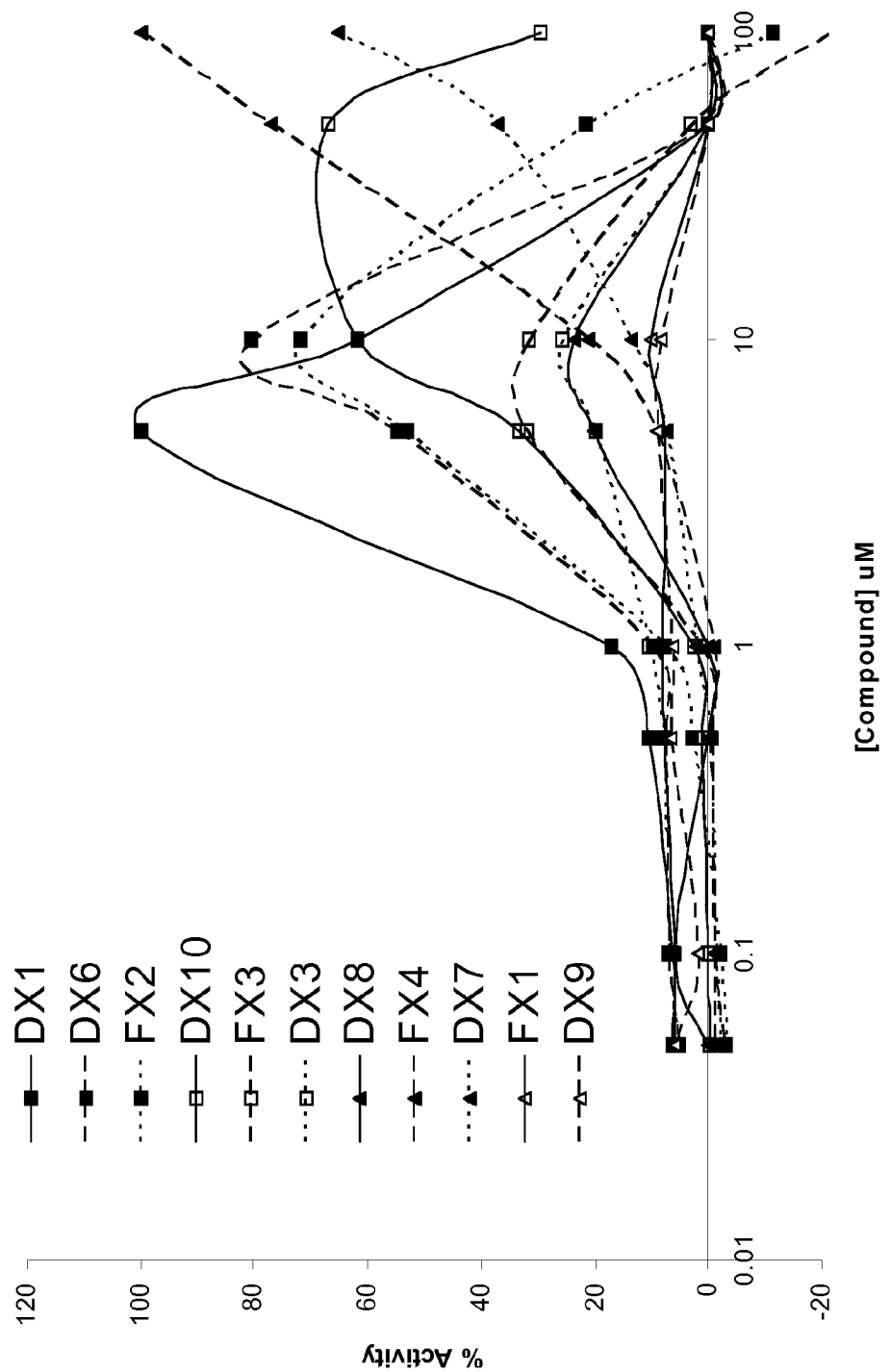
FIG. 16 illustrates results from activity testing of compounds in the series DX and FX, plotted as percent activity versus compound concentration.

Certain compounds were tested for activity. Results are indicated in FIGS. 15 and 16. FIG. 15 illustrates results from activity testing of compounds including such in the series DX, FX, and GX. Test conditions used 2.5 µM procaspase-3 ($D_3A$) with the indicated test compound at 100 µM (filled columns); and further with 10 µM zinc (open columns). FIG. 16 illustrates results from activity testing of compounds in the series DX and FX, plotted as percent activity versus compound concentration.

Assay description—Materials and methods. Compounds were tested in an in vitro activity assay. In this assay, an "uncleavable" or cleavage-resistant form of procaspase-3 was used. In this protein, the cleavage sites have been mutated from aspartic acid residues to alanine residues (D3A). This form of procaspase-3 generally cannot be cleaved through autoactivation or by another protease. As such, the activity of the compounds on the zymogen can be monitored independent of proteolytic processing. In these experiments, 2.5 µM Procaspase-3 (D3A) was incubated for 1 hour in the presence and absence of 10 µM zinc and the presence and absence of compounds. The ability of the compounds to activate procaspase-3 (D3A) was monitored by the use of 100 µM Ac-DEVD-pNA substrate, and the absorbance was monitored at 405 nm. An amount of 10 µM zinc is sufficient to fully inhibit 2.5 µM Procaspase-3 (D3A). This experiment revealed four classes of compounds: Activators, Inhibitors, Dual mode, and Non-effectors. Compounds that were capable of relieving the inhibitory affect of zinc are considered activators. Compounds that inhibit procaspase-3 (D3A) activity even in the absence of zinc are considered inhibitors. Some compounds exhibit the characteristics of both an activator and an inhibitor, and some compounds had no effect in this assay.

Compounds that were activators or had dual activity were further tested in a dose response experiment. In this experiment, 2.5 µM Procaspase-3 (D3A) was incubated with 10 µM zinc and various concentrations of each compound. After incubation for 1 hour, 200 µM Ac-DEVD-pNA was added to each sample and the absorbance was monitored at 405 nm. In this experiment we find that the compounds are able to activate procaspase-3 in the presence of zinc to varying degrees. Additionally, some of these compounds show inhibition at higher concentrations.

Statements Regarding Incorporation By Reference And Variations

All references throughout this application, for example patent documents including issued or granted patents or equivalents; patent application publications; unpublished patent applications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the invention are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive. For clarification, as used herein "comprising" is synonymous with "having," "including," "containing," or "characterized by," and is inclusive or open-ended and does not exclude additional, unrecited elements or method steps. As used herein, "consisting of" excludes any element, step, component, or ingredient not specified in the claim element. As used herein, "consisting essentially of" does not exclude materials or steps that do not materially affect the basic and novel characteristics of the claim (e.g., not affecting an active ingredient). In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

The invention has been described with reference to various specific and preferred embodiments and techniques. However, it should be understood that many variations and modifications may be made while remaining within the spirit and scope of the invention. It will be appreciated by one of ordinary skill in the art that compositions, methods, devices, device elements, materials, optional features, procedures and techniques other than those specifically described herein can be applied to the practice of the invention as broadly disclosed herein without resort to undue experimentation. All art-known functional equivalents of compositions, methods, devices, device elements, materials, procedures and techniques described herein; and portions thereof; are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation. The scope of the invention shall be limited only by the claims.

References

These applications are particularly incorporated by reference in entirety: U.S. Provisional Patent Application No. 60/516,556 by Hergenrother et al., filed Oct. 30, 2003; U.S. Provisional Patent Application No. 60/603,246 by Hergenrother et al., filed Aug. 20, 2004; U.S. Ser. No. 10/976,186 by Hergenrother et al., filed Oct. 27, 2004.

U.S. Provisional Application Ser. 60/684,807 filed May 26, 2005; U.S. Provisional Application Ser. 60/743,878 filed Mar. 28, 2006; U.S. patent application Ser. No. 11/420,425 filed May 25, 2006; PCT International Application Serial PCT/US 06/020910 filed May 26, 2006; U.S. Provisional Application Ser. 60/914,592 filed Apr. 27, 2007.

U.S. Pat. No. 6,762,045 Membrane derived caspase-3, compositions comprising the same and methods of use therefore; U.S. Pat. No. 6,534,267 Polynucleotides encoding activators of caspases; U.S. Pat. No. 6,403,765 Truncated Apaf-1 and methods of use thereof; U.S. Pat. Nos. 6,303,329; 6,878,743 by Choong, et al. issued Apr. 12, 2005; US 20040077542 by Wang, Xiaodong; et al., published Apr. 22, 2004; US 20040180828 by Shi, Yigong, published Sep. 16, 2004.

Slee E A et al., Benzyloxycarbonyl-Val-Ala-Asp (OMe) fluoromethylketone (Z-VAD.FMK) inhibits apoptosis by blocking the processing of CPP32, Biochem J. 1996 Apr. 1; 315 (Pt 1):21-4.

1. Hanahan, D. & Weinberg, R. A. The hallmarks of cancer. Cell 100, 57-70 (2000).

2. Okada, H. & Mak, T. W. Pathways of apoptotic and non-apoptotic death in tumour cells. Nature Rev. Cancer 4, 592-603 (2004).

3. Roy, S. et al. Maintenance of caspase-3 proenzyme dormancy by an intrinsic "safety catch" regulatory tripeptide. Proc. Natl. Acad. Sci. 98, 6132-6137 (2001).

4. Svingen, P. A. et al. Components of the cell death machine and drug sensitivity of the National Cancer Institute Cell Line Panel. Clin. Cancer Res. 10, 6807-6820 (2004).

5. Lowe, S. W., Cepero, E. & Evan, G. Intrinsic tumor suppression. Nature 432, 307-315 (2004).

6. Vogelstein, B. & Kinzler, K. W. Achilles' heel of cancer. Nature 412, 865-866 (2001).

7. Traven, A., Huang, D. C. & Lithgow, T. Protein hijacking: key proteins held captive against their will. Cancer Cell 5, 107-108 (2004).

8. Soengas, M. S. et al. Inactivation of the apoptosis effector Apaf-1 in malignant melanoma. Nature 409, 207-211 (2001).

9. Wajant, H. Targeting the FLICE inhibitory protein (FLIP) in cancer therapy. Mol. Interv. 3, 124-127 (2003).

10. Denicourt, C. & Dowdy, S. F. Targeting apoptotic pathways in cancer cells. Science 305, 1411-1413 (2004).

11. Vassilev, L. T. et al. In vivo activation of the p53 pathway by small-molecule antagonists of MDM2. Science 303, 844-848 (2004).

12. Degterev, A. et al. Identification of small-molecule inhibitors of interaction between the BH3 domain and Bcl-XL. Nature Cell Biol. 3, 173-182 (2001).

13. Becattini, B. et al. Rational design and real time, in-cell detection of the proapoptotic activity of a novel compound targeting Bcl-XL. Chem. Biol. 11, 389-395 (2004).

14. Wang, J.-L. et al. Structure-based discovery of an organic compound that binds Bcl-2 protein and induces apoptosis of tumor cells. Proc. Natl. Acad. Sci. 97, 7124-7129 (2000).

15. Li, L. et al. A small molecule Smac mimic potentiates TRAIL- and TNFa-mediated cell death. Science 305, 1471-1474 (2004).

16. Nguyen, J. T. & Wells, J. A. Direct activation of the apoptosis machinery as a mechanism to target cancer cells. Proc. Natl. Acad. Sci. U.S.A. 100, 7533-7538 (2003).

17. Jiang, X. et al. Distincitive roles of PHAP proteins and prothymosin-α in a death regulatory pathway. Science 299, 223-226 (2003).

18. Boatright, K. M. & Salvesen, G. S. Mechanisms of caspase activation. Curr. Opin. Cell. Biol. 15, 725-731 (2003).

19. Nakagawara, A. et al. High levels of expression and nuclear localization of interleukin-1 β converting enzyme (ICE) and CPP32 in favorable human neuroblastomas. Cancer Res. 57, 4578-4584 (1997).

20. Izban, K. F. et al. Characterization of the interleukin-1β-converting enzyme/Ced-3-family protease, caspase-3/CPP32, in Hodgkin's disease. Am. J. Pathol. 154, 1439-1447 (1999).

21. Persad, R. et al. Overexpression of caspase-3 in hepatocellular carcinomas. Modern Pathol. 17, 861-867 (2004).

22. Pop, C., Feeney, B., Tripathy, A. & Clark, A. C. Mutations in the procaspase-3 dimer interface affect the activity of the zymogen. Biochemistry 42, 12311-12320 (2003).

23. Stennicke, H. R. et al. J. Biol. Chem. 273, 27084-27090 (1998).

24. Denault, J.-B. & Salvesen, G. S. Human caspase-7 activity and regulation by its N-terminal peptide. J. Biol. Chem. 278, 34042-24050 (2003).

25. Putt, K. S., Beilman, G. J. & Hergenrother, P. J. Direct quantitation of Poly(ADP-ribose) polymerase (PARP) activity as a means to distinguish necrotic and apoptotic death in cell and tissue samples. ChemBioChem 6, 53-55 (2005).

26. Liang, Y., Nylander, K. D., Yan, C. & Schor, N. F. Role of caspase 3-dependent Bcl-2 cleavage in potentiation of apoptosis by Bcl-2. Mol. Pharmacol. 61, 142-149 (2002).

27. Fujita, N., Nagahshi, A., Nagashima, K., Rokudai, S. & Tsuruo, T. Acceleration of apoptotic cell death after the cleavage of Bcl-XL protein by caspase-3-like proteases. Oncogene 17, 1295-1304 (1998).

28. Earnshaw, W. C., Martins, L. M. & Kaufmann, S. H. Mammalian caspases: structure, activation, substrates, and functions during apoptosis. Annu. Rev. Biochem. 68, 383-424 (1999).

29. Koty, P. P., Zhang, H. & Levitt, M. L. Antisense bcl-2 treatment increases programmed cell death in non-small cell lung cancer cell lines. Lung Cancer 23, 115-127 (1999).

National Center for Biotechnology Information (NCBI) Database of the National Library of Medicine/National Institutes of Health (NIH) website: http://www.ncbi.nlm.nih.gov/ using the Gene database to search for CASP3 (caspase 3, apoptosis-related cysteine protease [*Homo sapiens*] GeneID: 836 Locus tag: HGNC:1504; MIM: 600636 updated 15 May 2005. Other Aliases: HGNC:1504, APOPAIN, CPP32, CPP32B, SCA-1; Other Designations: Human procaspase3 coding sequence; PARP cleavage protease; SREBP cleavage activity 1; Yama; caspase 3; cysteine protease CPP32).

Hergenrother P J. Obtaining and screening compound collections: a user's guide and a call to chemists. Curr Opin Chem Biol. 2006

Silverman S K, Hergenrother P J. Combinatorial chemistry and molecular diversity Tools for molecular diversification and their applications in chemical biology. Curr Opin Chem Biol. 2006.

Goode D R, Sharma A K, Hergenrother P J. Using peptidic inhibitors to systematically probe the S1' site of caspase-3 and caspase-7. Org Lett. 2005 Aug. 4; 7(16):3529-32. PMID: 16048334

Dothager R S, Putt K S, Allen B J, Leslie B J, Nesterenko V, Hergenrother P J. Synthesis and identification of small molecules that potently induce apoptosis in melanoma cells through G1 cell cycle arrest. J Am Chem Soc. 2005 Jun. 22; 127(24):8686-96. PMID: 15954774

Putt K S, Hergenrother P J. A nonradiometric, high-throughput assay for poly(ADP-ribose) glycohydrolase (PARG): application to inhibitor identification and evaluation. Anal Biochem. 2004 Oct. 15; 333(2):256-64. PMID: 15450800

Putt K S, Hergenrother P J. An enzymatic assay for poly (ADP-ribose) polymerase-1 (PARP-1) via the chemical quantitation of NAD(+): application to the high-throughput screening of small molecules as potential inhibitors. Anal Biochem. 2004 Mar. 1; 326(1):78-86. PMID: 14769338

Nesterenko V, Putt K S, Hergenrother P J. Identification from a combinatorial library of a small molecule that selectively induces apoptosis in cancer cells. J Am Chem Soc. 2003 Dec. 3; 125(48):14672-3. PMID: 14640619

Putt, Karsone et al., Small scale activation of procaspase-3 as a personalized anticancer strategy, Nature Chemical Biology 2(10):543-550, S543/1-S543/29 (2006).

---

We claim:

1. A composition comprising a compound of formula:

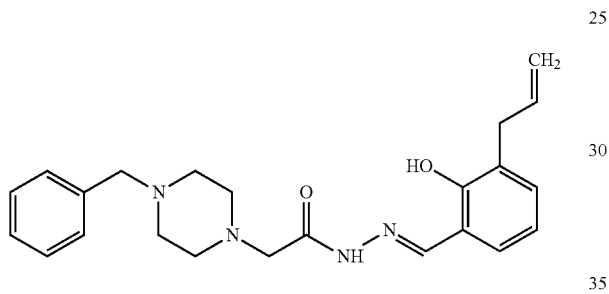

and a pharmaceutically acceptable carrier.

* * * * *